United States Patent
Babich et al.

(10) Patent No.: US 7,052,913 B2
(45) Date of Patent: May 30, 2006

(54) MATRICES FOR DRUG DELIVERY AND METHODS FOR MAKING AND USING THE SAME

(75) Inventors: John W. Babich, North Scituate, MA (US); Jon Zubieta, Syracuse, NY (US); Grant Bonavia, Kensington, MD (US)

(73) Assignee: Molecular Insight Pharmaceuticals, Inc., Cambridge, MA (US)

( * ) Notice: Subject to any disclaimer, the term of this patent is extended or adjusted under 35 U.S.C. 154(b) by 165 days.

(21) Appl. No.: 10/838,423

(22) Filed: May 4, 2004

(65) Prior Publication Data

US 2004/0241205 A1   Dec. 2, 2004

Related U.S. Application Data

(63) Continuation of application No. 10/077,475, filed on Feb. 15, 2002, now abandoned, which is a continuation of application No. 09/503,438, filed on Feb. 14, 2000, now Pat. No. 6,395,299.

(60) Provisional application No. 60/119,828, filed on Feb. 12, 1999.

(51) Int. Cl.
*A61K 9/14* (2006.01)

(52) U.S. Cl. .................................................. 435/484

(58) Field of Classification Search ................... None
See application file for complete search history.

(56) References Cited

U.S. PATENT DOCUMENTS

| | | | |
|---|---|---|---|
| 4,883,666 A | 11/1989 | Sabel et al. | 424/422 |
| 5,189,064 A | 2/1993 | Blum et al. | 514/561 |
| 5,292,801 A | 3/1994 | Avnir et al. | 525/54.1 |
| 5,300,564 A | 4/1994 | Avnir et al. | 525/54.1 |
| 5,308,495 A | 5/1994 | Avnir et al. | 210/656 |
| 5,371,018 A | 12/1994 | Avnir et al. | 436/73 |
| 5,378,232 A | 1/1995 | Easton et al. | 604/82 |
| 5,405,990 A | 4/1995 | Burke et al. | 560/134 |
| 5,457,066 A | 10/1995 | Frank et al. | 435/68.1 |
| 5,529,914 A | 6/1996 | Hubbell et al. | 435/182 |
| 5,550,050 A | 8/1996 | Holland et al. | 435/240.2 |
| 5,587,161 A | 12/1996 | Burke et al. | 424/178.1 |
| 5,624,910 A | 4/1997 | Vallee et al. | 514/27 |
| 5,639,275 A | 6/1997 | Baetge et al. | 604/891.1 |
| 5,650,311 A | 7/1997 | Avnir et al. | 435/176 |
| 5,653,975 A | 8/1997 | Baetge et al. | 424/93.1 |
| 5,660,829 A | 8/1997 | Burke et al. | 424/178.1 |
| 5,676,943 A | 10/1997 | Baetge et al. | 424/93.21 |
| 5,714,148 A | 2/1998 | Burke et al. | 424/178.1 |
| 5,759,539 A | 6/1998 | Whitmire | 424/94.3 |
| 5,759,765 A | 6/1998 | Harris et al. | 435/4 |
| 5,770,416 A | 6/1998 | Lihme et al. | 435/176 |
| 5,773,286 A | 6/1998 | Dionne et al. | 435/297.1 |
| 5,780,260 A | 7/1998 | Wedekind et al. | 435/43 |
| 5,786,216 A | 7/1998 | Dionne et al. | 435/402 |
| 5,824,526 A | 10/1998 | Avnir et al. | 435/176 |
| 5,840,307 A | 11/1998 | Swain et al. | 424/193.1 |
| 5,846,545 A | 12/1998 | Chari et al. | 424/195.11 |
| 5,849,331 A | 12/1998 | Ducheyne et al. | 424/484 |
| 5,849,588 A | 12/1998 | Naughton et al. | 435/373 |

FOREIGN PATENT DOCUMENTS

| | | |
|---|---|---|
| EP | 0 642 799 A1 | 3/1995 |
| EP | 0 795 334 A2 | 9/1997 |
| WO | WO 93/16687 | 9/1993 |
| WO | WO 97/45367 | 12/1997 |

OTHER PUBLICATIONS

Eckert-Lill et al., "Immobilized drugs: phenol and benzoic acid derivatives chemiadsorbed on silica. I. Preparation of chemiadsorbates," Abstract XP002901040, Acta Pharm. Jugosl., 38(4), pp. 373-379 (1988), (listing only).

Anderson et al, "Development of a multienzyme reactor for dopamine synthesis: II. Reactor engineering and simulation," Abstract XP002901041, Biutechno. Bioeng. 40(3), pp. 388-395 (1992), (listing only).

Database WPI, JP 54 143588, Section Ch, Week 197951, Derwent Publications Ltd., London, GB, Abstract XP002901042, (Abstract only).

Database WPI, Section Ch., Week 199318, Derwent Publications Ltd., London, GB; class A96, AN 1993-149780; XP002901043; & JP 05 087811 A (Komica Corp), Apr. 6, 1993, (Abstract only).

International Search Report—PCT/US00/03754 (2000).

Aboagye et al.; Intrtumoral Conversion of 5-Fluorocytosine to 5-Fluorouracil by Monoclonal Antobody-Cytosine Deaminase Conjugates: Noninvasive Detection of Produg Activation by Magnetic Resonance Spectroscopy and Spectrocopic Imaging[1], Cancer Research 58:4075-4078 (Sep. 15, 1998).

(Continued)

Primary Examiner—Charles L. Patterson, Jr.
(74) Attorney, Agent, or Firm—Foley & Lardner LLP; Michel Morency; James Ewing

(57) ABSTRACT

In one aspect, biocompatible matrices such as sol-gels encapsulating a reaction center may be administered to a subject for conversion of prodrugs into biologically active agents. In certain embodiments, the biocompatible matrices of the present invention are sol-gels. In one embodiment, the enzyme L-amino acid decarboxylase is encapsulated and implanted in the brain to convert L-dopa to dopamine for treatment of Parkinson's disease.

20 Claims, 13 Drawing Sheets

OTHER PUBLICATIONS

Adachi et al.; "A Sensitive Fluorometric Assay Method for Mammalian Tyrosinase", Biochem. Biophys. Res. Commun., 26: (2): 242-246 (1967).

Akbarian et al.; Spectroscopic Determination of Cholinesterase Activity and Inhibition in Sol-Gel Media, Journal of Sol-Gel Science and Technology 8: 1067-1070, (1997).

Audebert et al.; Electrochemical Probing of the Activity of Glucose Oxidase Embedded Sol-Gel Matrices, Chem. Mater. 5 : 911-913 (1999).

Avnir David; Organic Chemistry Within Ceramic Matrices: Doped Sol-Gel Materials, Acc. Chem. Res. 28 (8): 328-334 (1995).

Avnir et al.; Organic Fluorescent Dyes Trapped in Silica and Silica-Titania Thin Films by the Sol-Gel Method Photophysical, Film and Cage Properties, Journal of Non-Crystalline Solids 74 : 395-406, (1985).

Avnir et al.; The Nature of the Silica Cage as Reflected by Spectral Changes and Enhanced Photostability of Trapped Rhodamine 6G, The Journal of Physical Chemistry , 88 (24): 5956-5959 , (1984 ).

Avvnir et al.; Enzymes and Other Proteins Entrapped in Sol-gel Materials , Chem. Mater. 6: 1605-1614 (1994).

Bagshawe et al.; "A Cytotoxic Agent can be Generated Selectively at Cancer Sites", Br. J. Cancer 58: (6): 700-703 (1988).

Bagshawe et al.; "Antibody Directed Enzymes Revive Anti-Cancer Prodrugs Concept", Br. J. Cancer, 56: (5): 531-532 (1987).

Bagshawe, K. D.; "ADEPT and Related Concepts", Cell Biophysics. 24/25: 83-91 (1994).

Bennett and Evans, "Alzheimer's Disease", Disease-a-Month pp. 1-64, (Jan. 1992).

Blakey, et al.; "Anti-tumour Effects of an Antibody-Carboxypeptidase G2 Conjugate in Combination with Phenol Mustard Prodrugs", Br. J. Cancer, 72: (5): 1083-1088 (1995).

Brannan et al.; Effect of Long-term-L-dopa Administration on Striatal Extracellular Dopamine Release, Neurology 41: 596-598 (1991).

Braun et al.; Biocatalysis by Sol-gel Entrapped Enzymes, Journal of Non- Crystalline Solids, 147& 148,: 739-743, (1992 ).

Bressler and Braun ; Use of Sol-Gel Entrapment Techniques for the Resolution of Itaconic Acid Biosynthetic Pathway in *Aspergillus terreus*, Journal of Sol-Gel Science and Technology 7: 129-133 (1996).

Bronshtein et al.; "Sol-Gel Matrixes Doped with Atrazine Antibodies: Atrazine Binding Peoperties", Chem. Mater. 9:2632-2639 ,( 1997).

Calne B. Donald; Drug Therapy: Treatment of Parkinson's Disease, The New England Journal of Medicine , 329(14): 1021-1027 (Sep. 30, 1993).

Caniato et al.; "Immobilization of Plant Cells in Hybrid Sol-Gel Materials", Journal of Sol-Gel Science and Technology 7: 87-97 ,(1996).

Carlsson Arvid, Thirty Years of Dopamine Research, Advances in Neurology 60: 1-10 ((1993).

Caruso et al.; Nanoengineering of Inorganic and Hybrid Hollow Spheres by Colloidal Templating, Science 282: 1111-1113 (Nov. 6, 1998).

Chang, T.M. Methods for the Therapeutic Applications of Immobilized Enzymes, Methods Enzymol., 44: 676-698 (1976).

Chen et al.; Phycobiliproteins Encapsulated in Sol-Gel Glass, Journal of Sol-Gel Science and Technology, 7: 99-108 ( 1996).

Collino et al.; "Biological Activity of Functionalized $SiO_2$ Thin Films Prepared by Sol-Gel Method", Journal of Sol-Gel Science and Technology 7: 81-85 (1996 ).

Dave et al.; Sol-Gel Encapsulation Methods for Biosensors, Analytical Chemistry, 66(22): 1120-1127 (Nov. 15, 1994 ).

Dave et al.; Encapsulation of Proteins in Bulk and Thin Film Sol-Gel Matrices, Journal of Sol-Gel Science and Technology 8: 629-634 (1997).

Davis et al.; Soluble, Nonantigenic Polyethylene Gylcol-Bound Enzymes[1], Biomedical Polymers Edited by Eugene P. Goldberg and Akio Nakajima, pp. 441-452 ( 1980).

Denny and Wilson, The Design of Selectively-Activated Anti-Cancer Prodrugs for Use in Antibody-Directed and Gene-Directed Enzyme-Produg Therapies, J. Pharm. Pharmacol. 50: 387-394 (1998).

Deonarain & Epenotos; "Targeting Enzymes for Cancer Therapy: Old Enzymes in New Roles", Br. J. Cancer 70: 786-794 (1994).

Dominici et al,; Purification and Characterization of Rat-Liver 3,4-dihydroxyphenylalanine Decarboxylase, Euro. J. Biochem., 169: 209-213 (1987).

Dosoretz et al.; Entrapment of Parathion Hydrolase from Pseudonomas Spp. In Sol-Gel Glass, Journal of Sol-Gel Science and Technology 7: 7-11 (1996).

Dowell et al.; New Mustard Prodrugs for Antibody-Directed Enzyme Prodrug Therapy: Alternatives to the Amide Link, J. Med. Chem. 39: 1100-1105 ( 1996).

Driscoll et al.; Lipophilic, Acid-Stable, Adenosine Deaminase-Activated Anti-HIV Produgs for Central Nervous System Delivery. 3. 6-Amino Prodrugs of 2- β-Fluoro-2',3'-dideoxyinosine, J. Med. Chem. 39: 1619-1625 91996).

Duckwrth and Coleman, Physicochemical and Kinetic Properties of Mushroom Tyrosinase, The Journal of Biological Chemistry , 245 (7): 1613-1625 (Apr. 10, 1970 ).

Dunn and Zink, Probe of Pore Environment and Molecule-Matrix Interactions in Sol-Gel Materials, Chem. Mater. 9:2280-2291 (1997).

Dunn et al.; Strategies for Encapsulating Biomolecules in Sol-Gel Matrices, Acta Mater, 46(3): 737-741 ( 1998).

Eccles et al.; Regression of Established Breast Carcimona Xenografts with Antibody-directed Enzymes Prodrugs Therapy against c-erbB2 p 185[1], Cancer Research 54: 5171-5177, (Oct. 1, 1994).

Ellerby et al.; "Encapsulation of Proteins in Transparent Porous Silicate Glasses Prepared by the Sol-Gel Method", Science , 255: 1113-1114 ( Feb. 28, 1992 ).

Emerich et al.; "Protective Effect of Encapsulated Cells Producing Neurotrophic Factor CNTF in a Monkey Model of Huntington's Disease", Nature, 386: 395-399 (Mar. 1997 ).

Florent et al.; "Prodrugs of Anthracyclines for Use in Antibody-Directed Enzyme Prodrug Therapy", J. Med. Chem. 41: 3572-3581 ( 1998).

Friedlos et al.; Mustard Prodrugs for Activation by *Escherichia coli* Niitroreductase in Gene-Directed Enzyme Prodrug Therapy, J. Med. Chem. 40: 1270-1275, (1997).

Glezer V. and Lev O.; Sol-Gel Vanadium Pentaoxide Glucose Biosensor, J. Am. Chem. Soc. 115: 2533-2534, ( 1993).

Haenseler et al., "Activation of Methotrexate-α-Alanine by Carboxypeptidase A-Monoclonal Antibody Conjugate", Biochemistry, 31:(3):891-897 (1992).

Hayashi et al.; "Rat Liver Aromatic L-Amino Acid Decarboxylate: Spectroscopic and Kinetic Analysis of the Coenzyme and Reaction Intermediates", Biochemistry 32 (3): 812-818 , ( 1993).

Hatayama et al.; Immobilization of Unrease on Composite Fibre By Using a Gel Formation of Cellulose Acetase and Titanium Iso-Propoxide, Journal of Sol-Gel Science and Technology 7, : 13-17 ( 1996).

Hellström et al.; "Activation of Prodrugs by Targeted Enzymes", Euro. J. of Cancer 27(11): p. 1342, ( 1991 ).

Huennekens M. K. ; Tumor Targeting : Activation of Prodrugs by Enzyme-Monoclonal Antibody Conjugates, T I Btech., 12: 234-239 (Jun. 1994 ).

Jaeger K. and Reetz T. M. ; Microbial Lipases Form Versatile Tools for Biotechnology, TIBtech. , 16 : 396-403 (Sep. 1998 ).

Jain et al.; Nanometer Silica Particles Encapsulating Active Compounds: a Novel Ceramic Drug Carrier, J. Am. Chem. Soc. 120: 11092-11095 (1998).

Ji, Q. et al.; Sol-Gel—Encapsulated Heme Proteins. Evidence for $CO_2$ Adducts, J. Am. Chem. Soc. , 120: 221-222 (1998).

Jung J. M. ; Substrates and Inhibitors of Aromatic amino Acid Decarboxylase, Bioorganic Chemistry , 14:429-443 ( 1986 ).

Jungheim and Shepherd; Design of Antitumor Prodrugs: Substrates of Antibody Targeted Enzymes, Chem. Rev. 94: 1553-1566 (1994).

Jungheim et al.; Synthesis of Acylhydrazido-Substituted Cephems. Design of Cephalosporin-Vinca Alkaloid Prodrugs: Substrates for an Antibody-Targeted Enzyme, J. Org. Chem., 57: 2334-2340 (1992 ).

Kerr et al., "Antibody-penicillin-V-amidase Conjugates Kill Antigen-Positive Tumor Cells When Combined with Doxorubicin Phenoxyacetamide", Cancer Immunol. Immunother., 31: (4): 202-206 (1990).

Klein and Langer; Immobilized Enzymes in Clinical Medicine: An Emerging Approach to New Drug Therapies, TIBtech, 179-186 ( Jul. 1986).

Knox et al.; Virtual Cofactors for an *Escherichia coli* Nitroreductase Enzyme : Relevance to Reductively Activatred Prodrugs in Antibody Directed Enzyme Prodrug Therapy ( Adept), Biochemical Pharmacology, 49(11): 1641-1647 (1995).

Lan et al.; Encapsulation of the Frritin Protein in Sol-Gel Derived Silica Glasses, Journal of Sol-Gel Science and Technology 7, 109-116 (1996).

Levy et al.; "Application of the Sol-Gel Process for the Preparation of Photochromic Information -Recording Materials: Synthesis, Properties, Mechanisms", Journal of Non-Crystalline slods 113: 137-143 (1989).

Li et al.; "Bioactive $Ca_{10}(PO_4)_6(OH)_2$- Ti $O_2$ Composite Coating Prepared by Sol-Gel Process", Journal of Sol-Gel Science and Technology ,7: 27-34, (1996).

Lin et al.; Biogels of Cytochrome c: Cytochrome c Peroxidase Complex Studied by Electron Paramagnetic Resonance Spectroscopy, Journal of Sol-Gel Science and Technology, 7: 19-26 (1996).

Lindström Per; "Aromatic-L-Amino-Acid Decarboxylase Activity in Mouse Pancreatic Islets", Biochimica and Biophysica Acta, 884: 276-281 (1986).

Livage et al.; Immunoassays in Sol-Gel Matrices, Journal of Sol-Gel Science and Technology, 7: 45-51, (1996).

Lobel et al.; "In Vitro Protein Interactions with a Bioactive Gel-Glass", Journal of Sol-Gel Science and Technology, 7: 69-76 (1996).

Mann, et al.; "Synthesis of an N-Mustard Prodrug", Tetrahedron, 46(15): 5377-5382 (1990).

Marais et al.; "Gene-Directed Enzyme Prodrug Therapy with a Mustard Prodrug/ Carboxypeptidase G2 Combination [1]", Cancer Research, 56: 4735-4742, (Oct. 15, 1996).

Marsden et al.; An Introduction to the New Surgery for Parkinson's Disease, Advances in Neurology, 74: 143-147 (1997).

Marques and Brodelius; Elicitor-Induced L-Tyrosine Decarboxylase from Plant Cell Suspension Cultures [1] , Plant Physiol. ,88: 46-51, (1988).

Martin, et al.; Antibody-Directed Enzyme Prodrug Therapy: Pharmacokinetics and Plasma Levels of Prodrug and Drug in a Phase I Clinical Trial, Cancer Chemother Pharmacol. , 40: 189-201, (1997).

Melton and Sherwood, Antibody-Enzyme Conjugates for Cancer Therapy, Journal of the National Cancer Institute. 88(3/4): 153-165, (Feb. 21, 1996).

Meyer et al.; Site-Specific Prodrug Activation by Antibody-β-Lactamase Conjugates: Regression and Long-Term Growth Inhibition of Human Colon Carcinoma Xenograph Models, Cancer Research, pp. 3956-3963 (1993).

Miller et al.; Synthesis Conditions for Encapsulating Cytochrome c and Catalase in $SiO_2$ Sol-Gel Materials, Journal of Non-Crystalline Solids 202: 279-289, (1996).

Nishigaki et al.; "Purification of Aromatic L- Amino Acid Decarboxylase From Bovine Brain with a Monoclonal Antibody", Biochem. J. , 252: 331-335 (1988).

Nishiyama et al.; Antineoplastic Effects in Rats of 5-Fluorocytosine in Combination with Cytosine Deaminase Capsules [1], Cancer Research 45: 1753-1761, (Apr. 1995).

Pereira and Hench; "Mechanisms of Hydroxyapatite Formation on Porous Gel-Silica Substrates", Journal of Sol-Gel Science and Technology, 7: 59-68 (1996).

Peterson et al. ; Silica Sol-Gel Encapsulation of Pancreatic Islets, Proc. Soc. Exp. Biol. Med. 218: 365-369, (Sep. 1998).

Pomerantz, S., and Li, P-C., "Tyrosinases [1, 1a, 2] (Hamster Melanoma)", Meth. Enzymol. 17, Pt. A, 620-626 (1970).

Pummer and Hollon; "The Man who Rescued Gliadel", Modern Drug Discovery, pp. 30-41, (Sep./Oct., 1998).

Reetz et al.; "Efficient Heterogenous Biocatalysts by Entrapment of Lipases in Hydrophobic Sol-Gel Materials", Angew. Chem. Int. Ed. Engl., 34(3): (1995), 301-303.

Reetz et al.; Characterization of Hydrophobic Sol-Gel Materials Containing Entrapped Lipases, Journal of Sol-Gel Science and Technology 7: 35-43, ( 1996).

Rietti-Shati et al.; Atrazine Degradation by Pseudomonas Strain ADP Entrapped in Sol-Gel Glass, Journal of Sol-Gel Science and Technology, 7: 77-79, (1996).

Roux et al. ; Antibody- Antigen Reactions in Porous Sol-Gel Matrices, Journal of Sol-Gel Science and Technology , 8: 663-666, (1997).

Sabel et al.; Controlled -Release Dopamine Polymers as a Novel Approach to the Treatment of Parkinson's Disease, Advances in Neurology 53 : 513-518, (1990).

Sampath et al.; Sol-Gel Derived Ceramic-Carbon Enzyme Electrodes: Glucose Oxidase as a Test Case, Journal of Sol-Gel Science and Technology , 7: 123-128, (1996).

Samuel et al.; Determination of Activation Energy of Entrance Into Micropores: Quenching of the Fluorescence of Pyrene-Doped $SiO_2$ Sol-Gel Matrices by Oxygen, Chem. Mater. 6: 1457-1461, (1994).

Senter D. Peter; Activation of Prodrugs by Antibody-Enzyme Conjugates: a New Approach to Cancer Therapy, FASEB J. 4: 188-193; (Feb.1990).

Shaba et al.; An Efficient Sol-Gel Reactor for Antibody-Catalyzed Transformations, Chem. Mater. 9: 2258-2260, (1997).

Soghomonian et al.; A Square-Pyramidal Tetrahedral Vanadium Phosphate Framework Solid Incorporating Propanedianemmonium Dications. The Structural Characterization of $(H_3 NCH_2 CH_2 CH_2 NH_3) K [(VO)_3 (PO_4)_3]$, Chem. Mater. 5: 1595-1597, (1993).

Sourkes, L. Theodore; "Aromatic-L-Amino Acid Decarboxylase", Methods in Enzymology, 142: 170-178, (1987).

Springer et al.; Ablation of Human Choriocarcinoma Xenografts in Nude Mice by Antibody-Directed Enzyme Prodrug Therapy (ADEPT) with Three Novel Compounds, Eur. J. Cancer 27(11): 1361-1366, (1991).

Springer et al.; "Novel Prodrugs Which Are Activated to Cytotoxic Alkylating Agents by Carboxypeptidase G2", J. Med. Chem. 33: 677-681, (1990).

Springer et al.; "Novel Prodrugs of Alkylating Agents Derived from 2-Fluoro- and 3-Fluorobenzoic Acids for Antibody-Directed Enzyme Prodrug Therapy", Journal of Medicinal Chemistry, 37: (15): 2361-2370, (1994).

Steiner et al.; Assay for Tyrosine Hydroxylation Activity of Tyrosinase from Betalain-Forming Plants and Cell Cultures, Analytical Chemistry 238: 72-75, (1996).

Stewart, et al Dopamine Beta-Hydroxylase of Adrenal Chromaffin Granules: Structure and Function, Ann. Rev. Biochem., 57: 551-592, (1988).

Stiegman et al.; "Vanadia/Silica Xerogels and Nanocomposites", Chemistry of Materials, 5(11): 1591-1595 (Nov. 1993).

Stribbling et al.; Biodistribution of an Antibody-Enzyme Conjugate for Antibody-Directed Enzyme Prodrug Therapy in Nude Mice Bearing a Human Colon Adenocarcinoma Xenograft, Cancer Chemother. Pharmacol., 40: 277-284 (1997).

Turniansky et al.: Sol-Gel Entrapment of Monoclonal Anti-Atrazine Antibodies, Journal of Sol-Gel Science and Technology, 7: 135-143, (1996).

Vachtenhein et al.; A Spectophotometric Assay for Mammalian Tyrosinase Utilizing the Formation of Melanochrome from L-Dopa, Analytical Biochemistry, 146: 405-410, (1985).

Voltattom et al.; Aromatic-L-Amino Acid Decarboxylase from Pig Kidney, Methods in Enzymology, 142: 179-187 (1987).

Wambolt and Saavedra, "Iodide Fluorescence Quenching of Sol-Gel Immobilized BSA", Journal of Sol-Gel Science and Technology, & : 53-57, (1996).

Wang et al.; "Affinity of Antifluorescein Antibodies Encapsulated Within a Transparent Sol-Gel Glass", Anal. Chem., 65: 2671-2675, (1993).

Weetall et al.; "Bacteriorhodopsin Immobilized in Sol-Gel Glass", Biochimica et Biophysica Acta1142: 211-213, (1993).

Winder J. Alison; "A Stopped Spectrophotometric Assay for the Dopa Oxidase Activity of Tyrosinase", J. Biochem. Biophys. Methods, 28: 173-183 (1994).

Wu, et al.; "Bacteriorhodopsin Encapsulated in Transparent Sol-Gel Glass: A New Biomaterial", Chem. Mater 5: 115-120, (1993).

Yahr D. Melvin; "Parkinson's Disease the L-Dopa Era", Advances in Neurology, 60: pp. 11-17, (1993).

Yamanaka et al.; Nicotinamide Adenine Dinucleotide Phosphate Fluorescence and Absorption Monitoring of Enzymatic Activity in Silicate Sol-Gel for Chemical Sensing Applications, J. Am. Chem. Soc. 117: 9095-9096, (1995).

Yamanaka et al.; Enzymatic Activity of Glucose Oxidase Encapsulated in Transparent Glass by the Sol-Gel Method, Chemistry of Materials, 4(3): 495-496, (May/Jun., 1992).

Yamanaka et al.; Enzymatic Activity of Oxalate Oxidase and Kinetic Measurements by Optical Methods in Transparent Sol-Gel Monoliths, Journal of Sol-Gel Science and Technology, 7: 117-121, (1996).

Yang et al.; "Generalized Syntheses of Large -Pore Mesoporous Metal Oxides With Semicrystalline Frameworks", Nature, 396: 152-155, (Nov. 12, 1998).

Zheng et al.; Measurement of Fluorescence from Tryptophan to Probe the Environment and Reaction Kinetics within Protein-Doped Sol-Gel-Derived Glass Monoliths, Anal. Chem. 69: 3940-3949, (1997).

Zink et al.; "Biomolecular Materials Based on Sol-Gel Encapsulated Proteins", New J. Chem. 18: 1109-1115, (1994).

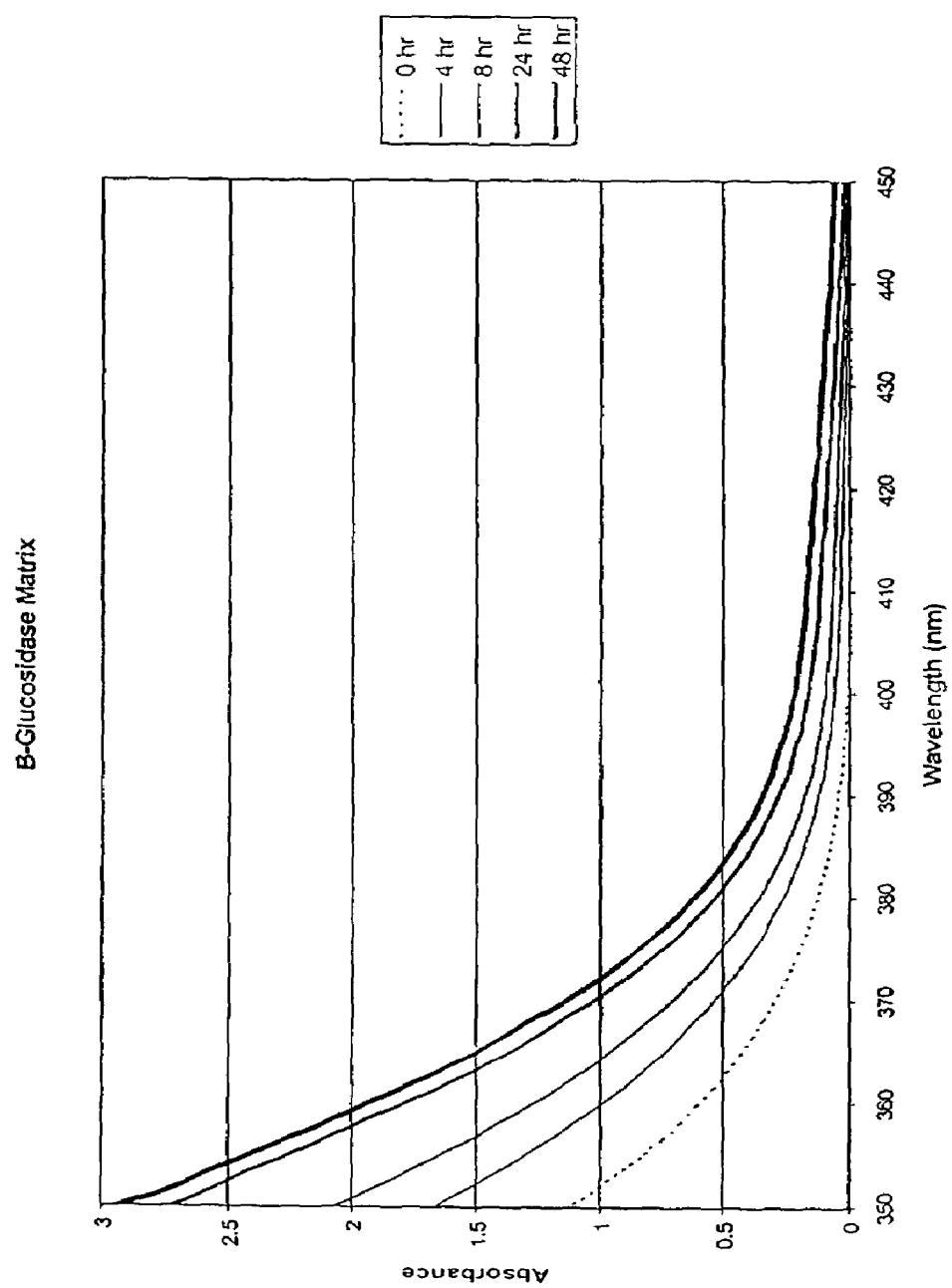
Figure 1. Enzymatic activity assay for a matrix containing β-Glucosidase.

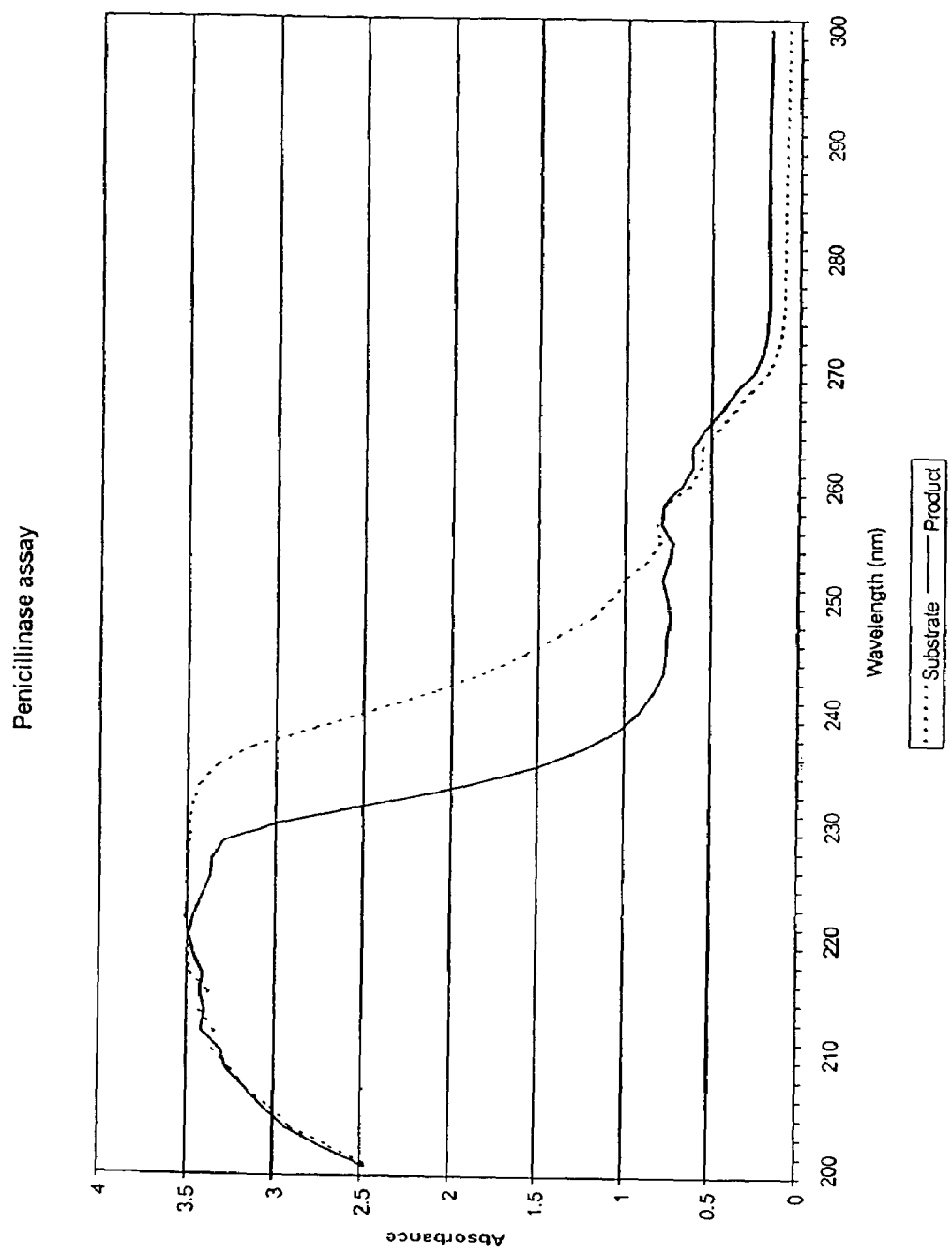
Figure 2. Substrate and product spectra for penicillinase assay.

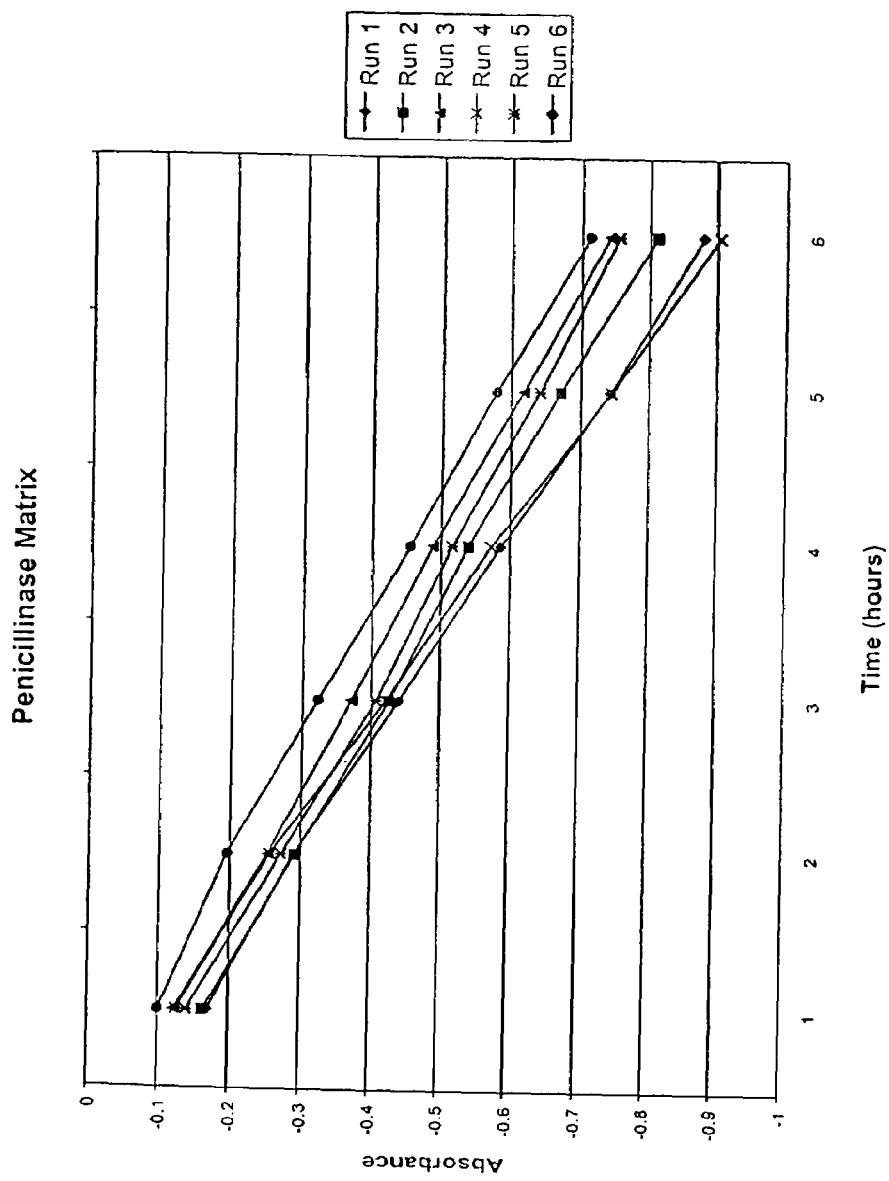
Figure 3(a) Penicillinase activity assays showing (a) multiple assays of a single matrix and (b) a single assay performed on each of five matrices from one batch preparation.

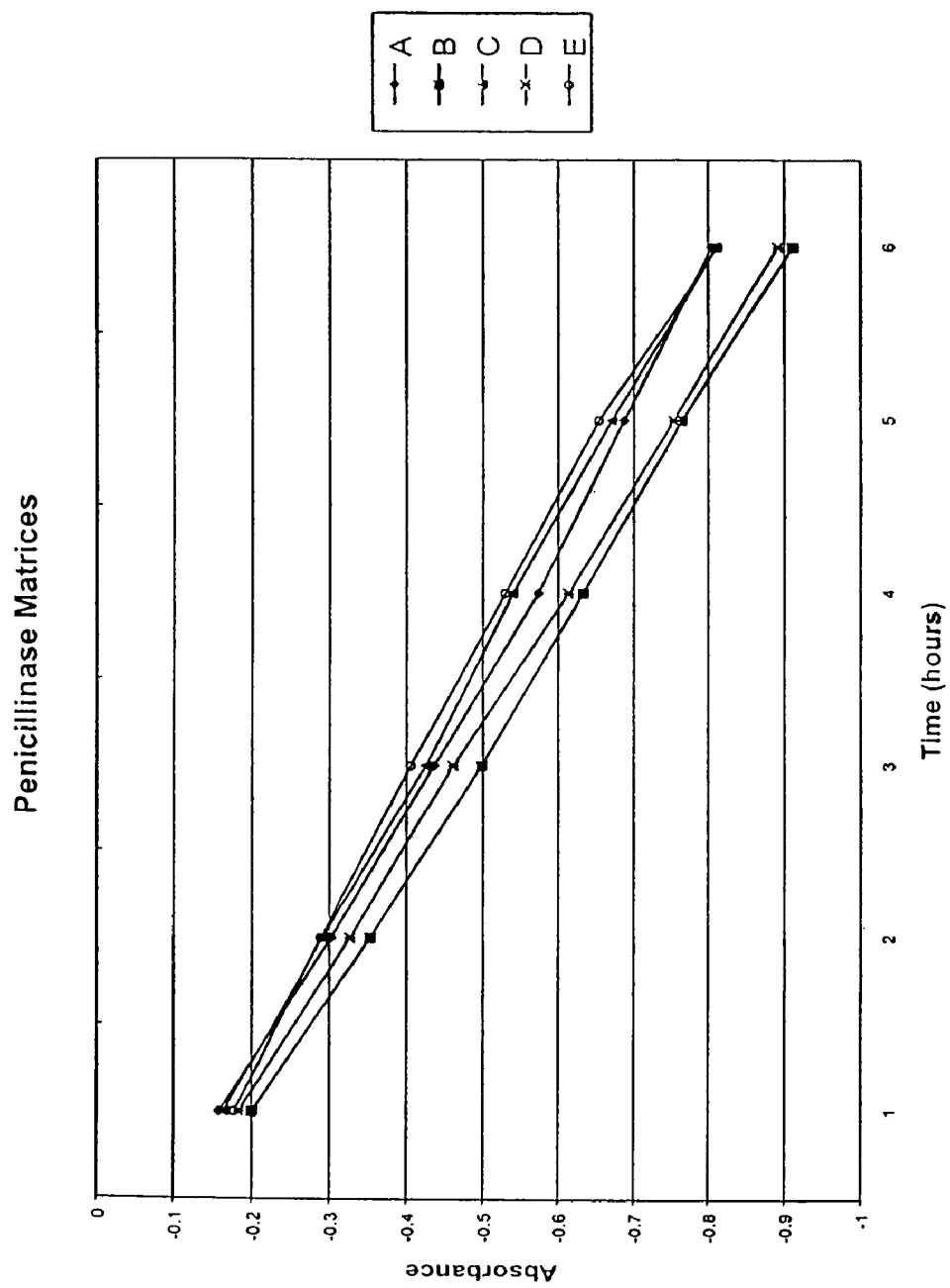
Figure 3(b). See the legend directly above.

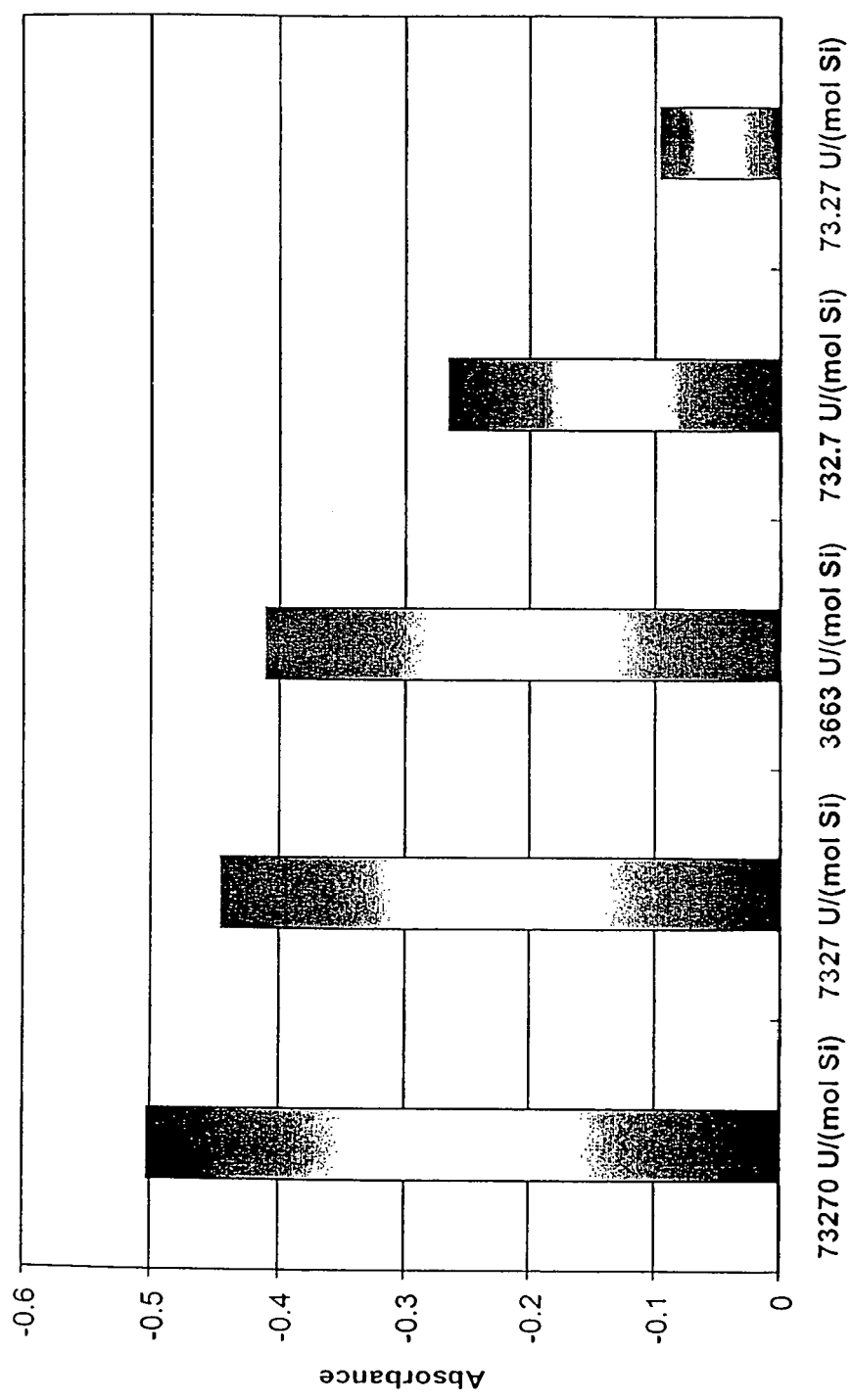
Figure 4. Change in absorbance at three hours as a function of the enzyme concentration added to the matrix during preparation.

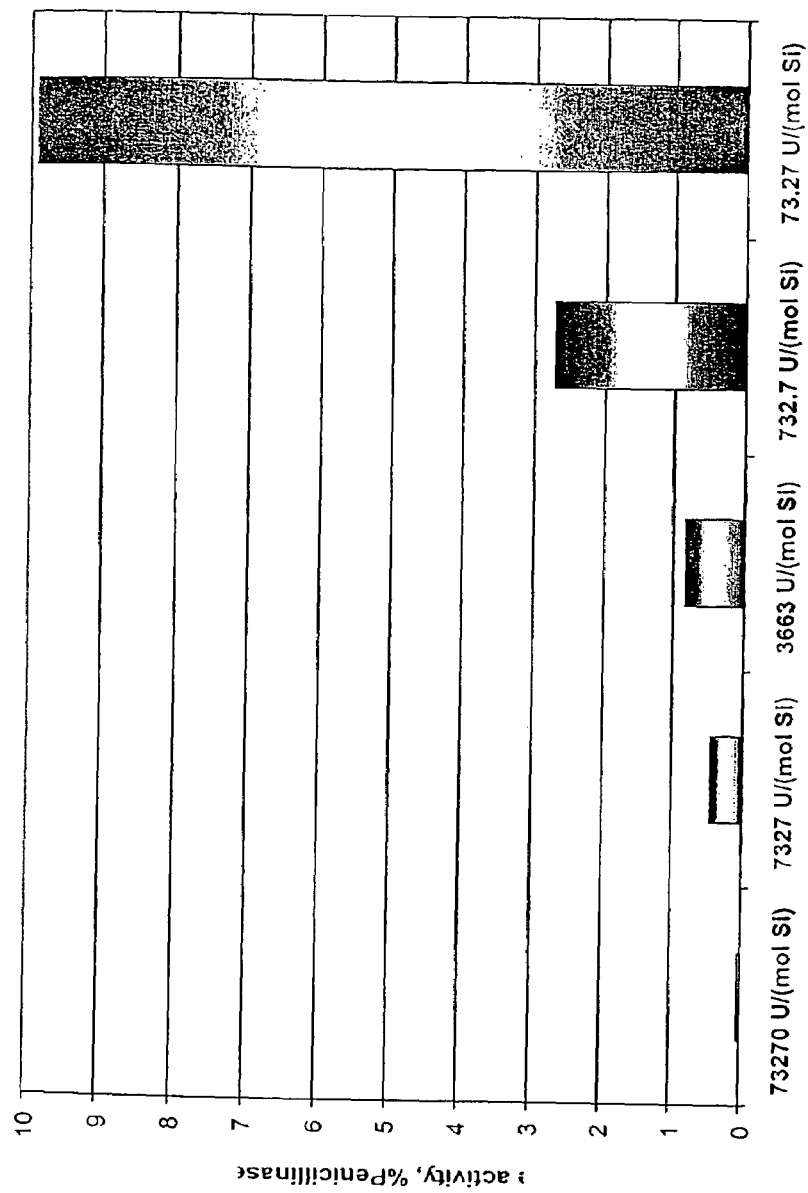
Figure 5. Yield of immobilized enzyme in penicillinase-containing sol-gel matrices. (Observed activity was calculated as the percentage of enzyme activity used in the preparation of the matrices).

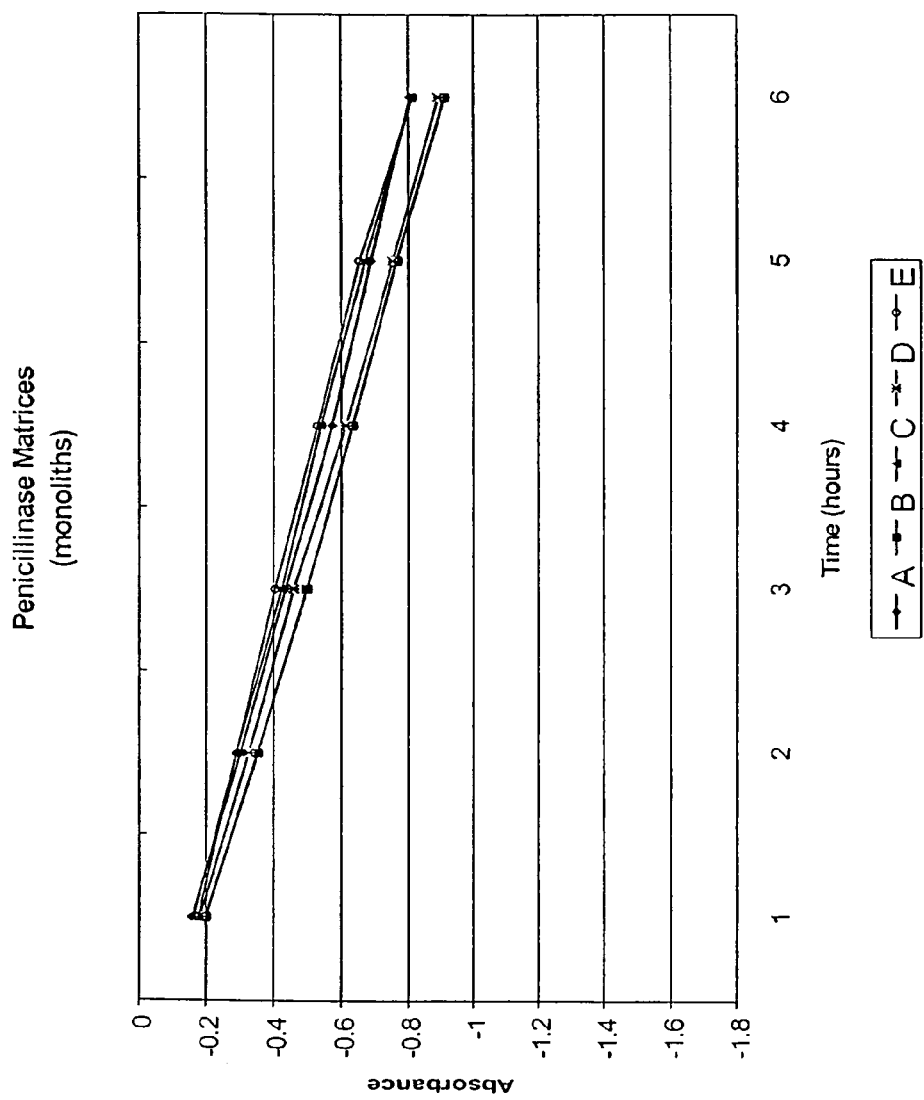
Figure 6(a). Activity of crushed and whole matrices containing penicillinase. Each figure shows data for five unique matrices assayed one time each.

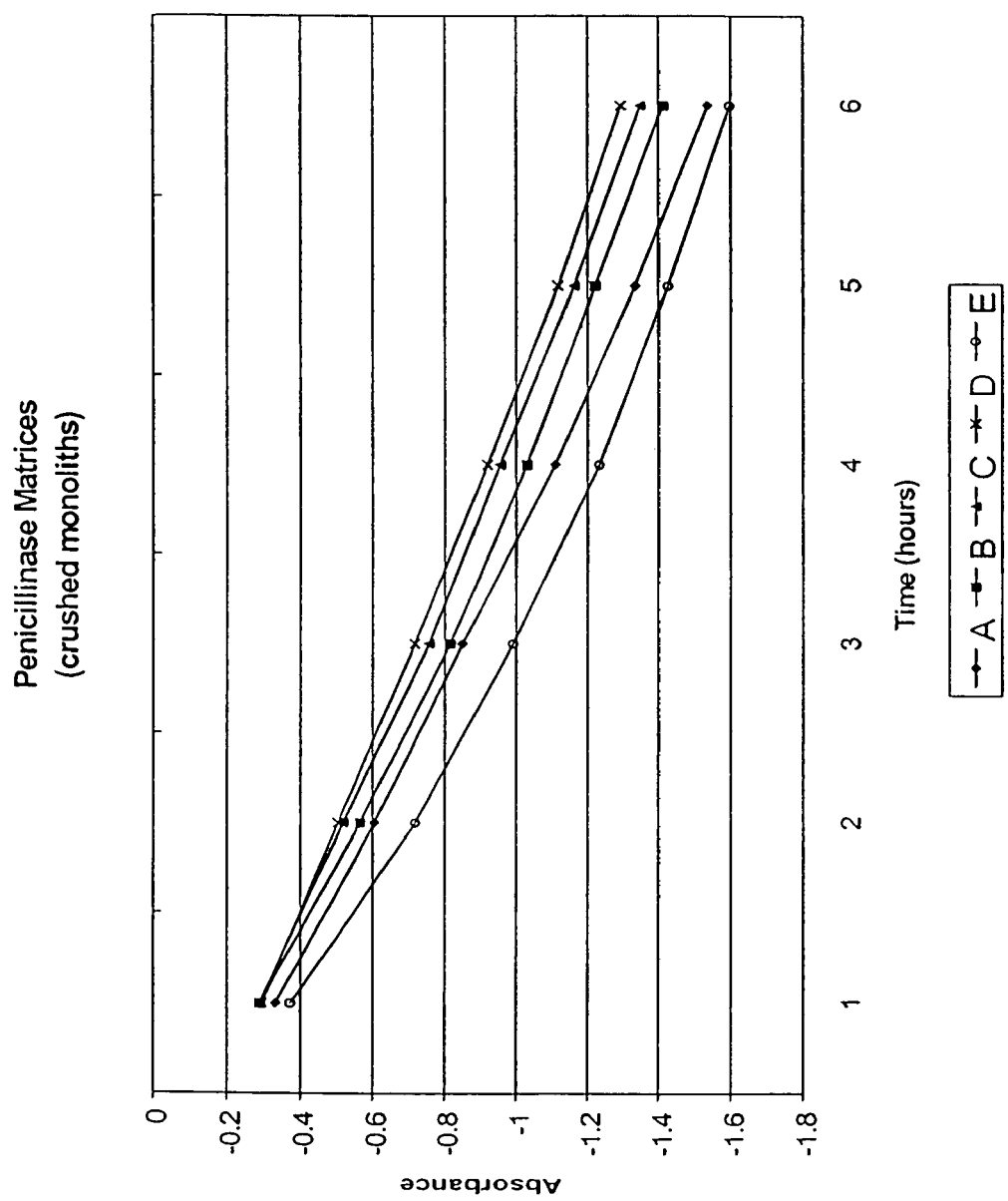
Figure 6(b). See legend directly above.

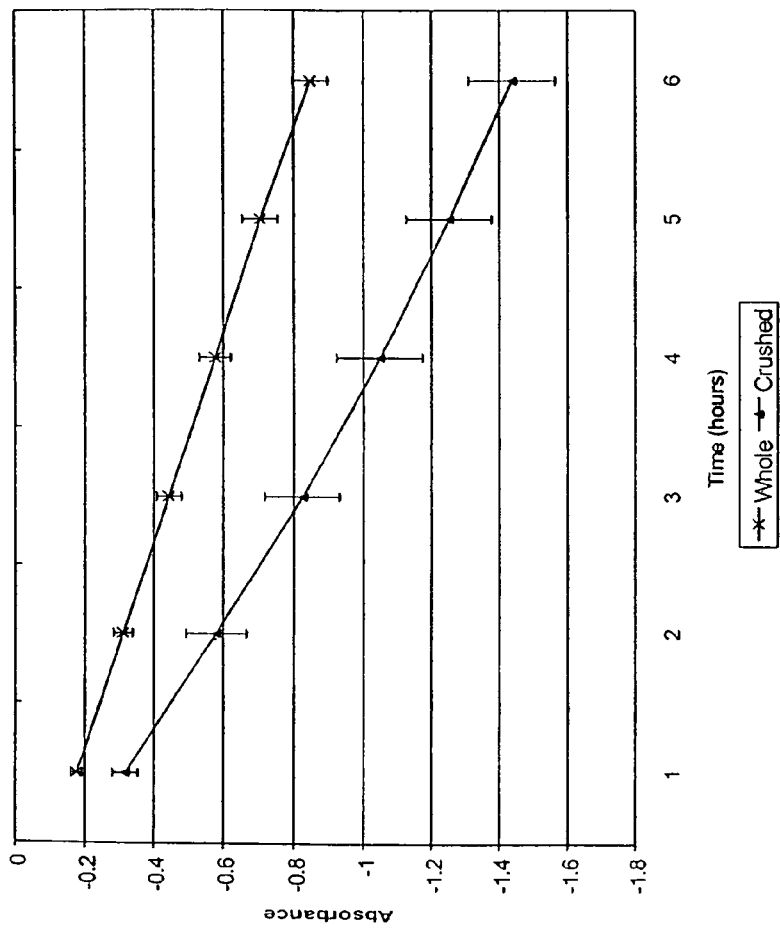
Figure 7: Penicillinase activity in whole monoliths and crushed matrices with points shown being the mean of five measurements (error bars +/- one standard deviation).

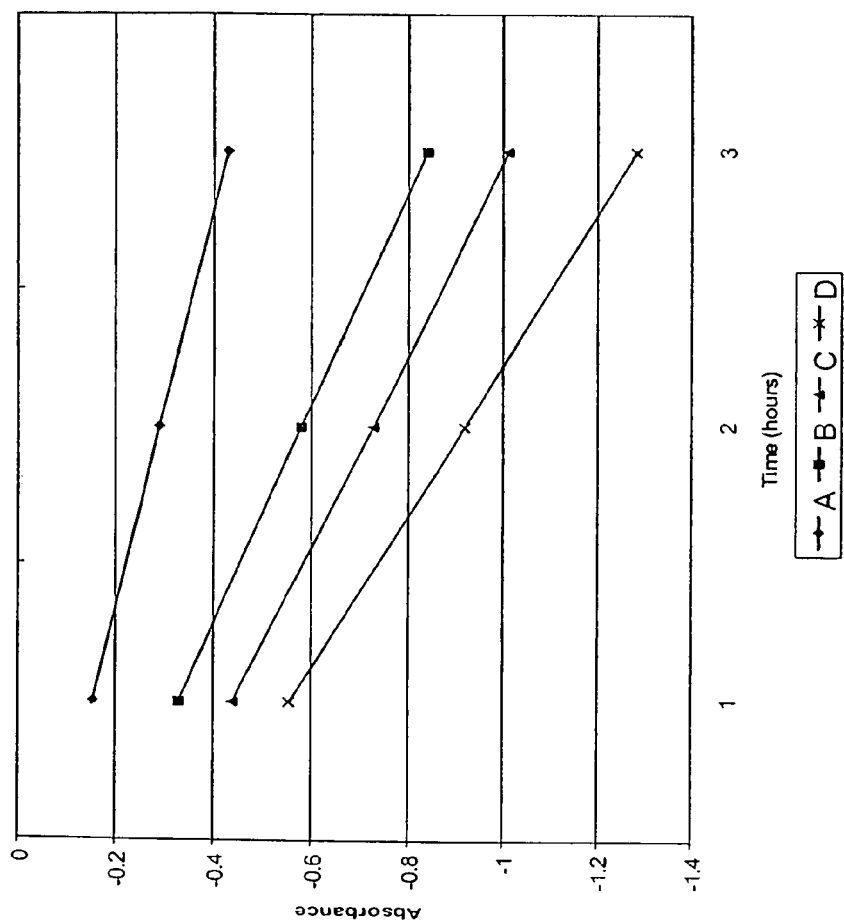
Figure 8(a). (a) Activity of penicillinase-containing matrices with varying surface areas and (b) activity as a percentage of the activity added in preparation. Surface areas corresponding to the labeling in the graphs are: A = 15.1 cm$^2$, B = 39.2 cm$^2$, C = 71.3 cm$^2$ and D = 135 cm$^2$.

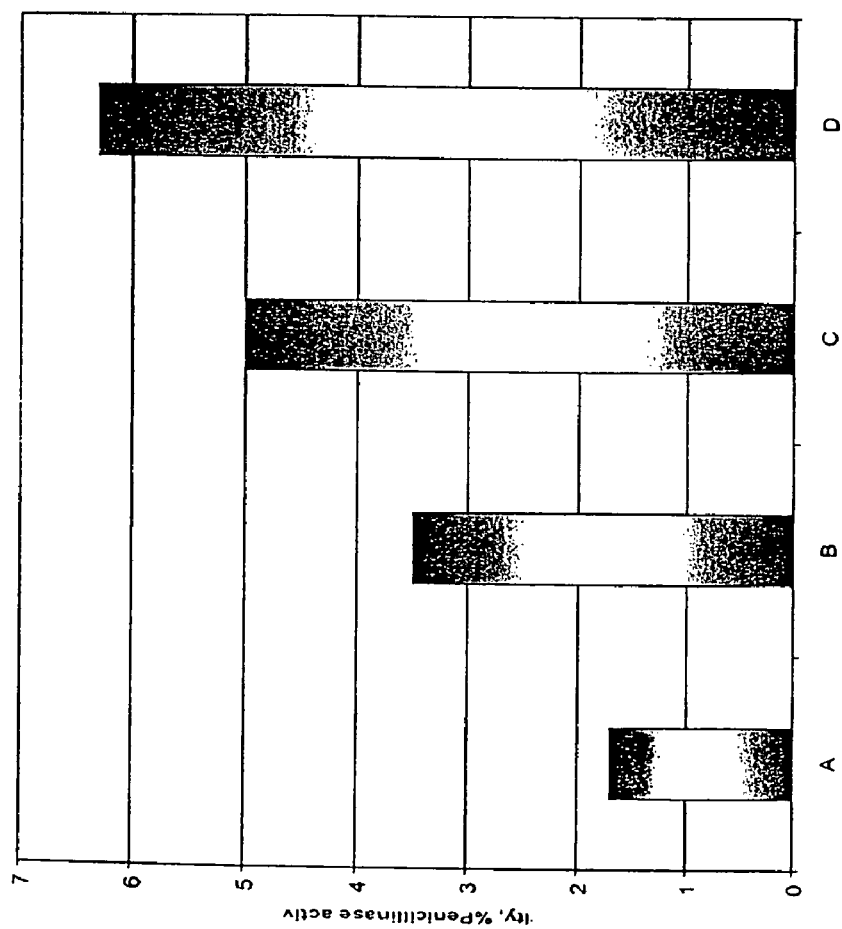
Figure 8(b). See legend directly above.

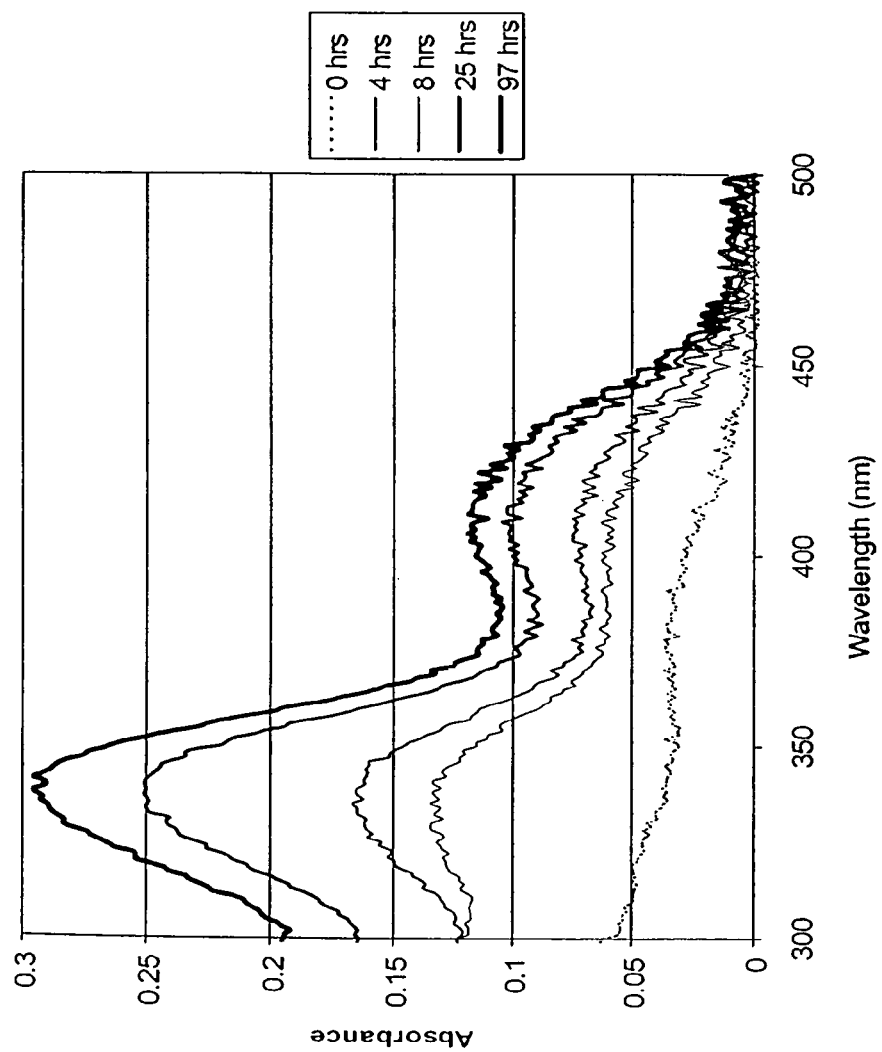
Figure 9. Tyrosine decarboxylase activity assay; elapsed time since gel cast 19.5h.

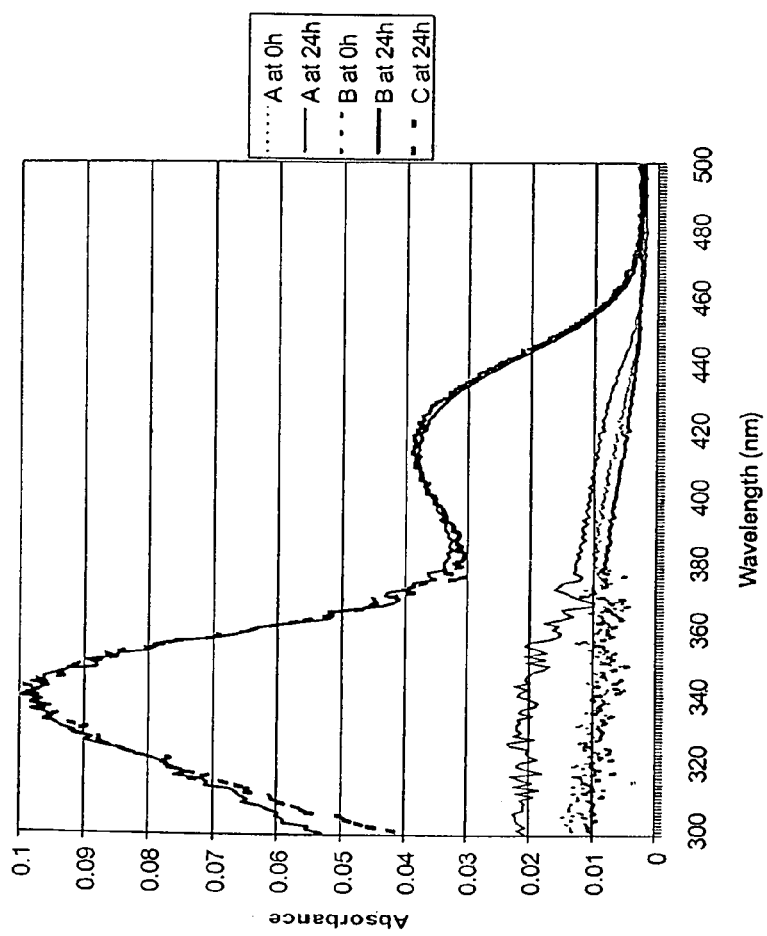
Figure 10, Tyrosine decarboxylase activity assay of two identical 16 day old matrices, A and B, with comparison to C (same matrix composition aged 19h, no cofactor present). Assay of A is performed in the absence of pyridoxal-5-phosphate (cofactor) while B is performed with cofactor present.

MATRICES FOR DRUG DELIVERY AND METHODS FOR MAKING AND USING THE SAME

1. RELATED APPLICATION INFORMATION

This Application claims the benefit of priority under 35 U.S.C. section 119(e) to Provisional Application 60/119,828, filed Feb. 12, 1999.

2. INTRODUCTION

Many clinical conditions, deficiencies, and disease states may be remedied or alleviated by providing to a patient beneficial biologically active agents or removing from the patient deleterious biologically active agents. In many cases, provision of beneficial agents or removal of deleterious ones may restore or compensate for the impairment or loss of function or homeostasis. An example of a disease or deficiency state whose etiology includes loss of such an agent include Parkinson's disease, in which dopamine production is diminished. The impairment or loss of such agents may result in the loss of additional metabolic functions.

Parkinson's disease, one of many motor system disorders, results in symptoms such as tremor, bradykinesia, and impaired balance. Keller in *Handbook of Parkinson's Disease* (Marcel-Dekker Inc.: New York 1992). Parkinson's disease is both chronic and progressive, and nearly 50,000 Americans are diagnosed with Parkinson's disease each year. More than half a million Americans are currently being treated for Parkinson's disease. Bennett et al. *Dis. Mon.* 38:1 (1992).

A specific area of the brain known as the basal ganglia is affected in Parkinson's disease. The basal ganglia plays a vital role in voluntary movement control. A region of the basal ganglia termed the substantia nigra is important in the synthesis of the neurotransmitter dopamine. Deterioration of the dopamine producing cells in the substantia nigra results in the characteristic symptoms of Parkinson's disease. These symptoms are thought to be due to a deficiency of dopamine in both the substantia nigra and the striatum. Obeso et al., *Advances in Neurology* 74:143 (1997). The striatum requires a balance of the neurotransmitters dopamine and acetylcholine in order to control properly movement, balance, and walking. The cause of the impairment or death of the cells responsible for the production of dopamine in the substantia, although currently unknown, has been attributed to a number of factors, including oxidant stress, mitochondrial toxicity, and autoimmunity. Olanow et al., in *Neurodegenetaion and Neuroprotection* (Academic Press: San Diego 1996).

There are currently a number of methods being used for treating Parkinson's disease, which can be grouped into two categories, namely chemical and surgical methods. Yahr et al. *Advances in Neurology* 60: 11–17 (1993). In chemical treatment methods, the goal is to achieve a stasis between the counterbalancing dopamine and acetylcholine neurotransmitters. Jankovic et al., in *Parkinson's Disease and Movement Disorders* 115–568 (Williams and Wilkins: Baltimore). The correct balance of the neurotransmitters produces a therapeutic effect in the Parkinson's disease patient. At least three methods of accomplishing or restoring a therapeutic balance are presently possible. First, in the dopaminergic method, a balance may be achieved by increasing deficient dopamine levels by using dopamine precursors or by increasing levels of dopamine agonists in the brain. Controlled release systems have been used to increase dopamine levels. Becker et al. *Brain Res.* 508:60 (1990); Sabel *Advances in Neurology*, 53:513–18 (1990). Second, monoamine oxidase inhibitors (MAO) reduce the rate of dopamine breakdown catalyzed by monoamine oxidase enzymes and thereby increase the dopamine levels in the brain. Third, anticholinergics block the receptor sites for acetylcholine in an attempt to compensate for low dopamine levels.

Currently, there are at least two surgical methods being utilized in Parkinson's therapy. Jankovic et al., supra. In ablative surgeries, a small portion of the globus pallidus (pallidotomy) or the thalamus (thalamotomy) is destroyed, which has been shown to be effective in treating Parkinson's disease. In tissue transplants, dopaminergic cells, such as fetal nigral primordia and adrenal chromaffin cells, are grafted into the basal ganglia region or striatum. Fetal dopaminergic neurons have been observed to provide superior functional recovery in terms of both magnitude and duration of effects. Kordower et al., in *Therapeutic Approaches To Parkinson's Disease* 443–72 (Roller et al. eds., Mercer Dekker Inc.: New York (1990)). This is true for both rodent and nonhuman primate models of Parkinson's disease as well as clinical trials in Parkinson's disease patients. Bakay et al. *Ann. NY Acad. Sci.* 495:623–40 (1987); Bankiewiez et al. *Progress in Brain Research* 78:543–50 (1988); Freed et al. *New England Journal of Medicine* 327:1549–55 (1992). In addition, such cells have been encapsulated, Emerich et al. *Neurosci. Behav. Rev.* 16:437–47 (1992), and found to alleviate symptoms of Parkinson's disease in rodents, Aebischer et al. *Brain Res.* 560:43 (1991); Lindner et al. *Exp. Neurol.* 132:62–76 (1995); Subramanian et al. *Cell Transplant* 6:469–77 (1997).

Although both chemical and surgical methods help to decrease the symptoms of Parkinson's disease, there are a number of areas requiring improvement. With respect to chemical methods, delivery to the striatal region of any biologically active agent, such as dopamine, MAO inhibitors, or anticholinergics, is complicated, in part, because of the presence of the blood-brain barrier, which may result in low bioavailability of any such agents. As an alternative, direct administration of dopamine into the central nervous system may require the frequent and repeated use of invasive procedures which compromise the integrity of the blood-brain barrier. Those techniques require repeated infusions into the brain, either through injections via cannulae, or from pumps which must be replaced every time the reservoir is depleted. Even with the careful use of sterile procedures, there is risk of infection. It has been reported that even in intensive care units, intracerebroventricular catheters used to monitor intracranial pressure become infected with bacteria after about three days. Saffran, *Perspectives in Biology and Medicine* 35:471–86 (1992). In addition to the risk of infection, there seems to be some risk associated with the infusion procedure. Infusions into the ventricles have been reported to produce hydrocephalus, Saffran et al. *Brain Research* 492:245–54 (1989), and continuous infusions of solutions into the parenchyma is associated with necrosis.

Because of the fact that dopamine itself does not readily cross the blood-brain barrier, many of the drug therapies utilize the dopamine precursor L-dopa. *Modern Pharmacology* 108 (2d ed, Craig et al. eds, 1986). Conversion of L-dopa to dopamine requires the enzyme amino acid decarboxylase, which is found in the substantia nigra of the brain. The progression of Parkinson's disease and the need for larger doses of L-dopa in order to produce therapeutic effects may be due to the loss of the enzyme required for this conversion.

This loss of therapeutic efficacy is known as long-term L-dopa syndrome and occurs in 3 to 5 years in 50% of Parkinson's disease patients being treated with L-dopa. Brannan et al. *Neurology* 45:596 (1991).

Surgical tissue transplantation suffers from a number of factors such as immunogenic complications, delayed improvement results, and low tissue survival rates of around 10%. The use of fetal tissue has formidable hurdles, including the failure to reestablish the normal neural circuitry, high mortality and morbidity associated with the transplant procedure, and the ethical issue of human fetal tissue research. Aebischer et al. *Transactions of the ASME* 113:178 (1991). Adrenal cells are generally only implanted in patients less than 60 years of age, as the adrenal gland of older patients may not contain sufficient dopamine-secreting cells, which limits the usefulness of the procedure as a treatment method because the disease most often affects the elderly. With respect to encapsulation of dopamine producing cells, questions remain concerning cell viability upon encapsulation and their resulting durability and output. Lindner et al. *Cell Transplant* 7:165–74 (1998).

Although the different therapies discussed above for Parkinson's disease have met with some success, there remains a need for additional treatment methods for the condition. In the present invention, in part, novel methods of producing the biologically active agent dopamine in the brain is contemplated. In another aspect, the present invention contemplates treating diseases or conditions by either producing or removing biologically active agents in a patient.

3. SUMMARY OF THE INVENTION

In one aspect, the present invention contemplates matrices encapsulating a reaction center, and methods of using the same.

In another aspect, the present invention is directed to methods for producing a biologically active agent from a prodrug involving encapsulating a cell-free reaction center in a biocompatible matrix and administering the matrix to a subject, wherein said reaction center converts a prodrug into a biologically active agent in the subject. In one method of the present invention, the matrices of the present invention are administered to a subject for treatment of a disease or condition by production or removal of a biologically active agent or agents.

In another aspect, the present invention involves methods of enzyme replacement therapy for treating a subject involving administering to the subject a reaction center which is encapsulated in a biocompatible matrix, wherein said reaction center replaces, augments, or supplements some activity in said subject. The reaction center may be an enzyme in which a subject to be treated is deficient, because of, for example, a disease or condition or an inborn error of metabolism.

In another aspect, the present invention contemplates methods for the extracorporeal use of the subject matrices in, for example, organ assist devices such as a liver assist device. In one method of the present invention, the matrices of the present invention are used ex vivo for treatment of a disease or condition by production or removal of a biologically active agent or agents from a patient.

In certain embodiments of the present invention, including the foregoing aspects, the reaction center may be an enzyme, an antibody, a catalytic antibody or other biological material. In other embodiments, the matrix may be an inorganic-based sol-gel matrix or a silica-based sot-gel matrix. More than one reaction center may be encapsulated in a single matrix. In addition to any encapsulated reaction center, the matrix may have encapsulated additives. In one preferred embodiment, the reaction center may be L-amino acid decarboxylase, the prodrug may be L-dopa and the biologically active agent may be dopamine.

In still another aspect, the matrices of the present invention, and methods of using the same, may be used in diagnostic applications, such as in certain embodiments in which an imaging agent is encapsulated therein.

In still another aspect, the matrices and compositions of the present invention may be used in the manufacture of a medicament for any number of uses, including for example treating any disease or other treatable condition of a patient. In still other aspects, the present invention is directed to a method for formulating (either separately or together) matrices, prodrugs and other materials and agents required for treatment in a pharmaceutically acceptable carrier.

In another aspect, this invention contemplates a kit including matrices of the present invention, and optionally instructions for their use. For example, in one embodiment, such kits include matrices and associated prodrug for treatment of a patient. Such kits may have a variety of uses, including, for example, imaging, diagnosis, therapy, vaccination, and other applications.

4. BRIEF DESCRIPTION OF THE DRAWINGS

FIG. 1: Enzymatic activity assay for a matrix containing β-Glucosidase.

FIG. 2: Substrate and product spectra for penicillinase assay.

FIGS. 3(a) and (b): Penicillinase activity assays showing (a) multiple assays of a single matrix and (b) a single assay performed on each of five matrices from one batch preparation.

FIG. 4: Change in absorbance at three hours as a function of the enzyme concentration added to the matrix during preparation.

FIG. 5: Yield of immobilized enzyme in penicillinase-containing sol-gel matrices (observed activity was calculated as the percentage of enzyme activity used in the preparation of the matrices).

FIG. 6. Activity of crushed and whole matrices containing penicillinase. FIGS. 6 and 7 both show data for five unique matrices assayed one time each.

FIG. 7: Penicillinase activity in whole monoliths and crushed matrices with points shown being the mean of five measurements (error bars +/− one standard deviation).

FIGS. 8(a) and (b): (a) Activity of penicillinase-containing matrices with varying surface areas, and (b) activity as a percentage of the activity added in preparation. Surface areas corresponding to the labeling in the graphs are: A=15.1 cm$^2$, B=39.2 cm$^2$, C=71.3 cm$^2$ and D=135 cm$^2$.

FIG. 9: Tyrosine decarboxylase activity assay; elapsed time since gel cast 19.5 h.

FIG. 10. Tyrosine decarboxylase activity assay of two identical 16 day old matrices, A and B, with comparison to C (same matrix composition aged 19 h, no cofactor present). Assay of A is performed in the absence of pyridoxal-5-phosphate (cofactor) while B is performed with cofactor present.

5. DETAILED DESCRIPTION OF THE INVENTION

5.1. Definitions

For convenience, the meanings of certain terms employed in the specification are provided below. The meanings for these terms, as those of skill in the art would understand them, should be read in light of the remainder of the specification for a full and complete understanding of the scope of the invention.

The term "additives" refers to compounds, materials, and compositions that may be included in a matrix along with a reaction center. An additive may be encapsulated in or on a matrix or attached to a matrix, either the interior or exterior, by some interaction, including a covalent one or adhesion of the additive to the matrix. Examples of additives include other molecules necessary for the conversion mediated by the reaction center, solid materials which serve as a framework for the matrix, etc.

The term "antibody" refers to a binding agent including a whole antibody or a binding fragment thereof which is reactive with a specific antigen. Antibodies can be fragmented using conventional techniques and the fragments screened for utility in the same manner as described above for whole antibodies. For example, F(ab)2 fragments can be generated by treating an antibody with pepsin. The resulting F(ab)2 fragment can be treated to reduce disulfide bridges to produce Fab fragments.

The term "biocompatible matrix" as used herein means that the matrix, upon implantation in a subject, does not elicit a detrimental response sufficient to result in the rejection of the matrix or to render it inoperable, for example through degradation. To determine whether any subject matrix is biocompatible, it may be necessary to conduct a toxicity analysis. Such assays are well known in the art. One non-limiting example of such an assay for analyzing a composition of the present invention would be performed with live carcinoma cells, such as GT3TKB tumor cells, in the following manner: various amounts of subject matrices are placed in 96-well tissue culture plates and seeded with human gastric carcinoma cells (GT3TKB) at 104/well density. The degraded products are incubated with the GT3TKB cells for 48 hours. The results of the assay may be plotted as % relative growth versus amount of matrices in the tissue-culture well. In addition, matrices of the present invention may also be evaluated by well-known in vivo tests, such as subcutaneous implantations in rats to confirm that they do not cause significant levels of irritation or inflammation at the subcutaneous implantation sites.

The term "biologically active agent" as used herein means any organic or inorganic agent that is biologically active, e.g., produces some biological affect in a subject.

The term "encapsulated reaction center" means a reaction center that is contained within or on a matrix. For example, an encapsulated reaction center may be immobilized somewhere in a silica matrix; alternatively, it may be attached to the interior or the surface of a matrix by some means other than physical confinement, such as by covalent bonds or adhesion. Alternatively, an encapsulated reaction center may be located on the surface of a matrix.

The term "enzyme" refers to any polypeptide that converts a prodrug into a biologically active agent. An enzyme may be isolated from naturally occurring sources, or it may be prepared by recombinant methods. An enzyme may be a fusion or chimeric protein of a polypeptide that converts a prodrug and another polypeptide. An enzyme may be a portion or a fragment of a full-length enzyme. An enzyme may be substantially purified, or only partially purified. Homologs, orthologs, and paralogs of an enzyme are also enzymes. For purposes of the present invention, an enzyme is not a catalytic antibody, a cell, or an organism.

"Homology" refers to sequence similarity between two polypeptides or between two nucleic acid molecules. Homology may be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40 percent identity, though preferably less than 25 percent identity, with the sequence to which it is being compared.

The term "immunoisolatory matrix" means that the matrix upon administration to subject minimizes the deleterious effects of the subject's immune system on the reaction center or other contents contained within the matrix.

The term "long-term, stable production of biologically active agent" as used herein means the continued production of a biologically active agent at a level sufficient to maintain its useful biological activity for periods greater than at least about one month, more preferably about two months, four months, six months, eight months, ten months, one year, one and a half years or more.

The term "matrix" means any material in which a reaction center has been encapsulated. For example, one type of matrix is a silica-based sol-gel matrix. Another example of a matrix is an inorganic-based sol-gel matrix. A matrix may have more than one type of reaction center encapsulated.

The term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The phrases "parenteral administration" and "administered parenterally" mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

A "patient" or "subject" to be treated by the present invention can mean either a human or non-human animal.

The phrase "pharmaceutically acceptable" is employed to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" means a pharmaceutically-acceptable material, composition or vehicle, such as a liquid or solid filler, diluent, excipient, solvent or encapsulating material, involved in carrying or transporting a prodrug, compound, material, or composition from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "prodrug" is intended to encompass compounds, materials, and compositions which are converted by an encapsulated reaction center into a biologically active agent. One means of converting a prodrug to a biologically active agent is by an enzyme-catalyzed reaction. A prodrug need not be biologically inactive itself; instead, to be a prodrug, a compound need only have some altered biological activity upon conversion by a reaction center. A prodrug may be either endogenous or exogenous to a subject. Also, many prodrugs produce more than one compounds upon certain types of conversion, and the term "biologically active agent" when used to refer the products of such a prodrug conversion is intended to encompass all of those products.

The term "reaction center" means any material or compound that may be encapsulated in a matrix and that converts or reacts a prodrug into a biologically active agent or reacts with a biologically active agent to, for example, degrade such agent. In certain embodiments, the reaction center may be an enzyme, a catalytic antibody, or a nonbiologically derived catalyst, such as those commonly used for organic synthesis. In certain embodiments, the reaction center may be prokaryotic or eukaryotic cells, such as bacteria, yeast, or mammalian cells, including human cells, or components thereof, such as organelles. In other embodiments of the present invention, the reaction center is substantially pure, i.e. 95%, 96%, 97%, 98% or 99% pure and therefore essentially cell-free or organism-free. Numerous examples of reaction centers are set forth below.

The phrases "systemic administration," "administered systemically," "peripheral administration" and "administered peripherally" mean the administration of a compound, drug or other material other than directly into the central nervous system such that it enters the patient's system and, thus, is subject to metabolism and other like processes, for example, subcutaneous administration.

The phrase "therapeutically effective amount" means that amount of a prodrug, biologically active agent, compound, material, or composition according to the present invention which is effective for producing some desired therapeutic effect. Because in certain embodiments of the present invention, a prodrug is converted into a biologically active agent by an encapsulated reaction center, it is necessary to consider this conversion in determining what may be a "therapeutically effective amount" of a prodrug. The amount can vary greatly according to the effectiveness of a matrix, prodrug, or biologically active agent, the age, weight, and response of the individual subject, as well as the nature and severity of the subject's symptoms. Accordingly, there is no upper or lower critical limitation upon the amount of the a matrix, prodrug, or biologically active agent. The required quantity to be employed of a matrix or prodrug in combination with a matrix in the present invention may readily be determined by those skilled in the art.

The terms "treating" or "method of treatment" (and variations thereof) is intended to encompass curing as well as ameliorating at least one symptom of a condition, deficiency, or disease.

The term "$ED_{50}$" means the dose of a drug, including, for example, a matrix or a combination of a matrix and prodrug, which produces 50% of a maximum response or effect. Alternatively, the dose which produces a pre-determined response in 50% of test subjects or preparations.

The term "$LD_{50}$" means the dose of a drug, including, for example, a matrix or a combination of a matrix and prodrug, which is lethal in 50% of test subjects.

The term "therapeutic index" refers to the therapeutic index of a drug, including, for example, a matrix or a combination of a matrix and prodrug, defined as $LD_{50}/ED_{50}$.

The term "heteroatom" as used herein means an atom of any element other than carbon or hydrogen. Preferred heteroatoms are boron, nitrogen, oxygen, phosphorus, sulfur and selenium.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, alkylaminos, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The term "aryl" refers to both substituted and unsubstituted aromatic rings. The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviation*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocycle" refer to 4- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, quinoline, pteridine, carbazole, carboline, phenanthridine, acridine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

The phrase "fused ring " is art recognized and refers to a cyclic moiety which can comprise from 4 to 8 atoms in its ring structure, and can also be substituted or unsubstituted, (e.g., cycloalkyl, a cycloalkenyl, an aryl, or a heterocyclic ring) that shares a pair of carbon atoms with another ring. To illustrate, the fused ring system can be a benzodiazepine, a benzoazepine, a pyrrolodiazepine, a pyrroloazepine, a furanodiazepine, a furanoazepine, a thiophenodiazepine, a thiophenoazepine, an imidazolodiazepine, an imidazoloazepine, an oxazolodiazepine, an oxazoloazepine, a thiazolodiazepine, a thiazoloazepine, a pyrazolodiazepine, a pyrazoloazepine, a pyrazinodiazepine, a pyrazinoazepine, a pyridinodiazepine, a pyridinoazepine, a pyrimidinodiazepine, or a pyrimidinoazepine.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

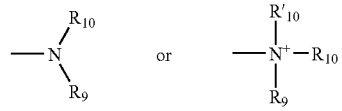

wherein $R_9$, $R_{10}$ and $R'_{10}$ each independently represent a hydrogen, an alkyl, an alkenyl, —$(CH_2)_m$—$R_{80}$, or $R_9$ and $R_{10}$ taken together with the N atom to which they are attached complete a heterocycle having from 4 to 8 atoms in the ring structure; $R_{80}$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_{80}$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

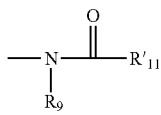

wherein $R_9$ is as defined above, and $R'_{11}$ represents a hydrogen, an alkyl, an alkenyl or —$(CH_2)_m$—$R_{80}$, where m and $R_{80}$ are as defined above.

The term "amido" is art recognized as an amino-substituted carbonyl and includes a moiety that can be represented by the general formula:

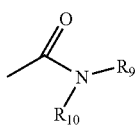

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_{80}$, wherein m and $R_{80}$ are defined above. Representative alkylthio groups include methylthio, ethylthio, and the like.

The term "carbonyl" is art recognized and includes such moieties as can be represented by the general formula:

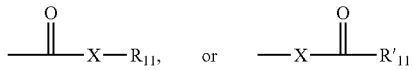

wherein X is a bond or represents an oxygen or a sulfur, and $R_{11}$ represents a hydrogen, an alkyl, an alkenyl, —$(CH_2)_m$—$R_{80}$ or a pharmaceutically acceptable salt, $R'_{11}$ represents a hydrogen, an alkyl, an alkenyl or —$(CH_2)_m$—$R_{80}$, where m and $R_{80}$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_{80}$, where m and $R_{80}$ are described above.

The terms "sulfoxido", as used herein, refers to a moiety that can be represented by the general formula:

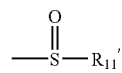

in which $R'_{11}$ is as defined above, but is not hydrogen.

A "sulfone", as used herein, refers to a moiety that can be represented by the general formula:

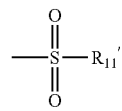

in which $R'_{11}$ is as defined above, but is not hydrogen.

The term "sulfonamido" is art recognized and includes a moiety that can be represented by the general formula:

in which $R_9$ and $R'_{11}$ are as defined above.

The term "sulfamoyl" is art-recognized and includes a moiety that can be represented by the general formula:

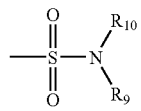

in which $R_9$ and $R_{10}$ are as defined above.

A "phosphoryl" can in general be represented by the formula:

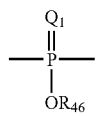

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

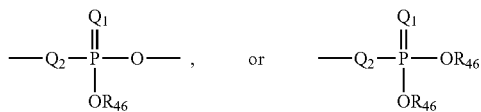

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidate" can be represented in the general formula:

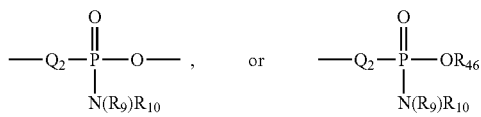

wherein $R_9$ and $R_{10}$ are as defined above, and $Q_2$ represents O, S or N.

A "phosphonamidate" can be represented in the general formula:

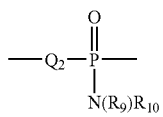

wherein $R_9$ and $R_{10}$ are as defined above, and $Q_2$ represents O, S.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, etc., when it occurs more than once in any structure, is intended to be independent of its definition elsewhere in the same structure.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivitization with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof, wherein one or more simple variations of substituents are made which do not adversely affect the desired use of the compound.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, hydrolysis, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

By the terms "amino acid residue" and "peptide residue" is meant an amino acid or peptide molecule without the —OH of its carboxyl group (C-terminally linked) or the proton of its amino group (N-terminally linked). In general the abbreviations used herein for designating the amino acids and the protective groups are based on recommendations of the IUPAC-IUB Commission on Biochemical Nomenclature (see *Biochemistry* 11:1726–1732 (1972)). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group. The term "amino acid side chain" is that part of an amino acid exclusive of the —CH(NH$_2$)COOH portion, as defined by Kopple, *Peptides and Amino Acids* 2, 33 W. A. Benjamin Inc., New York and Amsterdam, 1966; examples of such side chains of the common amino acids are —CH$_2$CH$_2$SCH$_3$ (the side chain of methionine), —CH(CH$_3$)—CH$_2$CH$_3$ (the side chain of isoleucine), —CH$_2$CH(CH$_3$)$_2$ (the side chain of leucine) or H— (the side chain of glycine).

For the most part, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan. However, the term amino acid residue further includes analogs, derivatives and congeners of any specific amino acid referred to herein. For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups. For instance, such amino acid analogs include β-cyanoalanine, canavanine, djenkolic acid, norleucine, 3-phosphoserine, homoserine, dihydroxyphenylalanine, 5-hydroxytryptophan, 1-methylhistidine, or 3-methylhistidine. Other naturally occurring amino acid metabolites or precursors having side chains which are suitable herein will be recognized by those skilled in the art and are included in the scope of the present invention.

Also included are the D and L stereoisomers of such amino acids when the structure of the amino acid admits of stereoisomeric forms. The configuration of the amino acids and amino acid residues herein are designated by the appropriate symbols D, L or DL, furthermore when the configuration is not designated the amino acid or residue can have the configuration D, L or DL. It will be noted that the structure of some of the compounds of this invention includes asymmetric carbon atoms. It is to be understood accordingly that the isomers arising from such asymmetry are included within the scope of this invention. Such isomers are obtained in substantially pure form by classical separation techniques and by sterically controlled synthesis. For the purposes of the present invention, unless expressly noted to the contrary, a named amino acid shall be construed to include both the D or L stereoisomers, preferably the L stereoisomer.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed. (Greene et al., *Protective Groups in Organic Synthesis*, 2$^{nd}$ ed.; Wiley: New York, 1991).

The phrase "N-terminal protecting group" or "amino-protecting group" as used herein refers to various amino-protecting groups which can be employed to protect the N-terminus of an amino acid or peptide against undesirable reactions during synthetic procedures. Examples of suitable groups include acyl protecting groups such as, to illustrate, formyl, dansyl, acetyl, benzoyl, trifluoroacetyl, succinyl and methoxysuccinyl; aromatic urethane protecting groups as, for example, carbonylbenzyloxy (Cbz); and aliphatic urethane protecting groups such as t-butyloxycarbonyl (Boc) or 9-Fluorenylmethoxycarbonyl (FMOC).

The phrase "C-terminal protecting group" or "carboxyl-protecting group" as used herein refers to those groups intended to protect a carboxylic acid group, such as the C-terminus of an amino acid or peptide. Benzyl or other suitable esters or ethers are illustrative of C-terminal protecting groups known in the art.

5.2. Uses

As a general introduction to the present invention, one way to appreciate certain aspects of the invention is by considering some of the different uses to which certain embodiments may be put. The rendition of these uses is for illustrative purposes only, and such categorization is not intended to limit the scope of the present invention. Other uses may be readily apparent to those of skill in the art, and other features of the present invention are presented below and may be applicable to any of the following uses. For all these uses, certain embodiments of the present invention may be used in animal models for assaying new treatments, e.g., new therapeutics or new treatment regimes.

5.2.1. Prodrug Activation

In one aspect of the present invention, embodiments of the present invention may be used as prodrug activators, that is, for prodrug activation. When used in this fashion, the reaction center encapsulated in a matrix reacts with a prodrug or prodrugs to produce a biologically active agent or agents. The prodrug may be exogenous to the subject, thereby requiring administration of the prodrug, or the prodrug may be endogenous to the subject, in which case administration of the prodrug to a subject may be used to add to the prodrug present in the subject, but is not absolutely necessary. For prodrug activation, one feature concerns matching the prodrug of interest with the reaction center encapsulated so that the reaction center may convert the prodrug into a biologically active agent. In general, the therapeutic effect of a matrix used for pending activation may vary greatly with its site of administration.

One related example of prodrug activation using exogenous sources involves ADEPT technology, or antibody directed enzymatic prodrug therapy, whereby an enzyme that converts a prodrug into a cytotoxic agent is attached to an antibody that is targeted to a antigen of interest, often a surface cell receptor of a neoplastic growth. See generally Denny et al. *J. Pharm. Pharmacol.* 50:387–94 (1998) and U.S. Pat. Nos. 6,015,556, 6,005,002, and 5,985,281. After binding of the antibody-enzyme conjugate to the antigen, prodrug is administered. The enzyme converts the exogenous prodrug into the cytotoxic agent in the vicinity of the neoplastic growth. In this fashion, ADEPT technology reduces toxicity to the subject because the cytotoxic agent is only produced in the immediate vicinity of the tumor. In gene-directed enzyme prodrug therapy (GDEPT), the exogenous enzyme is generated selectively in the tumor cells after delivery of a DNA construct containing the corresponding gene. The present invention contemplates relying on bystander effects and the like in the same fashion by administration, e.g., implantation, of the matrix in the vicinity of any neoplasm, whereupon administration of a prodrug causes conversion of that prodrug into a biologically active agent adjacent to the neoplasm. In contrast to ADEPT, the matrix may not be cleared from the subject as is often observed for the antibody-enzyme conjugate, so multiple administrations of prodrug using the present invention may be feasible. The present invention may also not result in nonspecific activation of the prodrug, which may occur using ADEPT if the antibody-enzyme conjugated binds indiscriminately or is not cleared by treatment with another antibody prior to administration of the prodrug.

Another illustrative report of prodrug activation using a exogenous source involved localized generation of 5-flurouracil from 5-fluorocytosine by surgically implanting immobilized cytosine deaminase adjacent to subcutaneous tumors in rats and injecting intraperitomeally 5-fluorocytosine. Nishiyama et al., *Cancer Res.* 45:1753–61 (1985). In this example, the implanted enzyme was encapsulated in a dialysis tube.

Embodiments of the present invention that may be grouped under this category involve the production of dopamine by a matrix, to which an example described below is directed. The biosynthesis of dopamine involves a number of enzymatic steps. One traditional treatment of Parkinson's disease uses an immediate precursor of dopamine, L dopa. Although L dopa therapy is effective in reducing Parkinson's symptoms, there is a lose of L dopa efficacy over time. One possible means of overcoming such a loss of efficacy involves increasing the enzymatic activity necessary to convert L dopa to dopamine. One enzyme that may be used in this regard is aromatic L-amino acid decarboxylase (AADC, E.C. 4.1.1.28). Cells stably expressing AADC have been grafted into 6-hydroxy-dopamine denervated rat striatum, and upon administration of L dopa, the dopamine content was observed to increase. Kaddis et al. *J. Neurochem.* 68:1520–26 (1997).

AADC catalzyes the irreversible decarboxylation reaction of several aromatic L-amino acids, including L-dopa, m-tyrosine, p-tyrosine, phenylalanine, 5-hydroxytryptophan, and tryptophan. Hayashi et al. *Biochemistry* 32:812–18 (1993); Dominici et al. *Eur. J. Biochem.* 169:209–13 (1987); Voltattorni et al. *Methods in Enzymology,* 142:179–87 (1987); Sourkes, *Methods in Enzymology,* 142:170–87 (1987); Lindstrom, *Biochem Biophys. Acta* 884:276–81 (1986); Jung *Bioorganic Chem.* 14:429–43 (1986); Nishigaki *Biochem. J.* 252:331–35 (1988). AADC is a pyridoxal phosphate dependent enzyme and is produced in the substantia nigral cells. Nigrastriatal cell death and concomitant decrease in AADC activity may result in decreased dopamine levels in the brain. Encapsulation of AADC as the reaction center and appropriate administration may allow for production of dopamine from L-dopa in the nigrastriatal region for treatment of Parkinson's disease.

It is possible that, by using this embodiment or related ones of the present invention, it may not be necessary to administer L-dopa to produce a therapeutic effect. Encapsulated enzymes may not require exogenous prodrug, e.g., administration of L-dopa, because L-dopa levels that occur naturally in a subject may be a sufficient source of dopamine upon conversion by the matrix. As a result, side effects of L-dopa administration common in present therapeutic treatments, including nausea, may be avoided. L-dopa therapy presently requires simultaneous administration of a peripheral decarboxylase inhibitor, such as carbidopa or benserazide, to reduce decarboxylation of L-dopa to dopamine outside the brain, which causes such nausea. Calne et al. *New Eng. J. Med.* 329:1021–27 (1993).

Although AADC is the enzyme responsible for L-dopa conversion to dopamine within the substantia nigra region of the brain, at least one additional enzyme is capable of effecting this conversion. L-Tyrosine decarboxylase (TD, E.C. 4.1.1.25) catalyzes the removal of the carboxyl group from tyrosine to produce tyramine and carbon dioxide. Pyridoxal 5'-phosphate is a necessary coenzyme. Although TD has greater specificity for decarboxylation of L-tyrosine to tyramine, TD also catalyzes decarboxylation of L-dopa. Maraques et al. *Plant Physiol,* 88: 46–51 (1988). Accordingly, TD may be encapsulated as the reaction center in a matrix of the present invention as a treatment method for Parkinson's disease.

In another approach to Parkinson's treatment using an embodiment of the present invention, an encapsulated reaction center may be used to produce a precursor of dopamine, such as L-dopa. Such a matrix would be similar to traditional L-dopa treatments, but in this case, L-dopa would be produced by the matrix only in the location where the matrix was administered. In this fashion, the matrix could be implanted so that L-dopa would be produced only in the brain. Consequently, there would probably be no side effects as reported for traditional L-dopa therapy. Tyrosine is converted to L-dopa by the enzyme tyrosine monooxygenase (TMO, E.C. 1.14.16.2). Encapsulation of TMO in a matrix and administration to the brain should increase L-dopa levels there. Tyrosine readily crosses the blood-brain barrier and would result in very little systematic toxicity. Tyrosine may or may not be necessary to administer to a subject to achieve the desired therapeutic effect.

In another embodiment of the present invention, it is possible to encapsulate both TMO and either AADC, TD, or both, in a matrix. By doing so, it would be possible for a single matrix to convert tyrosine to L-dopa, and L-dopa to dopamine. Because the decarboxylating enzyme, either AADC or TD, would be in close proximity to any L-dopa produced by the TMO, by virtue of both enzyme being encapsulated in the same matrix, conversion to dopamine readily proceed. Because tyrosine is less toxic than L-dopa, it may be desirable to use a matrix to effect two conversions, instead of just one. The present invention contemplates encapsulating more than one reaction center per matrix. Yamanka et al. *J. Sol-Gel Sci. & Tech.* 7:117–21 (1996).

In another embodiment, the enzyme monophenol monooxygenase (MMO E.C. 1.14.18.1), or tyosinase, is encapsulated as the reaction center. MMO is the key enzyme in melanin synthesis, catalyzing the first two steps of the pathway: dehydroxylation of L-tyrosine to L-dopa and oxidation of L-dopa to dopaquinone. The former reaction is termed cresolase activity, and the later reaction is termed catecholase activity. A number of assays have been used to measure the tyrosinase hydroxylase and dopa oxidase activities, including spectrophotometric, radiometric, HPLC and electrometric methods. Winder, *J. Biochem. Biophys. Methods* 28:173–83 (1994); Vachtenheum et al., *Analytical Biochem.* 146:405–10 (1985). MMOs from a number of different sources are known. Kenji Adachi et al. *Biochem. Biophys. Res. Comm.* 26 (1967); Seymour H. Pomerantz, *Tyrosinases (Hampster Melanoma)* 620–626; Duckworth et al., *J. Biol. Chem.* 245:1613–25 (1970); Steiner et al., *Analytical Biochem,* 238:72–75 (1996). Oxidation of o-diphenols to benzoquinones is referred to as catecholase activity. Although catecholase activity of MMO may reduce the production of the desired therapeutic L-dopa product, engineering of the sol-gel matrix may allow for increased production of the diphenol product. For example, it has been reported that administration of liposome-entrapped tyrosinase to rat increases levels of L-dopa in rat plasma. Miranda et al. *Gen. Pharmacol.* 24:1319–22 (1993). In the present invention, if the matrix is administered in the brain, then the increase in L-dopa would occur where it would have the greatest therapeutic effect.

In another aspect of the present invention, modulation of dopamine and related neurotransmitters may have use in treatment for cocaine addiction. See U.S. Pat. No. 5,189, 064. Chronic cocaine users may experience dopamine deficiency, and dopamine supplementation like that contemplated by the present invention may reduce the feeling of dysphoria inadequate stimulation attributable to depressed dopamine levels, which invites readministration of the drug or recividism.

In another aspect, the present invention contemplates applying the matrix-based technology to modulate the availability of any compounds by augmenting the enzymes found in the biological pathway for any such compounds. For example, tryptophan is converted into 5-hydroxy-tryptophan by the enzyme tryptophan hydroxylase with concomitant conversion of tertrahydrobiopterin to dihydrobiopterin. AADC then converts 5-hydroxy-tryptophan to serotonin, which is a neurotransmitter. Serotonin is found in the gastrointestinal tract and in the brain, where it is synthesized locally in the pineal gland. Monoamine oxidase converts serotonin into 5-hydroxy-indoleacetaldehyde, which aldehyde dehydrogeanse metabolizes into 5-hydroxy-indoleacetic acid. The present invention contemplate encapsulation any one or more of the enzymes in the serotonin pathway either to produce, as was discussed for the dopamine example discussed above, or to degrade serotonin in vivo as clinically necessary to treat any disease or condition. Thus, those of skill in the art may be able to use the present invention to modulate any biological pathway using enzymes of such pathway as reaction centers.

Some other possible enzymes, which may be useful in neuropharmacology and which may be used as reaction centers in the present invention, and the reaction that they catalyze, are listed below:

| Enzyme | Chief Reactant | Chief Product |
|---|---|---|
| Choline acetyltransferase | acetyl CoA + choline | CoA + o-acetylcholine |
| Phenylalanine 4-monooxygenase | L-phenylalanine | L-tyrosine |
| Dopamine β-monooxygenase | dopamine | norepinephrine (noradenaline) |
| Noradrenolin N-methyltransferase | noradrenalin | adrenaline (epinephrine) |
| Monoamine oxidase | norepinephrine | 3,4-dihydroxy-phenylglycolaldehyde |
| Catecholamine-O-methyl transferase (COMT) | norepinephrine | 3-O-methylnorepinephrine |
| Histidine decarboxylase | histidine | histamine |
| Histamine methyltransferase | histamine | 1-methylhistamine |
| Diamine oxidase | histamine | 5-imidazole acetic acid |
| Diamine oxidase | 1-methylhistamine | 1-methylimidazole acetic acid |
| L-Glutamic acid-1-decarboxylase | glutamate | γ-aminobutyric acid (GABA) |
| GABA-α-oxoglutarate transaminase | γ-aminobutyric acid (GABA) (plus α-oxoglutarate) | glutamate and succinic semialdehyde |
| Serine hydroxymethylase | L-serine | glycine |

See generally *Enzymes* (Dixon et al. eds; 3d ed. 1979).

In addition to these illustrative examples, the present invention contemplates providing any biologically active agents to treat a disease or condition. For example, in the nervous system, chronic, low-level delivery of trophic factors is sufficient to maintain the health of growth-factor dependent cell populations. In chronic disorders such as Alzheimer's disease and Huntington's disease, long-term delivery of one or more neurotrophic factors such as NGF, BDNF, NT-3, NT-4/5, CNTF, GDNF and CDF/LIF may be required to maintain neuronal viability. These growth factors cannot be delivered through systemic administration as they are unable to traverse the blood-brain barrier. Therefore, it may be necessary to deliver such neurotrophic factors into the central nervous system as a prodrug that is able to cross the blood-brain barrier. The present invention contemplates preparing prodrugs of such biologically active agents, and using an encapsulated reaction center to convert the prodrug into such an agent in the central nervous system. For example, CNTF is a potential therapeutic agent for Huntington's disease. Emerich et al. *Nature* 386:395–99 (1997). As discussed in more detail below, one of skill in the art could prepare a prodrug for CNTF so that a specific encapsulated reaction center would be capable of converting the prodrug to CNTF. As one example of such a matching between a prodrug and a reaction center, insulin may be obtained from recombinant proinsulin by reaction with carboxypeptidase or trypsin. Markvicheva et al. *App. Biochem. Biotechnol.* 61:75–84 (1996).

In certain embodiments of the present invention, an antibody may be encapsulated as the reaction center and the matrix administered to the subject. The matrix would be used to isolate deleterious biologically active agents from the subject in the matrix, as opposed to modifying as would a reaction center that reacts with such a biologically active agent. After all the antibodies have bound their corresponding hapten, the matrix may or may not be removed from the subject.

In certain embodiments matrices of the present invention may be used as prodrug activators in vivo after administration of the matrix and, if necessary, any prodrug, to a subject. Alternatively, the present invention contemplates using a matrix to convert a prodrug into a biologically active agent ex vivo, whereupon the biologically active agent is administered to a subject, as described in more detail in U.S. Pat. No. 5,378,232.

5.2.2. Enzyme Replacement, Augmentation, or Supplementation

In other aspects of the present invention, a reaction center is encapsulated in a matrix to replace or augment some lost biological activity that is generally present in a healthy subject, e.g., are without the disease or condition to be treated. Certain embodiments of the production of dopamine described above are examples of such replacement or augmentation. The encapsulated reaction center may restore or augment vital metabolic functions, such as the removal of toxins or harmful metabolites. Lost biological activity might result from loss of activity generally, or loss of activity in some location, e.g., a specific type of tissue. The loss may be attributable to a genetic defect, for example, an inborn error of metabolism, or may be caused by some disease or condition. If loss of function is complete, then this aspect of the invention may be referred to as enzyme replacement, whereas if loss of function is only partial, then this aspect of the invention may be referred to as enzyme augmentation. In other embodiments, although there has been no loss of enzyme function, enzyme augmentation may produce a desirable therapeutic effect. In other embodiments, the enzyme encapsulated is new to the subject, that is, there is supplementation. Through use of certain embodiments of the present invention, homeostasis of particular substances can be restored and maintained for extended periods of time.

Based on conditions and diseases that those of skill in the art know to result from loss of a particular enzymatic activity, reaction centers that replace or augment lost or diminished biological activity may be readily identified. Certain embodiments of the present invention have advantages over more conventional types of enzyme replacement therapy (ERT), which often rely on administration of an enzyme whose activity is lost or diminished. The matrices of the present invention for the most part may be biocompatible and immunoisolatory with respect to any encapsulated reaction center, whereas enzyme administration can result in hypersensitivity and/or anaphylactic reaction during or immediately after enzyme infusion. Brooks et al., *Biochem.*

*Biophys. Acta* 1497:163–72 (1998). The development of antibodies to any enzyme used in ERT may preclude its use in long-term therapeutic regimes or following relapses. Likewise, the present invention may avoid the need to dermitize an enzyme used in ERT with polyethylene glycol (PEG). Goldberg et al. *Biomedical Polymers* 441–52 (Academic Press 1980). Certain embodiments of the present invention, by encapsulating an enzyme as the reaction center, prevent degradation, and thereby may provide for prolonged treatment upon administration of the matrix. In contrast, for ERT, multiple infusions of the enzyme may be required for sustained therapy. Even erythrocyte-entrapped enzymes may show only modest increases in activity. See, for example, Thorpe et al. *Pediatr. Res.* 9:918–23 (1975).

By way of illustration, ERT has been used to treat Gaucher's disease. See generally Morales, *Ann. Pharmacother.* 30:381–88 (1996). Gaucher's disease is caused by a genetic deficiency of the enzyme glucocerebrosidase, and results in accumulation of glucocerebrosidase within the reticuloedothelial system. Symptoms include hepatosplenomegaly, bone marrow suppression, and bone lesions. There are three subtypes, of which the most common, type 1, is non-neuronopathic. Types 2 and 3, which are neuronopathic, may result in nerve cell destruction. Enzyme treatment first began with a placentally derived form of glucocerebrosidase, Dale et al. *Proc. Natl. Acad. Sci. USA* 73:4672–74 (1976), which has been replaced with a recombinant version of the enzyme. The enzyme treatment must be repeated every two weeks, and it has been effective in reducing hepatosplenomegaly, improving anemia and thrombocytopenia, and general health. Numerous studies have been completed on ERT for Gaucher's disease. Magnaldi et al., *Eur. Radiol.* 7:486–91 (1997); Ueda et al., *Acta Paediatr. Jpn.* 38:260–04 (1996); Lorberboym et al., *J. Nucl. Med.* 38:890–95 (1997); Charrow et al., *Arch Inter. Med.* 158:1754–60 (1998). The present invention contemplates encapsulation of this enzyme in a matrix and administration to a subject suffering from Gaucher's disease for treatment.

ERT has also been effected by using materials that act by slow release. For example, L-asparaginase has been loaded into nanoparticles composed of polymers that release the enzyme over a few weeks, or loaded into erythrocytes, Updike et al. *J. Lab. Clin. Med.* 101:679–91 (1983). The enzyme may be useful for treating cancer, especially acute lymphocytic leukemia. By encapsulating this enzyme as the reaction center in a matrix, the enzymatic activity may be present for longer periods than that made possible by using slow-release methods.

In another embodiment of the present invention, transport proteins such as hemoglobin may be encapsulated to produce an artificial red blood cell. In such an embodiment, the matrix must be of appropriate morphology to travel throughout the vasculature of a subject.

In addition to the examples already discussed, almost any naturally occurring enzyme may be used in to augment or replace enzymatic activity, and is therefore a candidate for this use. Some other possible enzymes that may be used as reaction centers, and the disease or condition that they may treat, are listed below. (These enzymes may be used to treat other diseases and conditions as well.)

| Enzyme | Disease or condition | Reference |
| --- | --- | --- |
| α-1,4-Glucosidase | Type II glycogenosis (Pompe's disease) | |
| α-Galactosidase | Fabry's disease (heart and kidney failure due to ceramide accumulation) | |
| α-L-iduronidase | mucopolysaccharidosis type I. | Kakkis et al. Biochem. Mol. Med. 58: 156–67 (1996) |
| β-glucuronidase | mucopolysaccharidosis type VII | O'Connor et al. J. Clin. Invest. 101: 1394–400 (1998) |
| Aminolaevulinate dehydratase | Lead poisoning | Bustos et al. Drug Des. Deliv. 5: 125–31 (1989) |
| Bilirubin oxidase | jaundice | |
| Catalase | Acatalasemia | |
| Fibrinolysin | Thromboembolic occlusive vascular disease | |
| Glutaminase (e.g., from *Pseudomonas putrefaciens*) | Cancer | |
| Hemoglobin | Respiratory | |
| Heparinase (e.g., from *Flavobacterium heparinum*) | Extracorporeal circulation | |
| L-arginine ureahydrolase (A1), Arginase | Hyperargininemia | Wissmann et al. Somot. Cell Mol. Genet. 22: 489–98 (1996) |
| Liver microsomal enzymes (e.g., from rabbit liver) | Liver failure | Brunner et al. Artif. Organs 3: 27–30 (1979); U.S. Pat. No. 5,849,588 |
| Phenylalanine ammonia lyase (e.g., from *Rhodotorula glutinis*) | Phenylketonuria | Bourget et al. Biochim Biophys Acta 883: 432–48 (1986) |
| Streptokinase (e.g., from *Streptococcus* sp.) | Thromboembolic occlusive vascular disease | |
| Superoxide dismutase (e.g., from bovine liver), catalase | Inflammatory diseases thought to be mediated by oxygen free radicals, e.g., bleomycin-induced lung fibrosis | Ledwozyw Acta Vet Hung 39: 215–24 (1991); Turrnes et al. J. Clin. Invest. 73: 87–95 (1984) |
| Terrilythin | Peritonitis | |
| Tyrosinase | Liver failure | |

-continued

| Enzyme | Disease or condition | Reference |
| --- | --- | --- |
| UDP Glucuronyl transferase (e.g., from rabbit liver) | Jaundice, liver disease | |
| Urea cycle enzymes | Liver failure | |
| Urease | Renal failure | |
| Uricase (e.g., from hog liver) | Hyperuricemia due to gout | |
| Urokinase (e.g., from human urine) | Thromboembolic occlusive vascular disease | |

See generally Klein et al. TIBTECH July, 1986, 179–86.

5.2.3. Addiction Neutralization

In another aspect of the invention, the encapsulated reaction center is chosen to degrade biologically active agents that may result in addiction. Efforts to combat addiction, e.g., cocaine addiction, have included inducing anti-drug antibodies specific to the drug. See generally U.S. Pat. No. 5,840,307. In certain embodiments, the present invention may help to neutralize the addiction, or in other words, cause addiction neutralization. For example, investigators have encapsulated alcohol dehydrogenase and/or acetaldehyde dehydrogeanse in human erthrocytes and reported the continuous degradation of ethanol for up to seventy hours. Lizano et al. *Biochem. Biophys. Acta* 1425:328–36 (1998). See also U.S. Pat. No. 5,759,539. Encapsulation of either or both of these enzymes in a matrix may allow for the complete metabolization of ethanol upon administration of the matrix, which would thereby combat addiction by neutralizing the addictive agent, ethanol.

In another example, catalytic antibodies have been elicited that are capable of aiding hydrolysis of the cocaine molecule. Landry et al. *Science* 259:1899–1901 (1993). See also U.S. Pat. No. 5,730,985. Encapsulation of such catalytic antibodies in a matrix of the present invention and administration to a subject addicted to cocain may allow for neutralization of any ingested cocaine. The present invention, by encapsulating the catalytic antibody, may avoid some of the drawbacks usually associated with passive antibody therapy. In the same fashion, reaction centers targeted at biologically active agents responsible for other types of addition are known to those of skill in the art, and may be used in a similar fashion.

5.2.4. Mutagenic Assays

In another aspect of the invention, the present invention contemplates using matrices as metabolic activating systems for use, for example, as toxicology screens for cytotoxic and pharmaceutical compounds in vivo. Such a use may reduce the need for laboratory animals for toxicology testing. Numerous efforts have been made to prepare human liver epithelian cell lines, and liver cell and tissue culture systems for such uses. See, for example, U.S. Pat. Nos. 5,849,588 and 5,759,765. In one report, enzymes responsible for deactivation of many endogenous toxins have been isolated and covalently bound onto a hemocompatible form of agarose support. Brunner et al., *Artif. Organs* 3:27–30 (1979). In a like manner, the present invention contemplates encapsulating such enzymes in matrices of the present invention and evaluating suspected mutagens. See generally Rueff et al *Mutat. Res.* 353:151–76 (1996). Enzymes usually found in the liver, such as cytochrome P-450 for example, may be used in this or related embodiments. Janig et al. *Acta Biol. Med. Ger.* 38:409–22 (1979).

5.2.5. Tissue Assist Devices

In addition to the many methods and uses described herein in which the subject matrices are administered for in vivo use, the matrices of the present invention may be used ex vivo. Many of the teachings herein described for in vivo use apply as well to ex vivo use (and visa-versa).

In one aspect of the present invention, one example of an ex vivo use is a tissue assist device, and in certain embodiments, an organ assist device. In such a device, matrices encapsulating one or more reaction centers could be used to replace, augment or supplement the biological function of an organ or other tissue. It is important to note that for this embodiment (and others described herein in which the prodrug converted by the reaction center is potentially deleterious to the subject being treated), it is not always necessary that the prodrug be converted into the same agent(s) that the enzymes and other catalysts usually present in the tissue would have were it to react with the prodrug. In certain embodiments of the subject invention, it is not the product of the prodrug that is critical; instead it is the transformation of the prodrug into a less toxic or otherwise undesirable compound(s) that is the primary concern. For example, this principle applies to certain of the embodiments used for addition neutralization described above as well as certain tissue assist devices.

One example of such an assist device is particularly well-suited to the subject matrices is an hepatic assist device. Liver transplantation has become widely accepted as an effective treatment for chronic and acute liver disease. One of the major problems associated with the transplantation process, however, as been the need for an effective means for providing temporary support for patients awaiting an available donor organ. Extracorporeal devices that are effective for liver support has proven more elusive. See, for example, Takahashi et al., *Digestive Diseases and Sciences* 36(9) (1991).

In certain embodiments of the present invention, one or more enzymes generally localized in the liver of a patient could be encapsulated in a subject matrix, and blood and other bodily fluids of the patient could be passed through and over these matrices ex vivo to augment the biological activity usually associated with the liver. Functions of the liver that could be addressed by such liver assist devices include, among others, carbohydrate, fat and protein metabolism and detoxification of drugs, hormones and other substances. At the point that the encapsulated reaction centers of the matrices are exhausted or otherwise less efficient than desired, they may be readily replaced by providing with new and more efficient matrices.

A variety of reaction centers could be encapsulated for such a liver assist device. Examples include cytochrome P-450, other enzymes usually located in the liver, a less than highly purified mixture of biologicals isolated from livers, transformed cells such as those derived from hepatoblastoma cell lines (Sussman et al., *Hepatology* 16:60–65 (1992)), cultured or isolated hepatocytes (U.S. Pat. No. 5,866,420; Rozga et al., *Hepatology* 17:258–65 (1993); Rozga et al., *Ann. Surg.* 217:502–11 (1994)), cells from hepatocarcinoma-derived cell lines (Richardson et al., *J. Cell Biol.* 40:236–47 (1969); Aden et al., *Nature (London)* 282:615–16 (1970)), Kupffer cells and other biologicals that are capable of replacing, augmenting or supplementing the biological function of the liver. For other examples of possible biologicals and liver assist devices, see, for example, U.S. Pat. Nos. 6,008,049, 5,849,588, 5,290,684, 5,270,192, 5,043,260, 4,853,324, 3,734,851; and WO 93/16171. Sources of suitable enzymes and biologicals for a livers assist device for humans include, for example, porcine and other mammals. In particular, use of certain biologicals, including for example hepatocytes, has proved difficult because their instability, and encapsulation of such biologicals in matrices of the present invention may improve their stability.

A variety of bioreactor techniques known to those of skill in the are could be used with such an assist device, including for example, hollow fiber techniques, static maintenance reactor systems, fluidized bed reactors, microporous membranes and flat-bed, single-pass perfusion systems. See, for example, U.S. Pat. Nos. 4,200,689, 5,081,035, 3,997,396; and WO 90/13639; Halberstadt et al., *Biotechnology and Bioengineering* 43:740–46 (1994).

In addition to liver assist devices, other organs or functions of a patient could be treated using matrices of the present invention ex vivo.

5.3. Matrices

The concept of encapsulating or immobilizing a reaction center in or on a matrix of some kind is well precedented. For example, significant efforts have been made to immobilize enzymes on solid supports. *Handbook of Enzyme Biotechnology* (2d ed., ed. Wiseman 1985). In these and other examples, encapsulation or immobilization of the reaction center may impart desirable characteristics on the reaction center.

A number of matrix chemistries that may be used in the present invention have been used to immobilize enzymes or biologically active agents. For instance, cells have been attached to glass beads and implanted in rats. Cherksey et al. *Neuroscience* 75:657–64 (1996). Reaction centers may be immobilized on a type of porous zirconia. Huckel et al., *J. Biochem. Biophys Methods* 31:165–79 (1996). Alternatively, reaction centers may be attached to supports through silane coupling. Weetall, *Appl. Biochem. Biotechnol.* 41:157–88 (1993). Biologics may be immobilized within a composite fibre by using a gel formation of cellulose derivative and metal alkoxide, e.g., titanium isopropoxide. Hatayama et al. *J. Sol-Gel Sci. & Tech.* 7:13–17 (1996); Ohmori et al. *J. Biotechnol.* 33:205–09 (1994). Poly(vinyl alcohol) synthetic polymer foams may be used. Li et al. *J. Biomater. Sci. Polm. Ed.* 9:239–58 (1998). Other polymers known in the art may be used. See, for example, U.S. Pat. Nos. 5,529,914 and 5,780,260; WO 93/16687. As described in greater detail below, inorganic-based or silica-based sol-gel matrices are contemplated by the present invention. Some examples of suitable inorganic-based matrices include those disclosed in the following references: Mazei et al., *J. Materials Chemistry* 8:2095–101 (1998); Yoldas, *J. Mater. Sci.* 1098–92 (1986); and Curran et al., *Chemistry of Materials*, 10:3156–66 (1998).

One feature of the matrix in certain embodiments of the present invention is its ability to prevent leaching of any encapsulated reaction center, at least to the extent necessary for the intended use of the matrix. In certain embodiments of the present invention, there may be negligible leaching. In others, there may be some leaching, but usually only a small amount over time. If leeching proses to be excessive, either the material to be encapsulated, e.g., a reaction center or an additive, or the sol-gel matrix may be modified to improve leaching characteristics, e.g., reduce leaching. For example, to reduce leaching, the reaction center may be derivatized to increase its size. For example, an enzyme may be chemically modified to create derivatives by forming covalent or aggregate conjugates with other chemical moieties, such as glycosyl groups, lipids, phosphate, acetyl groups, PEG, and the like. Covalent derivatives may be prepared by linking the chemical moieties to functional groups on amino acid sidechains of the protein or at the N-terminus or at the C-terminus of the polypeptide. Alternatively, a fusion or chimeric polypeptide retaining at least some of the activity of the enzyme may be used. Alternatively, the reaction center of additive may be attached to the sol-gel matrix in some fashion, e.g., by covalently bonding.

The manner in which a reaction center is encapsulated in a matrix, be it for example by physical entrapment, covalent attachment, or some other physical attraction, may affect the properties of such reaction center. For example, the micro environment around any covalently attached reaction center may differ from that encountered by the same reaction center encapsulated during gelation of the sol-gel, and any difference may affect the activity of the center. Thus, the present invention contemplates adjusting encapsulation, if necessary, for each intended use.

In preparing any matrix, the encapsulated material, e.g. the reaction center and additives, must be robust enough to retain their usefulness after being encapsulated. For example, many biological materials may not be able to survive the high temperatures and harsh conditions required to prepare some inorganic materials. Consequently, such inorganic materials may not be used with sensitive biolgicals. In the present invention, matrices are matched with the reaction center(s) or additive(s) to be encapsulated therein so as to retain sufficient activity of the reaction center.

Another feature of the present invention is the ability of the matrix to stabilize, in certain cases, the encapsulated reaction center. For example, the present invention may protect against degradation of any encapsulated biological material by naturally occurring systems, such as proteases. The matrix may protect against thermal denaturation of any encapsulated biological materials. Finally, the matrix may even assist in the correct re-folding of any denature polypeptide chain. Heichal-Segal et al. *Bio/Technology* 13:798 (1995).

5.3.1. Silica-Based Sol-Gel Matrices

In one aspect of the present invention, reactions centers are encapsulated in silica-based sol-gel matrices. Silica-based sol-gels have been applied to encapsulate a wide range of materials, including biological materials, small organic molecules, antibodies, antigens, and organic catalysts. See, for example, Ellerby et al. *Science* 255:1113–15 (1992); Dave et al. *Analytical Chem.* 66:1120–27 (1994); Avnir et al. *Acc. Chem. Res.*, 28:328–34 (1995); Avnir et al. *Chem. Mater.*, 6:1605–14 (1994) (listing encapsulated purified enzymes and whole-cell extracts and whole cells); *Biochemical Aspects of Sol-Gel Science and Technology* (eds. Avnir et al. 1996); Shtelzer et al. *Biotechnol. Appl. Biochem.*

15:227–35 (1992). Biological materials encapsulated in inorganic-based or silica-based sol-gel matrices have retained significant activity for a substantial time period.

Inorganic-based sol-gels, and in particular, silica-based sol-gels, have a variety of characteristics that are useful for encapsulation of reaction centers and implantation in vivo. See generally Dunn et al. *Acta Mater.* 46:737–41 (1998); Avnir et al. *Chem. Mater.*, 6:1605–14 (1994). Any or all of these features may or may not be present in particular embodiments of the present invention. Some such features include: stability to heat, light (no photodegredation), and electrical current (no electrochemical degradation); transparent in the visible region and into the UV-Vis region; controllable surface area and porosity (average pore size and pore size distribution); possibility of controlling conductivity by appropriate use of other inorganic alkoxides during preparation of the gel or addition of additives; capable of being readily modified chemically; improved stability of any encapsulated material, e.g., reaction center or additive, because of the rigid matrix; little or no leaching of any encapsulated material; readily manipulated in a variety of physical morphologies; and isolatory of any encapsulated material from the surrounding environment, except for any substance that is able to diffuse into the matrix. Many of these features are explained in greater detail below.

One area of interest involves using doped sol-gels as chemical sensors. As part of that effort, sol-gels have been used to encapsulate enzymes and antibodies. Avnir, *Acc. Chem. Res.*, 28: 328–334 (1995); Akbarian et al. *J. Sol-Gel Sci & Tech.* 8:1067–70 (1997). Immunosensors have been prepared using sol-gel technology. Wang et al. *Anal. Chem.* 15:1171–75 (1998). For example, the enzyme glucose oxidase has been examined upon encapsulation in a silica-based sol-gel matrix for use as a glucose sensing material. Yamanaka et al. *Chem. Mater.* 4:495 (1992); Audebert et al. *Chem Mater.* 5:911–13 (1993). Such sol-gel preparations have been used as electrodes for electrochemical assays of glucose concentrations. Sampath et al. *J. Sol-Gel Sci. & Tech.* 7:123–28 (1996).

Another area of interest of silica-based sol-gel technology has been encapsulating enzymes for use as organic catalysts in a variety of applications, including synthesis of chiral materials. Jaeger et al. *TIBTECH* 16:396–403 (1998).

Silica-based sol-gel matrices have also been used as controlled-release carriers of biologically active agents. See, for example, U.S. Pat. No. 5,849,331 and WO 97/45367.

(a) Preparation

Modifications in well-known sol-gel processes permit the incorporation of enzymes or other biologically derived reaction centers in silica-based sol-gel matrices. See generally Avnir et al. *Chem Mater.* 6:1605 (1994); U.S. Pat. Nos. 5,824,526, 5,650,311; 5,650,311; 5,371,018; 5,308,495; 5,300,564; 5,292,801.

Silica-based sol-gel matrices of the present invention may be prepared in the sol-gel method by polymerization of a metal alkoxide precursor. See generally Bruce Dunn et al. *Chem. Mater.*, 9:2280–91 (1997). The polymerization process is well documented and known to proceed by the formation of colloidal silica particles. A suspension of these particles is termed a sol. The synthesis generally involves the use of metal alkoxides which may undergo hydrolysis and condensation polymerization reactions. The preparation process can ordinarily be divided into the following steps: forming a solution, gelation, ageing, drying, and densification. In the preparation of a silica-based matrix, one starts with an appropriate alkoxide, for example, $Si(OC_2H_5)_4$, tetraethyl orthosilicate or TEOS, or $Si(OCH_3)_4$, tetramethyl orthosilicate or TMOS, which is mixed with water and a solvent, e.g., the alcohol of the alkoxide, ethanol or methanol, to form a solution. A number of reactions result, including hydrolysis, which leads to the formation of silanol groups Si—OH, and condensation, which gives siloxane Si—O—Si groups.

There are several parameters which influence the hydrolysis and condensation polymerization reactions, including the temperature, solution pH, particular alkoxide precursor and solvent, and relative concentrations of the alkoxide precursor, water, and solvent. Such parameters may be important to retaining activity when the reaction center encapsulated is an enzyme or other biological. For example, in encapsulating enzymes, greater enzyme activity may been preserved by not adding any alcohol at the start of polyermization. Another improvement may result from buffering the reaction solution to some pH suitable for any pH-sensitive materials to be encapsulated after the acid-catalyzed hydrolysis of the oxysilanes. Ellerby et al. *Science* 255:1113–15 (1992); Rietti-Shati et al. *J. Sol-Gel Sci. & Tech.* 7:77–79 (1996).

Initial hydrolysis of the precursor alkoxide is catalyzed by protons or hydroxide ions. It is possible to control the matrix characteristics by controlling the rates of the individual steps by which the matrix is condensed. Acidic catalysis tends to increase the rate of hydrolysis and disfavors the condensation reactions necessary to form the sol-gel, whereas base hydrolysis produces rapid condensation. If the reaction center to be encapsulated is not sensitive to pH conditions, the formation of the gel matrix can be achieved fairly rapidly. However, in the case of reaction centers or additives which may be sensitive to extreme pH conditions, such as enzymes, the pH of the sol must be adjusted prior to addition. Hence, preparation of the silica-based sol-gel may involve buffering the sol before the addition of the reaction center or other additives. For example, to retain the activity of bacteriorhodopsin, the solution was buffered to pH 9 after addition of the polypeptide. Weetall et al. *Biochem Biophys. Acta* 1142:211–13 (1993).

As the hydrolysis and condensation of polymerization reactions continue, viscosity increases until the solution ceases to flow. This sol-gel transition is irreversible, and at this stage the one-phase liquid is transformed to a two-phase system. The gel may consist of amorphous primary particles of variable size (5–10 nm or smaller) with an interstitial liquid phase. At this stage the pores have yet to shrink and the liquid phase fills the pores. After gelation, gels are generally subjected to an aging process during which the gels are sealed and very little solvent loss or shrinkage occurs. Condensation reactions continue, increasing the degree of cross-linking in the network.

The drying process involves the removal of the liquid phase. Ambient temperature evaporation may be employed, and there is considerable weight loss and shrinkage. It is at this stage that pore collapse may occur, deceasing pore size and thus decreasing the solvent volume. The combination of these effects causes an increase in the interaction between the reaction center and the matrix. The final stage of the sol-gel process is that of densification. It is at this point that the gel-to-glass conversion occurs and the gel achieves the properties of the glass. Matrices are found to contract to one eighth the pre-dried volume and are termed "xero-gels." The drying process may affect the accessibility of any encapsulated reaction center, and by adjusting such process, the present invention contemplates another means of influencing the activity of any encapsulated reaction center. Wamboldt et al. *J. Sol-Gel Sci & Tech* 7:53–57 (1996).

(b) Composition and Characteristics

Any number of alkoxide precursors may be used in preparing silica-based sol-gel matrices of the present invention. Those silica-based sol-gel matrices prepared from oxysilanes other than $Si(OR^1)_4$ are known as organically modified silica matrices, or Ormosil matrices. In preparing the matrices of the present invention, for example, alkoxides of the form $Si(OR^1)_4$, $R^2Si(OR^1)_3$, $R^2_2Si(OR^1)_2$, $R^2_3Si(OR^1)$ may be used, in which each $R^1$ is independently methyl, ethyl, or any lower-weight alkyl (although the identity of $R^1$ is usually the same in any type of oxysilane), and $R^2$ is independently any alkyl, aryl, or other substituent that does not interfere substantially with formation of the sol-gel, as discussed in more detail below. A significant difference between $R^1$ and $R^2$ is that the $R^1$ alkoxide the majority of $R^1$ is hydrolyzed during gelation, whereas the $R^2$ substituent remains part of the matrix. Because $R^2$ is not hydrolized but remains in the sol-gel matrix, the identity of $R^2$ may have a significant affect on the sol-gel matrix and any material encapsulated therein. In contrast, for $R^1$, much of which is hydrolized during gelation, may not constitute a significant percentage of the sol-gel matrix that results. Even so, the identity of $R^1$ may be important to the reaction, because $HOR^1$, which is produced upon hydrolysis of the oxysilane, may affect the formation of the sol-gel and any material encapsulated therein. Accordingly, for example, some biolgicals to be encapsulated may be stable to some $HOR^1$ and not others. In certain preferred embodiments, the alkoxide used is $Si(OR^1)_4$, in which $R^1$ is methyl or ethyl.

In certain embodiments, $R^2$ may contain functional groups. For example, aminopropyl, which has an amine functional group, and mercaptopropyl, which has a thiol functional group, have been used as $R^2$ in preparing sol-gel matrices from $R^2Si(OR^1)_3$ and mixtures of $R^2Si(OR^1)_3$ and $Si(OR^1)_4$, Collino et al. *J. Sol-Gel Sci. & Tech* 7:81–85 (1996); Venton et al. *Biochim Biophys Acta* 1250:117–25 (1995). Such sol-gel matrices were used to prepare thin films. Almost any chemical moiety may be used as $R^2$ in the present invention as long as any functional groups contained therein are not adverse to formation of the sol-gel matrix. For those functional groups that may not be compatible with the sol-gel chemistry, it may be possible to protect them using standard protection technologies know in the art of organic chemistry and then deprotect them after preparation of the sol-gel matrix is complete.

Functional groups may be used to increase the stability or reactivity of any encapsulated reaction center, especially when the reaction center is a biologic. For example, functional groups having hydrolizable functional groups, such a phenol or amine, may affect the local pH, thereby improving reactivity or stability of the encapsulated reaction center, or directly assist catalysis or stabilize an enzyme. Alternatively, functional groups may affect the characteristics of the surface of the matrix, which may affect the biocompatability of the matrix. In addition, by incorporating functional groups into the matrices of the present invention, the exterior characteristics of the matrix may be altered by derivitization. For example, chemical moieties, such as glycosyl groups, lipids, phosphate, acetyl groups, PEG, and the like, could be attached to the surface of the matrix though such functional groups.

In other embodiments of the present invention, $R^2$ may incorporate chemistry that allows for covalent attachment of any reaction center or additive directly to the sol-gel matrix. For example, a reaction center or additive could be covalently attached to the silicon of an oxysilane as $R^2$ through a linker bound to the silicon or other inorganic. Such a modified silica alkoxide could be reacted with nonsubstituted silica alkoxides to form the sol-gel of interest. In another embodiment, the moiety covalently attached to the silica alkoxide could be a biotin group, and the reaction center or additive could be attached to avidin. The biotin/avidin interaction would effectively attach the reaction center or additive to the silica oxide framework of any sol-gel matrix. An antibody/hapten pair could be used in the same fashion.

For certain embodiments, the alkoxide used may be a single silica alkoxide, or a mixture of silica alkoxides. Reetz et al. *J. Sol-Gel Sci. & Tech.* 7:35–42 (1996). When using silica oxides of structure $R^2Si(OR^1)_3$, $R^2_2Si(OR^1)_2$, $R^2_3Si(OR^1)$, it may be necessary to react them with sufficient $Si(OR_1)_4$ to allow for adequate gelation and formation of a physically robust matrix. For instance, the oxysilanes substituted with non-hydrolizable substituents may constitute 0.1, 1, 2, 5, 10, 15, 20, 25, 30, 40, 50, 60, 70, 80, 90, or 100 percent of the oxysilane used in the preparation. If a oxysilane has non-hydrolizable substituents, the percent of that oxysilane may need to be less to ensure sufficient gelation.

Modification of the framework of a silica-based sol-gel by variation of the precursor alkoxide presents the possibility of tailoring the microenvironment of the encapsulated reaction center. In this fashion, it is possible to, for example, maximize the reactivity of any encapsulated reaction center. Increasing the number of alkyl groups as well as increasing chain length of the alkyl groups in the precursor material may produce increased matrix hydrophobicity. Such hydrophobicity, for example, may be conducive to stabilization of the reaction center. The local pH within the sol-gel may also be affected by the chemical identity of the matrix. In one report, the activity of an encapsulated enzyme increased upon using a mixture of oxysilanes with various alkyl substituents. Reetz et al. *Angew. Chem. Int. Ed. Engl.* 34:301–303 (1995). By varying the chemical identity and ratio of different oxysilanes, the present invention contemplates customizing the sol-gel matrix for each encapsulated reaction center, e.g., to maximize catalytic activity. Other features of the matrix may depend on the chemical identity of the oxysilane precursors, for example wettability, which may affect the biocompatibility of any matrix upon implantation. For example, cell adhesion and growth may depend on the wettability of the matrix. Altankov et al. *J. Biomed. Mater. Res.* 30:385–91 (1996); Altankov et al. *J. Biomater. Sci. Polym. Ed.* 8:299–310 (1996).

Pore size is an important characteristic of any sol-gel matrix, because it may affect what materials, e.g., prodrugs, may diffuse in and out of the matrix, and the leachability of any encapsulated reaction center(s) and/or additive(s). A number of reports indicate that the pore size and/or shape may be varied by adjusting the synthetic conditions by which any material is encapsulated in a sol-gel. Dave et al. *ACS Symp. Ser.* 622:351 (1996). The present invention contemplates pore sizes ranging from the angstrom level to the micron level.

In addition to preparing silica-based sol-gel matrices from silica oxides, other oxides, including metal oxides, may be used to encapsulate a reaction center in inorganic-based sol-gel matrices. In one report, glucose oxidase was encapsulated within vanadium pentaoxide, and the resulting sol-gel was used in electrochemical studies. Glezer et al. *J. Am. Chem. Soc.*, 115:2533–34 (1993). A vanadium alkoxide has been co-condensed with TEOS, thereby imparting the properties, including reactivity, of oxovanadium(V) functional groups to the matrix. Stiegman et al. *Chem. Mater.* 5:1591–94 (1993). Oxysilines and other metal oxides may be combined in any sol-gel matrix. Silica-based sol-gel matrices in which redox active metal ions constitute part of the sol-gel framework may prove useful in promoting reactions involving electron transfers such as reductions and oxidations within the sol-gel itself. For example, an electron source foreign to the matrix may transfer an electron to a reaction center encapsulated in such a mixed metal sol-gel by electron transfer through a pathway involving the metal atoms in the framework of the sol-gel. Soghomonian et al. *Chem. Mater.* 5:1595–97 (1993).

The local environment, or micro-environment, immediately surrounding any encapsulated reaction center of the present invention may play an important role in affecting the capability of such reaction center to catalyze the conversion of prodrug to biologically active agent. A number of studies have been completed to better characterize the nature of the microenvironment around any encapsulated material in a sol-gel. Samuel et al. *Chem Mater.*, 6:1457–61 (1994); Zheng et al. *Anal Chem.* 69:3940–49 (1997); Dave et al. *J. Sol-Gl Sci & Tech.* 8:629–34 (1997); Avnir et al. *J. Phys. Chem.* 88:5956–59 (1984). By adjusting any of the variables delimited above, the properties of the silica-based sol-gel matrix may be readily tailored by one of skill in the art to the reaction center encapsulated.

5.3.2. Other Features of the Matrix

The matrix may be immunoisolatory with respect to the reaction center or other contents. Use of immunoisolatory matrices allows the implantation of alkogenetic or xenogeneic reaction centers and other additives, without a concomitant need to immunosuppress the subject. Using immunoisolatory matrices, it is possible to implant reactions centers that are foreign to the subject, such as nonmamallian enzymes, provided that critical substances necessary to the mediation of immunological attack are excluded from the implant. These substances may comprise the complement attack complex component Clq, or they may comprise phagocytic or cytotoxic cells; the instant immunoisolatory matrix protects against these harmful substances.

The present invention allows for coating or otherwise modifying the exterior of the matrix. Such a coating may render the matrix immunoisolatory. U.S. Pat. No. 5,676,943. For example, the coating or other modification may confer protection of the reaction center or other contents from the immune system of the host in whom the matrix is implanted, by providing a physical barrier sufficient to prevent detrimental immunological contact between the reaction center and other additives and the host's immune system. The thickness of a coating may vary, but it will always be sufficiently thick to prevent direct contact between the reaction center and the elements of the host's immune system. The thickness generally ranges between 5 and 200 microns; thicknesses of 10 to 100 microns are preferred, and thickness of 20 to 75 microns are particularly preferred. Types of immunological attack which can be prevented or minimized by the use of a coating or other modification include attack by macrophages, neutrophils, cellular immune responses (e.g. natural killer cells and antibody-dependent T cell-mediated cytoloysis (ADCC), and humoral response (e.g., antibody-dependent complement mediated cytolysis).

Various polymers and polymer blends can be used to manufacture a coating, including polyacrylates (including acrylic copolymers), polyvinylidenes, polyvinyl chloride copolymers, polyurethanes, polystyrenes, polyamides, cellulose acetates, cellulose nitrates, polysulfones, polyphosphazenes, polyacrylonitriles, poly(acrylonitrile/covinyl chloride), as well as derivatives, copolymers and mixtures thereof.

The solvents used in conjunction with the above-identified polymers in forming the coating will depend upon the particular polymer chosen. Suitable solvents include a wide variety of organic solvents such as alcohols and ketones generally as well as dimethylsulfoxide (DMSO), dimethylacetamide (DMA), and dimethylformamide (DMF) and blends of these solvents as well.

The coating may also include a hydrophobic matrix such as an ethylene vinyl acetate copolymer, or a hydrophilic matrix such as a hydrogel. The coating may be post-production coated or treated with an impermeable outer layer such as a polyurethane, ethylene vinyl acetate, silicon, or alginate.

The polymeric solution for the coating may also include various additives such as surfactants to enhance the formation of porous channels and antioxidants to sequester oxides that are formed during the coagulation process. Exemplary surfactants include Triton-X 100 available from Sigma Chemical Corp. and Pluronics P65, P32, and P18. Exemplary anti-oxidants include vitamin C (ascorbic acid) and vitamin E.

In addition, anti-inflammatory agents can also be incorporated into the coating to reduce immune response. Exemplary anti-inflammatory agents include corticoids such as cortisone and ACTH, dexamethasone, cortisol, interleukin-1 and its receptors and agonists, and antibodies to TGF, interleukin-1, or gamma-interferon. Alternatively, these materials may be added to the implant after formation by a post-coating or spraying process. For example, the implant could be immersed in a solution containing an anti-inflammatory agent.

Post-coating procedures can also be used to provide a protective barrier against immunogens and the like. For example, after formation, the matrix may be coated (e.g., by immersion, spraying or applying a flowing fluid, if applicable) with a surface protecting material such as polyethylene oxide or polypropylene oxide to inhibit protein interactions of the reaction centers of the matrix with entities of the subject. Other protective coatings include silicon and hydrogels such as alginates. Derivatives of these coating materials, such as polyethylene oxide-polydimethyl siloxane, may also be used.

The coating may be formed freely around the core without chemical bonding, or alternatively, the coating may be directly cross-linked to the material of the implant.

The present invention also allows for enclosing the matrix in a membrane. The membrane may allow for passage of substances up to a predetermined size but prevents the passage of larger substances. More specifically, the surrounding or peripheral region is produced in such a manner that it has pores or voids of a predetermined range of size. As a result, the vehicle is selectively permeable. The molecular weight cutoff (MWCO) selected for a particular coating will be determined in part by the use contemplated. Membranes useful in the instant invention are ultrafiltration and microfiltration membranes.

If necessary, the present invention also allows for modification or additions to be made to the matrix to support or strengthen the matrix. U.S. Pat. No. 5,786,216. For example, structural materials, such as a hollow tube or cylindrica support, may be encapsulated in the matrix to improve its compression strength, tensile strength, or other properties.

The present invention also allows for attachment of a tether to the matrix to make implantation, placement, or recovery of the matrix more facile. The present allow also contemplates altering the surface of the matrix, for example by encapsulating a structure that affects the surface of the matrix, as an aid in fixing the matrix upon implantation.

5.3.3. Additives

Additives may be encapsulated in the matrix in addition to any reaction center or centers. Such additives may be used to alter the properties of the matrix. Investigations show that the addition of low concentrations of organic molecules to sol-gels has very little effect on the network formation of the sol-gel. Dunn et al. *Chem. Mater* 9:2280–91 (1997).

For example, additives that may be used in the present invention include sodium fluoride and polyethylene glycol. The use of polyethylene glycol in place of any alcohol during condensation of the sol-gel matrix may improve enzymatic activity of the encapsulated enzyme. Likewise, sodium fluoride may be used and may improve enzymatic activity of the encapsulated enzyme. Avnir et al. *Chem. Mater.* 6:1605–14 (1994).

For example, additives may alter the porosity of the matrix. Alternatively, additives may be used to provide necessary reactants for any encapsulated reaction center. For example, coenzymes for a reaction center may be encapsulated along with the enzyme itself. For AADC and TD, a required cofactor is pyridoxal phosphate. Pyridoxal phosphate may be encapsulated directly during preparation of the sol-gel matrix. Alternatively, pyridoxal phosphate itself may be prepared in a slow release formulation, and the formulation encapsulated. See generally U.S. Pat. No. 5,759,582.

Alternatively, additives may improve the physical characteristics of the matrix, for example, for purposes of handling and administration of the material. As with the reaction center, additives may be physically encapsulated during the synthesis of the sol-gel, or they may be covalently attached to the matrix directly.

Another possible additive of the present invention allows for ready detection of the matrix after administration. In this fashion, the matrices of the present invention may also be used for diagnostic purposes. Thus an X-ray contrast agent, such as a poly-iodo aromatic compound, may be encapsulated in the matrix. Matrices according to the invention may also contain paramagnetic, superparamagnetic or ferromagnetic substances which are of use in magnetic resonance imaging (MRI) diagnostics. Thus, submicron particles of iron or a magnetic iron oxide may be encapsulated into the matrix to provide ferromagnetic or super paramagnetic particles. Alternatively, paramagnetic MRI contrast agents, which principally comprise paramagnetic metal ions, such as gadolinium ions, ligated by a chelating agent which prevents their release (and thus substantially eliminates their toxicity), may be encapsulated. Matrices of the present invention may also contain ultrasound contrast agents such as heavy materials, e.g. barium sulphate or iodinated compounds such as the X-ray contrast agents referred to above, to provide ultrasound contrast media.

5.3.4. Matrix Morphology

The matrices of the present invention may take any variety of morphologies. As a practical matter, the form of the matrix may initially be determined by the vessel in which the matrix is synthesized. Such matrices may subsequently be processed in order to produce matrices of desired morphology. The size of any matrix may depend on its intended use, and the present invention contemplates preparing matrices having dimensions of centimeters (1, 10, 100, 1000 cm), millimeters (1, 10, 100 mm), micrometers (1, 10, 100), nanometers (1, 10, 100), and picometers (0.01, 0.01, 1, 10, 100 pm). Alternatively, the size of a matrix may be referred to by mass, which the present invention contemplates may range anywhere from 1000 gm to 1 ng.

The matrix may be any configuration appropriate for providing sufficient activity of the encapsulated reaction center necessary for its intended use. Possible morphologies include cylindrical, rectangular, disk-shaped, patch-shaped, ovoid, stellate, or spherical. For use in a subject, a matrix of the present invention may provide, in at least one dimension, sufficiently close proximity of any reaction centers to the surrounding tissues of the subject, including the subject's bloodstream, in order to make any biologically active agent produced by the reaction center bioavailable.

If the matrix is to be retrieved after it is implanted, configurations which tend to prevent migration of the matrix from the site of implantation may be desirable; in contrast, if the matrix is intended to migrate throughout a patient, other morphologies, such as spherical capsules small enough to travel in the recipient's blood vessels, may be desirable. The degree of miniaturization of any matrix may affect mobility and localization of a matrix in a subject. Certain shapes, such as rectangles, disks, or cylinders may offer greater structural integrity.

The surface area of the matrix may be important for its use. A greater surface area may result in a greater observed activity with respect to any particular load of an encapsulated reaction center. In particular, small bead or sphere shaped materials ranging in size of radius from may be desirable because they have increased surface area as compared to other morphologies. In order to increase further the surface area of a matrix, a powder of the matrix may be desirable. It may be desirable to enclose a matrix, especially if the matrix is in powder form, in a capsule. See, for example, U.S. Pat. Nos. 5,653,975; 5,773,286.

It may be possible to control the size of any matrix by using the aqueous core of reverse cellular micellar droplets as host reactors for preparation of the matrix, as reported by Jain et al. *J. Am. Chem. Soc.* 120:11092–95 (1998) for a silica-based sol-gel matrix. The matrix particles prepared in such a fashion may be highly monodispersed and have a narrow size distribution. Other hollow spheres may be used to prepare matrices of similar dimensions. See for example Caruso et al. *Science* 282:1111–13 (1998), U.S. Pat. No. 5,770,416, Lu et al., *Nature* 398:223–26 (1999).

5.4. Reaction Centers

A wide variety of compounds or materials may be used as the reaction center in the present invention. In general, any compound or material that converts a compound into a biologically active agent may be encapsulated. Alternatively, in other embodiments, any compound or material that degrades a biologically active agent may be encapsulated. Alternatively, any compound or material exhibiting reactivity of interest may be encapsulated. Many possible reaction centers have already been described in setting forth some of the uses of the present invention.

Possible types of reaction centers contemplated by the present invention include, for example, enzymes, catalytic antibodies, antibodies, and non-biologically derived catalysts. Many reaction centers may be biologically derived. Numerous reports describe encapsulating enzymes in sol-gels, and such teachings may be of assistance in embodiments of the present inventions. Zink et al. *New J. Chem.*, 18:1109–15 (1994); Miller et al. *J. Non-Crystalline Solids.* 202:279–89 (1996); Ji et al. *J. Am. Chem. Soc.*, 720: 222–23 (1998); Braun et al. *J. Non-Crystalline Solids* 147&148: 739–43 (1992); Yamanaka et al. *Chem. Mater.* 4:497–500

(1992); Lin et al. *J. Sol-Gel Sci. & Tech.* 7:19–26 (1996). Catalytic antibodies have been encapsulated in sol-gel matrices and the resulting matrices used in either a batch-wise operation or in a continuous flow apparatus for preparative scale organic synthesis. Shabat et al. *Chem. Mater.* 9:2258–60 (1997). Optically active polypeptides have been encapsulated with retention of activity. For example, bacteriorhodopsin or mutated forms have been encapsulated in sol-gel matrices, which are optically transparent. Weetall et al. *Biochem Biophys. Acta* 1142:211–13 (1993); Wu et al. *Chem. Mater.* 5:115–20 (1993). Phycobiliproteins have also been encapsulated. Chen et al. *J. Sol-Gel Sci. & Tech.* 7:99–108 (1996). Antibodies against small organic antigens have been encapsulated within the sol-gel. Bronshtein et al. *Chem. Mater.* 9:2632–39 (1997); Turniansky et al. *J. Sol-Gel Sci. & Tech.* 7:135–43 (1996). Wang et al. *Chem. Mater.* 65:2671–75 (1993). Alternatively, antigens have been encapsulated. Roux et al. *J. Sol-Gel Sci. & Tech.* 8:663–66 (1997); Livage et al. *J. Sol-Gel Sci. & Tech.* 7:45–51 (1996). Biologics having novel magnetic properties, such as ferritin have been encapsulated. Lan et al. *J. Sol-Gel Sci. & tech.* 7:109–116 (1996). In certain embodiments, the reaction center encapsulated need not be substantially purified from its natural source. Bresslar et al. *J. Sol-Gel Sci. & Tech.* 7:129–33 (1996).

Cells and organisms have been encapsulated in silica-based sol-gel matrices. Peterson et al. *P.S.E.B.M.* 218: 365–69 (1998). Bacteria have been immobilized in sol-gel matrices to metabolize herbicides for environmental cleanups. Rietti-Shati et al. *J. Sol-Gel Sci. & Tech.* 7:77–79 (1996). In using cells in a subject, it may be important to accustom them to the implantation site before implantation to improve their viability. Differences in conditions such as glucose concentration, oxygen availability, nutrient concentrations, in vitro and in vivo may have an adverse affect on implantation of cells. See generally U.S. Pat. Nos. 5,550,050; 5,620,883.

In addition to biological reaction centers, a variety of other materials have been encapsulated in silica-based sol-gels. For example, organic fluorescent dyes and photochromic information recording materials have been encapsulated. Avnir et al. *J. Phys. Chem.* 88:5956–59 (1984); Avnir et al. *Journal of Non-Crystalline Solids*, 74:395–406 (1985); Levy et al., *Journal of Non-Crystalline Solids*, 113:137–45 (1989). It is also possible to entrap a reaction center in a sol-gel for use in organic catalysis. For example, lipases may be encapsulated in a sol-gel for use as a heterogeneous biocatalyst. Reetz et al. *Angew. Chem. Int. Ed. Engl.* 34:301–03 (1995).

For those embodiments of the present invention that involve administration of a sol-gel matrix to a subject, the reaction center encapsulated therein need not be native to the subject. The sol-gel matrix, as discussed above, may be immunoisolatory itself or modified to make it so.

Any number of different types of reaction centers may be encapsulated in a single matrix. By encapsulating more than type of reaction center in a single matrix, certain embodiments of the present invention may cause the conversion of one compound into a second and then into a third, and so on. Yamanka et al. *J. Sol-Gel Sci. & Tech.* 7:117–21 (1996); Chang et al. *Artif. Organs* 3:38–41 (1979). Such a result may be advantageous if, for example, the biological activity of the second compound is undesirable. Alternatively, it may be the case that it is the third compound that has a more valuable biological activity than the second. Encapsulating more than one reaction center may increase the activity of the second reaction center in any pathway. For instance, the local concentration of reactants for the second center may be increased because of the reactivity of the first center. Fossel et al. *Eur. J. Biochem.* 30:165–71 (1987). Alternatively, for example, if the first type of reaction center catalyzes an oxidation or reduction, the second type of reaction center could mediate electron transfer and thereby facilitate greater catalytic activity. For instance, the electron-transfer redox pair Cc:CcP complex has been encapsulated. Lin et al. *J. Sol-Gel Sci. & Tech.* 7:19–26 (1996).

In addition to reaction of the reaction center with a single other compound, e.g., a prodrug, the present invention also contemplates the reaction of more than one material with the encapsulated reaction center. For example, it has been shown that NADP (nicotinamide adenine dinucleotide phosphate ester) may react with the reaction center and another molecule. In one example, D-glucose-6-phosphate was converted by glucose-6-phosphate-dehydrogenase to a oxidized byproduct with the concomitant reduction of $NADP^+$ to NADPH. Yamanaka et al., *J. Am. Chem. Soc.* 117:9095–96 (1995). The types of reaction centers which may be encapsulated in a sol-gel, as contemplated by the present invention, thus includes those compounds or materials that react with more than one reactant. For example, many enzymes contemplated by the present invention for encapsulation require coenzymes in addition to any substrate.

One important characteristic of any encapsulated reaction center is the degree of loading of the matrix. For example, the degree of loading may affect the reactivity of a reaction center in the sol-gel matrix. It has been reported that the activity of trypsin appeared to decrease with increased loading levels. Levels of loading contemplated by the present invention include 0.001, 0.01, 0.1, 1, 3, 5, 10, 15, 20 weight percent reaction center(s) and/or any additives to the matrix.

In certain embodiments, the present invention contemplates using as a reaction center enzymes or other biological materials that are isolated from, or otherwise substantially free of other cellular proteins. The term "substantially free of other cellular proteins" (also referred to herein as "contaminating proteins") or "substantially pure or purified preparations" are defined as encompassing preparations the reaction center of interest having less than 20% (by dry weight) contaminating protein, and preferably having less than 5% contaminating protein. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

In certain embodiments, the present invention contemplates using for the reaction center human homologs of any of the enzymes or other biological materials described herein, as well as orthologs and paralogs (homologs) in other species. The term "ortholog" refers to proteins which are homologs via speciation, e.g., closely related and assumed to have common descent based on structural and functional considerations. Orthologous proteins function as recognizably the same activity in different species. The term "paralog" refers to genes or proteins which are homologs via gene duplication, e.g., duplicated variants of a gene within a genome. See also Fritch *Syst Zool* 19:99–113 (1970).

In certain embodiments, the present invention contemplates homologs of any naturally occurring enzymes. Further, the present invention contemplates modification of the structure of any enzyme to enhance therapeutic or prophylactic efficacy, or stability (e.g., ex vivo shelf life). Such modified peptides may be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry* (2nd ed., Stryer et al. eds. 1981). Whether a change in the amino acid sequence of a peptide results in a functional homolog to any naturally occurring enzyme (e.g., functional in the sense that the resulting polypeptide mimics the wild-type form) can be readily determined by assaying for activity. Polypeptides in which more than one replacement has taken place can readily be tested in the same manner.

This invention further contemplates a method for generating sets of combinatorial mutants of any nucleic acid encoding for an enzyme used as a reaction center, as well as truncation mutants, and is especially useful for identifying potential variant sequences (e.g. homologs) that are functional in modulating the enzymatic activity of interest. The purpose of screening such combinatorial libraries is, for example, to identify novel polypeptides that may convert prodrugs to biologically active agents. In certain embodiments, such novel polypeptides may convert prodrugs that naturally occurring enzymes do not, which may therefore allow a particular prodrug to be used in the present invention that otherwise would not have been possible. In other embodiments, the prodrug of interest is converted only by an encapsulated, novel polypeptide. As a result, no biologically active agent is produced in vivo except by the encapsulated reaction center of the matrix. Such a specificity difference may have value because prodrugs that become cyotoxic agents may have reduced toxicity if they are stable in vivo. Site-directed mutagenesis has been used in ADEPT to prepare mutants of carboxypeptidase A, so that only the mutants and no naturally occurring enzyme converts selected prodrugs into corresponding cytotoxic agents. Smith et al. *J. Biol. Chem.* 272:15804–16 (1997). Even a single amino acid change may be sufficient to affect the specificity. Thus, combinatorially-derived homologs can be generated to have an increased potency or different specificity relative to a naturally occurring form of an enzyme or other biological macromolecule.

In one aspect of this method, the amino acid sequences for a population of homologs for any enzyme, or other related proteins, are aligned, preferably to promote the highest homology possible. Such a population of variants can include, for example, homologs from one or more species. Amino acids which appear at each position of the aligned sequences are selected to create a degenerate set of combinatorial sequences. In a preferred embodiment, the variegated library of variants is generated by combinatorial mutagenesis at the nucleic acid level, and is encoded by a variegated gene library. For instance, a mixture of synthetic oligonucleotides can be enzymatically ligated into gene sequences such that the degenerate set of potential sequences are expressible as individual polypeptides, or alternatively, as a set of larger fusion proteins containing the set of sequences therein.

There are many ways by which such libraries of potential homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential sequences. The synthesis of degenerate oligonucleotides is well known in the art. See, for example, Narang *Tetrahedron* 39:3 (1983); Itakura et al. *Recombinant DNA, Proc* 3rd Cleveland Sympos. Macromolecules 273–89 (ed. A G Walton, Amsterdam: Elsevier 1981); Itakura et al. *Annu. Rev. Biochem.* 53:323 (1984); Itakura et al. *Science* 198:1056 (1984); Ike et al. *Nucleic Acid Res.* 11:477 (1983). Such techniques have been employed in the directed evolution of other proteins. See, for example, Scott et al. *Science* 249:386–90 (1990); Roberts et al. *PNAS* 89:2429–33 (1992); Devlin et al. *Science* 249: 404–06 (1990); Cwirla et al. *PNAS* 87:6378–82 (1990); as well as U.S. Pat. Nos. 5,223,409, 5,198,346, and 5,096,815.

Likewise, a library of coding sequence fragments can be provided for an enzyme of interest as a reaction center in order to generate a variegated population of fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of an coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of homologs for any enzyme of interest as a reaction center. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

5.4.1. Enzymes Used for ADEPT

Enzymes that have been used for ADEPT may generally be used as the encapsulated reaction center in the present invention. Such enzymes were originally chosen because they convert a prodrug into a biologically active agent, and they are thereby of use in the present invention as well. Some examples of such enzymes, and the conversion that they catalyze, follow. Other examples may be found in U.S. Pat. Nos. 5,714,148; 5,660,829; 5,587,161; and 5,405,990. In the present invention, enzymes used in ADEPT need not necessarily be used with the same prodrug as used in the ADEPT application.

In one aspect of the invention, a variety of peptidases, which cleave amide bonds, may be used as the reaction center. Jungheim et al., *Chem. Rev.* 94:1553–66 (1994). In one embodiment, carboxypeptidase G2 can be used as the reaction center with prodrugs to cleave an amide bond. One biologically active agent is nitrogen mustard, which is an alkylating agent. Carboxypeptidase G2 cleaves an amide bond of a prodrug to give the free nitrogen mustard and glutamic acid. Bagshawe, *Br. J. Cancer* 56:531 (1987); Bagshawe et al. *Br. J. Cancer* 58:700 (1988). In another embodiment, carboxypeptidase A from bovine pancrease can be used as the reaction center with prodrugs to cleave an amide bond. In one embodiment, the biologically active agent is methotrexate, which is used for cancer chemotherapy, and the prodrugs are α-peptides of methotrexate, e.g., Glu-α-L-Ala-methotrexate and L-Glu-L-Phe-methotrexate. Vitols et al., *Pteridines* 3:125 (1992); Kuefner et al., *Biochem.* 28:2288 (1989); Haenseler et al., *Biochem.* 31:891 (1992).

In another embodiment, penicillin V amidase from *Fusarium oxysporum* can be used as the reaction center with prodrugs to deacylate an N-acyl amine. In several embodiments, the biologically active agent is doxorubicin or mephalan, which are anticancer agents, and the prodrugs are N-acyl derivatives of doxorubicin or mephalan. Kerr et al. *Cancer Immun. Immunother.* 31:202 (1990). In another embodiment, penicillin G amidase can be used as the reaction center with prodrugs to cleave phenylacetamides. In several embodiments, the biologically active agent is doxorubicin or mephalan, and the prodrugs are phenylacetamide derivatives of doxorubicin or mephalan. Kerr et al. supra. In another embodiment, the biologically active agent is palytoxin, which is a potent cytotoxin, and the prodrug is N-[(4'-hydroxyphenyl)acetyl] palytoxin. Because palytoxin asserts its effect extracellularly, it may be able to overcome the multidrug resistance phenotype.

In another embodiment, urokinase may be the reaction center. Puromycin and doxorubicin have been produced using this enzyme. WO 91/09134. In another embodiment, a variety of β-lactamases, which cleave certain amide bonds, may be used as the reaction center. In one embodiment, a biologically active agent is produced by covalently attaching the agent to the C-3' position of cephalosporin or a derivative of cephalosporin, whereupon hydrolization of the prodrug by a β-lactamase, e.g., P99 enzyme derived from *Enterobacter cloacae* 265A or enzyme derived from *B. cereus*, produces the free agent. Biologically active agents that have been covalently attached to cephalosporin or a derivative of cephalosporin in this manner include: methotrexate; 5-fluorouracil, which is often used for the treatment of colon cancer; LY233425, a potent analogue of the anticancer agent vinblastine; desacetylvinblastine hydrazine, a potent vinca alkaloid; nitrogen mustard alkylating agents; thioguanine; doxorubicin; mitomycin C; and DACCP, a carboplatinum-based drug that is a potent antitumor agent. Jungheim et al. *Chem. Rev.* 94:1553–66 (1994); Meyer et al. *Antibody, Immunoconjugates, Radiopharm.* 3:66 (1990); Jungheim et al., *Antibody, Immunoconjugates, Radiopharm.* 4:228 (1991); Shepard et al., *Biomed. Chem. Lett.* 1:21 (1991); EP0382411A2; Alexander et al. *Tetrahedron Lett.* 32:3269 (1991); EPo392745A2; Svensson et al. *Bioconj. Chem.* 3:176 (1992); Vrudhula et al. *Bioconj. Chem.* 4:334 (1993); Hudyma et al. *Biomed. Chem. Lett.* 3:323 (1993); EP0484870A2; Junghein et al. *Heterocycles* 35:33 (1993); Hanessian et al. *Can J. Chem.* 71:896 (1993).

In another aspect of the invention, alkaline phosphotase can be used as the reaction center with prodrugs to remove phosphate from organic phosphates. Biologically active agents that are produced in this manner include etoposide, mitomycin-derived agents, nitrogen mustard derived agents, and doxorubicin. Senter et al. *Proc. Nat. Acad. Sci. U.S.A.* 85:4842 (1988); Senter et al. *Cancer Res.* 49:5789 (1989); Senter, *FASEB J.* 4:188 (1990); Sahin et al. *Cancer Res.* 50:6944 (1990).

In another aspect of the invention, glycosidases, which cleave a glycosidic linkage may be used as the reaction center. In one embodiment, β-glucuronidase is used as the reaction center to produce biologically active agents, including nitrogen mustard derived agents, daunomycin, adriamycin, epirubicin. Roffler et al. *Biomed Pharmacol.* 42:2062 (1991); Wang et al. *Cancer Res.* 52:4484 (1992); Deonarain et al. *Br. J. Cancer* 70:786–94 (1994). In another embodiment, β-Glucosidase converts amygdalin into glucose, benzaldehyde, and hydrogen cyanide, a toxic species. In another embodiment, α-galactosidase is used as the reaction center to produce daunorubicin. Andrianomenjanahary et al. *Biomed. Chem. Lett.* 2:1093 (1992).

In another aspect of the invention, cytosine deaminase, which converts cytosine into uracil, may be used as the reaction center. In one embodiment, cytosine deaminase isolated from Bakers' yeast is used to produce the antitumor agent 5-fluroruracil from 5-fluorocytosine. Senter et al. *Bioconj. Chem.* 2:447 (1991). In another aspect of the invention, nitroreductase, which requires the presence of a cofactor such as NADH, may be used as the reaction center. The enzyme has been used to produce 5-aziridin-4-hydroxyamino-2-nitrobenzamide from 5-aziridin-2,4-dinitrobenzamide. Knox et al. *Cancer Metathesis Rev.* 12:195 (1993).

In another aspect of the invention, oxidases, which produce reduced oxygen species, e.g., peroxide, superoxide, and hydroxyl radicals, may be used as the reaction center. In one embodiment, glucose oxidase and lactoperoxidase convert glucose and iodide into hydrogen peroxide and toxic iodine species. Ito et al. *Bone Marrow Transplant.* 6:395–98 (1990); Stanislawski (1989). In another embodiment, xathine oxidase produces reduced oxygen species from either xanthine or hypoxanthine. Dinota et al. *Bone Marrow Transplant.* 6:31–36 (1990).

5.4.2. Other Enzymes

In addition to the enzymes used for ADEPT, for which a prodrug may have already been identified, other enzymes may be used as the reaction center. In using any enzyme in the present invention, it may be necessary to consider which compounds will be converted by the enzyme. Which enzyme is most suitable for encapsulation as the reaction center depends, in part, on the expected use of any matrix.

In deciding which enzyme may be appropriate for any application, the general classification of enzymes may be used in identifying and considering different types of reactions that a reaction center could possibly catalyze. These classes include: (i) oxidoreductases (acting on the CH—OH group of donors; acting on the aldehyde or oxo group of donors; acting on the CH—CH group of donors; acting on the CH—NH(2) group of donors; acting on the CH—NH group of donors; acting on NADH or NADPH; acting on other nitrogenous compounds as donors; acting on a sulfur group of donors; acting on a heme group of donors; acting on diphenols and related substances as donors; acting on a peroxide as acceptor (peroxidases); acting on hydrogen as donor; acting on single donors with incorporation of molecular oxygen; acting on paired donors with incorporation of molecular oxygen; acting on superoxide radicals as acceptor; oxidizing metal ions; acting on —CH(2) groups; acting on reduced ferredoxin as donor; acting on reduced flavodoxin as donor; other oxidoreductases); (ii) transferases (transferring one-carbon groups; transferring aldehyde or ketone residues; acyltransferases; glycosyltransferases; transferring alkyl or aryl groups, other than methyl groups; transferring nitrogenous groups; transferring phosphorous-containing groups; transferring sulfur-containing groups; transferring selenium-containing groups); (iii) hydrolases (acting on ester bonds; glycosidases; acting on ether bonds; acting on peptide bonds (peptide hydrolases); acting on carbon-nitrogen bonds, other than peptide bonds; acting on acid anhydrides; acting on carbon-carbon bonds; acting on halide bonds; acting on phosphorus-nitrogen bonds; acting on sulfur-nitrogen bonds; acting on carbon-phosphorus bonds; acting on sulfur-sulfur bonds); lyases (carbon-carbon lyases; carbon-oxygen lyases; carbon-nitrogen lyases; carbon-sulfur lyases; carbon-halide lyases; phosphorus-oxygen lyases; other lyases); (iv) isomerases (racemases and epimerases; cis-trans-isomerases; intramolecular oxidoreductases; intramolecular transferases (mutases); intramolecular lyases; other isomerases); (v) ligases (forming carbon-oxygen bonds; forming carbon-sulfur bonds; forming carbon-nitrogen bonds; forming carbon-carbon bonds; forming phosphoric ester bonds).

Illustrative examples of enzymes that may serve as reaction centers in the present invention include, without limitation: alcohol dehydrogenase (EC 1.1.1.1), homoserine dehydrogenase (EC 1.1.1.3), (R,R)-butanediol dehydrogenase (EC 1.1.1.4), glycerol dehydrogenase (EC 1.1.1.6), glycerol-3-phosphate dehydrogenase (NAD+) (EC 1.1.1.8), D-xylulose reductase (EC 1.1.1.9), L-xylulose reductase (EC 1.1.1.10), L-iditol dehydrogenase (EC 1.1.1.14), mannitol-1-phosphate dehydrogenase (EC 1.1.1.17), myo-inositol 2-dehydrogenase (EC 1.1.1.18), aldehyde reductase (EC 1.1.1.21), quinate dehydrogenase (EC 1.1.1.24), shikimate dehydrogenase (EC 1.1.1.25), glyoxylate reductase (EC 1.1.1.26), L-lactate dehydrogenase (EC 1.1.1.27), D-lactate dehydrogenase (EC 1.1.1.28), glycerate dehydrogenase (EC 1.1.1.29), 3-hydroxybutyrate dehydrogenase (EC 1.1.1.30), 3-hydroxyisobutyrate dehydrogenase (EC 1.1.1.31), 3-hydroxyacyl-CoA dehydrogenase (EC 1.1.1.35), malate dehydrogenase (EC 1.1.1.37), malate dehydrogenase and aspartate aminotransferase (EC 1.1.1.37 & 2.6.1.1), malate dehydrogenlase and citrate (si)-synthase (EC 1.1.1.37 and 4.1.3.7), malate dehydrogenase (decarboxylating) (EC 1.1.1.39), malate dehydrogenase (oxaloacetate-decarboxylating) (NADP+) (EC 1.1.1.40), isocitrate dehydrogenase (NADP+) (EC 1.1.1.42), phosphogluconate dehydrogenase (decarboxylating) (EC 1.1.1.44), glucose dehydrogenase (EC 1.1.1.47), galactose dehydrogenase (EC 1.1.1.48), glucose-6-phosphate dehydrogenase (EC 1.1.1.49), glucose-6-phosphate dehydrogenase and 6-phosphogluconolactonase (EC 1.1.1.49 & 3.1.1.31), 3-hydroxysteroid dehydrogenase (EC 1.1.1.50), 3(or 17)-hydroxysteroid dehydrogenase (EC 1.1.1.51), lactaldehyde reductase (NADPH) (EC 1.1.1.55), ribitol dehydrogenase (EC 1.1.1.56), 3-hydroxypropionate dehydrogenase (EC 1.1.1.59), 2-hydroxy-3-oxopropionate reductase (EC 1.1.1.60), 4-hydroxybutyrate dehydrogenase (EC 1.1.1.61), estradiol 17-dehydrogenase (EC 1.1.1.62), mannitol dehydrogenase (EC 1.1.1.67), gluconate 5-dehydrogenase (EC 1.1.1.69), glycerol dehydrogenase (NADP+) (EC 1.1.1.72), glyoxylate reductase (NADP+) (EC 1.1.1.79), aryl-alcohol dehydrogenase (EC 1.1.1.90), phosphoglycerate dehydrogenase (EC 1.1.1.95), diiodophenylpyruvate reductase (EC 1.1.1.96), 3-hydroxybenzyl-alcohol dehydrogenase (EC 1.1.1.97), 3-oxoacyl-[acyl-carrier-protein] reductase (EC 1.1.1.100), carnitine dehydrogenase (EC 1.1.1.108), indolelactate dehydrogenase (EC 1.1.1.110), glucose dehydrogenase (NADP+) (EC 1.1.1.119), fructose 5-dehydrogenase (NADP+) (EC 1.1.1.124), 2-deoxy-D-gluconate dehydrogenase (EC 1.1.1.125), L-threonate dehydrogenase (EC 1.1.1.129), sorbitol-6-phosphate dehydrogenase (EC 1.1.1.140), 15-hydroxyprostaglandin dehydrogenase (NAD+) (EC 1.1.1.141), 21-hydroxysteroid dehydrogenase (NAD+) (EC 1.1.1.150), sepiapterin reductase (EC 1.1.1.153), coniferyl-alcohol dehydrogenase (EC 1.1.1.194), (R)-2-hydroxyglutarate dehydrogenase (EC 1.1.1.a), sorbitol-6-phosphate dehydrogenase (NADP+) (EC 1.1.1.b), gluconate 2-dehydrogenase (EC 1.1.99.3), lactate-malate transhydrogenase (EC 1.1.99.7), glucoside 3-dehydrogenase (EC 1.1.99.13), formate dehydrogenase (EC 1.2.1.2), acetaldehyde dehydrogenase (acetylating) (EC 1.2.1.10), aspartate-semialdehyde dehydrogenase (EC 1.2.1.11), glyceraldehyde-3-phosphate dehydrogenase (EC 1.2.1.12), glyceraldehyde-3-phosphate dehydrogenase and phosphoglycerate kinase (EC 1.2.1.12 & 2.7.2.3), glyoxylate dehydrogenase (acylating) (EC 1.2.1.17), formate dehydrogenase (NADP+) (EC 1.2.1.43), succinate dehydrogenase (EC 1.3.99.1), butyryl-CoA dehydrogenase (EC 1.3.99.2), dihydroorotate dehydrogenase (EC 1.3.99.11), alanine dehydrogenase (EC 1.4.1.1), glutamate dehydrogenase (EC 1.4.1.2), glutamate dehydrogenase (NAD(P)+) (EC 1.4.1.3), glutamate dehydrogenase (NADP+) (EC 1.4.1.4), leucine dehydrogenase (EC 1.4.1.9), glycine dehydrogenase (EC 1.4.1.10), L-erythro-3,5-diaminohexanoate dehydrogenase (EC 1.4.1.11), 2,4-diaminopentanoate dehydrogenase (EC 1.4.1.12), pyrroline-2-carboxylate reductase (EC 1.5.1.1), pyrroline-5-carboxylate reductase (EC EC 1.5.1.2), dihydrofolate reductase (EC EC 1.5.1.3), methylenetetrahydrofolate dehydrogenase (NADP+) (EC 1.5.1.5), D-octopine dehydrogenase (EC 1.5.1.11), methylenetetrahydrofolate dehydrogenase (NAD+) (EC 1.5.1.15), alanopine dehydrogenase (EC 1.5.1.17), 1-piperidine-2-carboxylate reductase (EC 1.5.1.21), NAD(P)+ transhydrogenase (EC 1.6.1.1), glutathione reductase (NAD(P)H) (EC 1.6.4.2), thioredoxin reductase (NADPH) (EC 1.6.4.5), NADH dehydrogenase (EC 1.6.99.3), 5,10-methylenetetrahydrofolate reductase (FADH2) (EC 1.7.99.5), dihydrolipoamide dehydrogenase (EC 1.8.1.4), glutathione-CoA-glutathione transhydrogenase (EC 1.8.4.3), cytochrome-c oxidase (EC EC 1.9.3.1), hydrogen dehydrogenase (EC 1.12.1.2), thetin-homocysteine S-methyltransferase (EC 2.1.1.3), homocysteine S-methyltransferase (EC 2.1.1.10), thymidylate synthase (EC 2.1.1.45), glycine hydroxymethyltransferase (EC 2.1.2.1), glycine formiminotransferase (EC 2.1.2.4), glutamate formiminotransferase (EC 2.1.2.5), D-alanine 2-hydroxymethyltransferase (EC 2.1.2.7), aminomethyltransferase (EC 2.1.2.10), methylmalonyl-CoA carboxyltransferase (EC 2.1.3.1), omithine carbamoyltransferase (EC 2.1.3.3), oxamate carbamoyltransferase (EC 2.1.3.5), glycine amidinotransferase (EC 2.1.4.1), transketolase (EC 2.2.1.1), transaldolase (EC 2.2.1.2), imidazole N-acetyltransferase and phosphate acetyltransferase (EC 2.3.1.2 & 2.3.1.8), arylamine N-acetyltransferase (EC 2.3.1.5), choline O-acetyltransferase (EC 2.3.1.6), carnitine O-acetyltransferase (EC 2.3.1.7), phosphate acetyltransferase (EC 2.3.1.8), phosphate acetyltransferase and formate C-acetyltransferase (EC 2.3.1.8 & 2.3.1.54), phosphate acetyltransferase and acetate kinase (EC 2.3.1.8 & 2.7.2.1), acetyl-CoA C-acetyltransferase (EC 2.3.1.9), carnitine O-palmitoyltransferase (EC 2.3.1.21), glutamate N-acetyltransferase (EC 2.3.1.35), [acyl-carrier-protein] S-acetyltransferase (EC 2.3.1.38), [acyl-carrier-protein] S-malonyltransferase (EC 2.3.1.39), formate C-acetyltransferase (EC 2.3.1.54), sucrose phosphorylase (EC 2.4.1.7), maltose phosphorylase (EC 2.4.1.8), levansucrase (EC 2.4.1.10), sucrose synthase (EC 2.4.1.13), sucrose-phosphate synthase (EC 2.4.1.14),,-trehalose-phosphate synthase (UDP-forming) (EC 2.4.1.15), cellobiose phosphorylase (EC 2.4.1.20), laminaribiose phosphorylase (EC 2.4.1.31),,-trehalose phosphorylase (EC 2.4.1.64), galactinol-raffinose galactosyltransferase (EC 2.4.1.67), sinapate 1-glucosyltransferase (EC 2.4.1.120), purine-nucleoside phosphorylase (EC 2.4.2.1), purine-nucleoside phosphorylase and pyrimidine-nucleoside phosphorylase (EC 2.4.2.1 & 2.4.2.2), pyrimidine-nucleoside phosphorylase (EC 2.4.2.2), uridine phosphorylase (EC 2.4.2.3), nucleoside deoxyribosyltransferase (EC 2.4.2.6), adenine phosphoribosyltransferase (EC 2.4.2.7), hypoxanthine phosphoribosyltransferase (EC 2.4.2.8), orotate phosphoribosyltransferase (EC 2.4.2.10), guanosine phosphorylase (EC 2.4.2.15), thiamine pyridinylase (EC 2.5.1.2), thiamin-phosphate pyrophosphorylase (EC 2.5.1.3), aspartate transaminase (EC 2.6.1.1), malate dehydrogenase and aspartate transaminase (EC 1.1.1.37 & 2.6.1.1), alanine transaminase (EC 2.6.1.2), histidinol-phosphate transaminase (EC 2.6.1.9), omithine-oxo-acid transaminase (EC 2.6.1.13), glutamine-pyruvate aminotransaminase (EC 2.6.1.15), succinyldiaminopimelate transaminase (EC 2.6.1.17), -alanine-pyruvate transaminase (EC 2.6.1.18), 4-aminobutyrate transaminase (EC 2.6.1.19), D-alanine transaminase (EC 2.6.1.21), pyridoxamine-pyruvate transaminase (EC 2.6.1.30), dTDP-4-amino-4,6-dideoxy-D-glucose transaminase (EC 2.6.1.33), glycine-oxaloacetate transaminase (EC 2.6.1.35), 2-aminoadipate transaminase (EC 2.6.1.39), serine-pyruvate transaminase (EC 2.6.1.51), phosphoserine transaminase (EC 2.6.1.52), hexokinase (EC 2.7.1.1), galactokinase (EC 2.7.1.6), 6-phosphofructokinase (EC 2.7.1.11), NAD+ kinase (EC 2.7.1.23), dephospho-CoA kinase (EC 2.7.1.24), glycerol kinase (EC 2.7.1.30), protein kinase (EC 2.7.1.37), pyruvate kinase (EC 2.7.1.40), 1-phosphatidylinositol kinase (EC 2.7.1.67), pyrophosphate-serine phosphotransferase (EC 2.7.1.80), pyrophosphate-fructose-6-phosphate 1-phosphotransferase (EC 2.7.1.90), acetate kinase (EC 2.7.2.1), carbamate kinase (EC 2.7.2.2), phosphoglycerate kinase (EC 2.7.2.3), glyceraldehyde-3-phosphate dehydrogenase and phosphoglycerate kinase (EC 1.2.1.12 & 2.7.2.3), aspartate kinase (EC 2.7.2.4), guanidinoacetate kinase (EC 2.7.3.1), creatine kinase (EC 2.7.3.2), creatine kinase and myosin ATPase (EC 2.7.3.2 & 3.6.1.32), arginine kinase (EC 2.7.3.3), taurocyamine kinase (EC 2.7.3.4), lombricine kinase (EC 2.7.3.5), phosphomevalonate kinase (EC 2.7.4.2), adenylate kinase (EC 2.7.4.3), nucleoside-phosphate kinase (EC 2.7.4.4), nucleoside-diphosphate kinase (EC 2.7.4.6), guanylate kinase (EC 2.7.4.8), nucleoside-triphosphate-adenylate kinase (EC 2.7.4.10), (deoxy) nucleoside-phosphate kinase (EC 2.7.4.13), cytidylate kinase (EC 2.7.4.14), ribose-phosphate pyrophosphokinase (EC 2.7.6.1), nicotinamide-nucleotide adenylyltransferase (EC 2.7.7.1), sulfate adenylyltransferase (EC 2.7.7.4), sulfate adenylyltransferase and inorganic pyrophosphatase (EC 2.7.7.4 & 3.6.1.1), DNA-directed DNA polymerase (EC 2.7.7.7), UTP-glucose-1-phosphate uridylyltransferase (EC 2.7.7.9), UDPglucose-hexose-1-phosphate uridylyltransferase (EC 2.7.7.12), UDPglucose-hexose 1-phosphate uridylyltransferase and UDPglucose (EC 2.7.7.12 & 5.1.3.2), mannose-1-phosphate guanylyltransferase (EC 2.7.7.13), ethanolamine-phosphate cytidylyltransferase (EC 2.7.7.14), choline-phosphate cytidylyltransferase (EC 2.7.7.15), UDP-N-acetylglucosamine pyrophosphorylase (EC 2.7.7.23), glucose-1-phosphate thymidylyltransferase (EC 2.7.7.24), glucose-1-phosphate adenylyltransferase (EC 2.7.7.27), glucose-1-phosphate cytidylyltransferase (EC 2.7.7.33), glucose-1-phosphate guanylyltransferase (EC 2.7.7.34), [glutamate-ammonia-ligase] adenylyltransferase (EC 2.7.7.42), glucuronate-1-phosphate uridylyltransferase (EC 2.7.7.44), pyruvate, orthophosphate dikinase (EC 2.7.9.1), aryl sulfotransferase (EC 2.8.2.1), 3-oxoacid CoA-transferase (EC 2.8.3.5), acetate CoA-transferase (EC 2.8.3.8), triacylglycerol lipase (EC 3.1.1.3), acetylcholinesterase (EC 3.1.1.7), retinyl-palmitate esterase (EC 3.1.1.21), glucose-6-phosphate dehydrogenase and 6-phosphogluconolactonase (EC 1.1.1.49 & 3.1.1.31), alkaline phosphatase (EC 3.1.3.1), acid phosphatase (EC 3.1.3.2), phosphoserine phosphatase (EC 3.1.3.3), 5'-nucleosidase (EC 3.1.3.5), fructose-biphosphatase (EC 3.1.3.11), phosphodiesterase I (EC 3.1.4.1), 3',5'-cyclic-nucleotide phosphodiesterase (EC 3.1.4.17), phosphohydrolase (unclassified) (EC 3.1.4.a), ribonuclease T2 (EC 3.1.27.1), pancreatic ribonuclease (EC 3.1.27.5), ribonuclease (unclassified) (EC 3.1.27.a), cyclomaltodextrin glucanotransferase and -amylase (EC 2.4.1.19 & 3.2.1.1), -amylase (EC 3.2.1.2), glucan 1,4--glucosidase (EC 3.2.1.3), oligo-1,6-glucosidase (EC 3.2.1.10), -glucosidase (EC 3.2.1.20), -glucosidase (EC 3.2.1.21), -galactosidase (EC 3.2.1.23), -mannosidase (EC 3.2.1.24), -fructofuranosidase (EC 3.2.1.26), -dextrin endo-1,6-glucosidase (EC 3.2.1.41), AMP nucleosidase (EC 3.2.2.4), NAD+ nucleosidase (EC 3.2.2.5), NAD(P)+ nucleosidase (EC 3.2.2.6), adenosine nucleosidase (EC 3.2.2.7), adenosylhomocysteinase (EC 3.3.1.1), leucyl aminopeptidase (EC 3.4.11.1), dipeptidyl-peptidase I (EC 3.4.14.1), carboxypeptidase A (EC 3.4.17.1), gly-X carboxypeptidase (EC 3.4.17.4), -glu-X carboxypeptidase (EC 3.4.19.9), chymotrypsin (EC 3.4.21.1), trypsin (EC 3.4.21.4), papain (EC 3.4.22.2), pepsin A (EC 3.4.23.1), chymosin (EC 3.4.23.4), thermolysin (EC 3.4.24.27), asparaginase (EC 3.5.1.1), glutaminase (EC 3.5.1.2), urease (EC 3.5.1.5), penicillin amidase (EC 3.5.1.11), aminoacylase (EC 3.5.1.14), pantothenase (EC 3.5.1.22), N-methyl-2-oxoglutaramate hydrolase (EC 3.5.1.36), dihydroorotase (EC 3.5.2.3), carboxymethylhydantoinase (EC 3.5.2.4), -lactamase (EC 3.5.2.6), arginase (EC 3.5.3.1), allantoicase (EC 3.5.3.4), arginine deiminase (EC 3.5.3.6), adenosine deaminase (EC 3.5.4.4), cytidine deaminase (EC 3.5.4.5), AMP deaminase (EC 3.5.4.6), methenyltetrahydrofolate cyclohydrolase (EC 3.5.4.9), inorganic pyrophosphatase (EC 3.6.1.1), sulfate adenylyltransferase and inorganic pyrophosphatase (EC 2.7.7.4 & 3.6.1.1), trimetaphosphatase (EC 3.6.1.2), nucleotide pyrophosphatase (EC 3.6.1.9), myosin ATPase (EC 3.6.1.32), creatine kinase and myosin ATPase (EC 2.7.3.2 & 3.6.1.32), Ca2+-transporting ATPase (EC 3.6.1.38), chymotrypsin (EC 3.4.21.1), thermolysin (EC 3.4.24.4), phosphoenolpyruvate carboxykinase (GTP) (EC 4.1.1.32), phosphoenolpyruvate carboxykinase (diphosphate) (EC 4.1.1.38), ribulose-biphosphate carboxylase (EC 4.1.1.39), ketotetraose-phosphate aldolase (EC 4.1.2.2), deoxyribose-phosphate aldolase (EC 4.1.2.4), fructose-biphosphate aldolase (EC 4.1.2.13), fructose-biphosphate aldolase and triosephosphate isomerase (EC 4.1.2.13 & 5.3.1.1), 2-dehydro-3-deoxyphosphogluconate aldolase (EC 4.1.2.14), L-fuculose-phosphate aldolase (EC 4.1.2.17), 2-dehydro-3-deoxy-L-pentonate aldolase (EC 4.1.2.18), rhamnulose-1-phosphate aldolase (EC 4.1.2.19), 2-dehydro-3-deoxy-6-phosphogalactonate aldolase (EC 4.1.2.21), D-arabino-3-hexulose phosphate formaldehyde lyase (EC 4.1.2.a), isocitrate lyase (EC 4.1.3.1), malate synthase (EC 4.1.3.2), N-acetylneuraminate lyase (EC 4.1.3.3), citrate (pro-3S)-lyase (EC 4.1.3.6), citrate (si)-synthase (EC 4.1.3.7), citrate (si)-synthase and malate dehydrogenase (EC 4.1.3.7 & 1.1.1.37), ATP citrate(pro-3S)-lyase (EC 4.1.3.8), 4-hydroxy-2-oxoglutarate aldolase (EC 4.1.3.16), citramalate lyase (EC 4.1.3.22), malyl-CoA lyase (EC 4.1.3.24), 2,3-dimethylmalate lyase (EC 4.1.3.32), tryptophanase (EC 4.1.99.1), fumarate hydratase (EC 4.2.1.2), aconitate hydratase (EC 4.2.1.3), 3-dehydroquinate dehydratase (EC 4.2.1.10), phosphopyruvate hydratase (EC 4.2.1.11), enoyl-CoA hydratase (EC 4.2.1.17), tryptophan synthase (EC 4.2.1.20), maleate hydratase (EC 4.2.1.31), (S)-2-methylmalate dehydratase (EC 4.2.1.34), (R)-2-methylmalate dehydratase (EC 4.2.1.35), D-glutamate cyclase (EC 4.2.1.48), urocanate hydratase (EC 4.2.1.49), crotonoyl-[acyl-carrier-protein] hydratase (EC 4.2.1.58), dimethylmaleate hydratase (EC 4.2.1.85), 3-hydroxybutyryl-CoA dehyratase (EC 4.2.1.a), aspartate ammonia-lyase (EC 4.3.1.1), methylaspartate ammonia-lyase (EC 4.3.1.2), histidine ammonia-lyase (EC 4.3.1.3), phenylalanine ammonia-lyase (EC 4.3.1.5), -alanyl-CoA ammonia lyase (EC 4.3.1.6), arginosuccinate lyase (EC 4.3.2.1), adenylosuccinate lyase (EC 4.3.2.2), ureidoglycolate lyase (EC 4.3.2.3), lactoylglutathione lyase (EC 4.4.1.5), adenylate cyclase (EC 4.6.1.1), alanine racemase (EC 5.1.1.1), glutamate racemase (EC 5.1.1.3), lysine racemase (EC 5.1.1.5), diaminopimelate epimerase (EC 5.1.1.7), 4-hydroxyproline epimerase (EC 5.1.1.8), amino-acid racemase (EC 5.1.1.10), ribulose-phosphate 3-epimerase (EC 5.1.3.1), UDPglucose 4-epimerase (EC 5.1.3.2), UDPglucose 4-epimerase and UDPglucose-hexose 1-phosphate (EC 5.1.3.2 & 2.7.7.12), L-ribulose-phosphate 4-epimerase (EC 5.1.3.4), UDParabinose 4-epimerase (EC 5.1.3.5), UDPglucuronate 4-epimerase (EC 5.1.3.6), N-acylglucosamine 2-epimerase (EC 5.1.3.8), N-acylglucosamine-6-phosphate 2-epimerase (EC 5.1.3.9), CDPabequose epimerase (EC 5.1.3.10), glucose-6-phosphate 1-epimerase (EC 5.1.3.15), GDP-D-mannose 3,5-epimerase (EC 5.1.3.18), methylmalonyl-CoA epimerase (EC 5.1.99.1), retinal isomerase (EC 5.2.1.3), linoleate isomerase (EC 5.2.1.5), triose-phosphate isomerase (EC 5.3.1.1), triose-phosphate isomerase and fructose-bisphosphate aldolase (EC 5.3.1.1 & 4.1.2.13), erythrose isomerase (EC 5.3.1.2), arabinose isomerase (EC 5.3.1.3), L-arabinose isomerase (EC 5.3.1.4), xylose isomerase (EC 5.3.1.5), ribose-5-phosphate isomerase (EC 5.3.1.6), mannose isomerase (EC 5.3.1.7), mannose-6-phosphate isomerase (EC 5.3.1.8), glucose-6-phosphate isomerase (EC 5.3.1.9), glucosamine-6-phosphate isomerase (EC 5.3.1.10), glucuronate isomerase (EC 5.3.1.12), arabinose-5-phosphate isomerase (EC 5.3.1.13), L-rhamnose isomerase (EC 5.3.1.14), D-lyxose ketol-isomerase (EC 5.3.1.15), ribose isomerase (EC 5.3.1.20), L-mannose ketol-isomerase (EC 5.3.1.a), phospho-3-hexuloisomerase (EC 5.3.1.b), phenylpyruvate tautomerase (EC 5.3.2.1), oxaloacetate tautomerase (EC 5.3.2.2), isopentenyl-diphosphate -isomerase (EC 5.3.3.2), methylitaconate -isomerase (EC 5.3.3.6), phosphoglycerate mutase (EC 5.4.2.1), phosphoglucomutase (EC 5.4.2.2), phosphoacetylglucosamine mutase (EC 5.4.2.3), -phosphoglucomutase (EC 5.4.2.6), phosphopentomutase (EC 5.4.2.7), phosphomannomutase (EC 5.4.2.8), lysine 2,3-aminomutase (EC 5.4.3.2), D-omithine 4,5-aminomutase (EC 5.4.3.5), methylaspartate mutase (EC 5.4.99.1), methylmalonyl-CoA mutase (EC 5.4.99.2), 2-methyleneglutarate mutase (EC 5.4.99.4), muconate cycloisomerase (EC 5.5.1.1), tetrahydroxypteridine cycloisomerase (EC 5.5.1.3), chalcone isomerase (EC 5.5.1.6), valine-tRNA ligase (EC 6.1.1.9), acetate-CoA ligase (EC 6.2.1.1), butyrate CoA ligase (EC 6.2.1.2), succinate-CoA ligase (GDP-forming) (EC 6.2.1.4), succinate-CoA ligase (ADP forming) (EC 6.2.1.5), glutamate-ammonia ligase (EC 6.3.1.2), formate-tetrahydrofolate ligase (EC 6.3.4.3), adenylosuccinate synthase (EC 6.3.4.4), arginosuccinate synthase (EC 6.3.4.5), pyruvate carboxylase (EC 6.4.1.1), propanoyl-CoA carboxylase (EC 6.4.1.3), hemoglobin, tyrosine hydroxylase, prohormone convertase, bcl-2, dopa decarboxylase, and dopamine beta-hydroxylase.

5.4.3. Assay of Encapsulated Reaction Centers

Any number of methods are available to determine whether a reaction center retains its ability to convert prodrug to biologically active agent upon encapsulation. Those of skill in the art will be able to modify, if necessary, any standard procedures developed for assaying the reaction center in free solution for assaying the encapsulated reaction center. For example, if the matrix is transparent, as is true for silica-based sol-gel matrices, then standard visible and UV-Vis techniques for solid materials may be employed. Yamanka et al. *J. Sol-Gel sci. & tech.* 7:117–21 (1996). If the reaction center is redox active center, e.g., a transition metal, then other spectroscopies, such as EPR, may be employed. Lin et al. *J. Sol-Gel Sci. & Tech.* 7:19–26 (1996). As discussed below for the prodrugs, assaying for reaction center activity often involves measuring the reactants and products, and solution techniques may be applicable. Alternatively, coenzymes, cofactors, or other reactants involved in any reaction center may be monitored as an assay for activity of any encapsulated reaction center.

From such assays, it should be possible to determine the reaction kinetics for the encapsulated reaction center. In general, for enzymes, the reaction kinetics may correspond to the Michaelis-Menten treatment. Zubay et al. *Biochemistry* 137–141 (1983). An apparent Michaelis constant (Km) may be determined for the encapsulated reaction center. Dosoretz et al., *J. Sol-Gel Sci. & Tech.* 7:7–11 (1996). The Km for the nonencapsulated reaction center and the Km of the encapsulated reaction center may be compared. In certain embodiments, the ratio of Km (nonencapsulated) to Km (encapsulated) may be greater than one. Dosoretz et al., supra. In other embodiments, the ratio may be less than one. Venton et al. *Biochim Biophys Acta* 1250:117–25 (1995). The present invention contemplates ratios of 100, 10, 5, 1, 0.5, 0.1, 0.005, 0.01, and 0.001. Of course, for determining any of these ratios, the conditions of the reaction should be kept as similar as possible.

The encapsulation of reaction centers allows for the design of novel assays for reaction center activity. For example, a second reaction center may be encapsulated so as to help assay the activity of a first encapsulated reaction center. Yamanka et al. report encapsulating both oxalate oxidase and peroxidase. The peroxidase converts two dye precursors into a detectable dye using hydrogen peroxide, which is formed by oxalate oxidase from oxalate, water, and dioxygen. Yamanka et al. *J. Sol-Gel Sci. & Tech.* 7:117–21 (1996). Hence, the peroxidase in this sol-gel matrix assists in assaying the reaction kinetics of the oxalate oxidase. Yamanka et al. report that this enzyme system is useful as a diagnostic for the decreased secretion of oxalate in cases of hyperglycinemia, hypoclycinuria, and hyperoxaluria. Ngo et al. *Anal. Biochem.* 105:389 (1980).

5.5. Prodrugs

5.5.1. Prodrugs Contemplated by the Invention

A variety of materials or compounds may be employed as prodrugs in the present invention. A number of such prodrugs have been discussed elsewhere, including when considering possible reaction centers and uses of the present invention. Any compound that is biologically active may be used in the present invention as a prodrug, as long as a suitable prodrug may be prepared that may be converted by a reaction center into a biologically active compound. The matrices of the present invention may be administered by-way of oral ingestion or implantation. If implantation is desired, they can be implanted subcutaneously, constitute a part of a prosthesis, or be inserted in a cavity of the human body. Subcutaneous implantation using a syringe consists of injecting the amtrices directly into subcutaneous tissue. Thus, the matrices of the present invention can be suspended in a physiological buffer and introduced via a syringe to the desired site. In certain cases, a biologically active agent may itself be used as a prodrug in the present invention if a reaction center modulates its biological activity upon reaction.

A number of considerations may be weighed by those of skill in the art in determining which prodrug is appropriate for any use of the present invention. For example, it may be necessary to match a prodrug with a reaction center that has a high activity for conversion of the prodrug. Alternatively, in choosing a prodrug, it may be important to consider where in a subject the resulting matrix may be administered, e.g., the use of the prodrug L-dopa to produce the biologically active agent dopamine in the striatum. Another possible consideration may be the physical dimension of any prodrug, for to operate as a prodrug, it may need to diffuse into the matrix for conversion by the reaction center to a biologically active agent. (Alternatively, the reaction center may be located on the surface of the matrix, whereupon no diffusion is necessary for conversion of the prodrug.) However, even antibodies have been observed to diffuse into matrices of the present invention, so any prodrug of at least that dimension may be used in the present invention. As discussed in preparing the matrices of the present invention, it may be necessary to ensure that the physical size of the reaction center is greater than that of its counterpart prodrug so as to prevent leaching. This criteria need not always apply, however, because for example, the reaction center may be covalently attached to the matrix, which may prevent any substantial leaching, or alternatively, any leaching that may occur may be acceptable for any use that the matrix is put.

Possible biologically active agents, which may be used as prodrugs in the present invention after appropriate modification, include without limitation, medicaments; vitamins; mineral supplements; substances used for the treatment, prevention, diagnosis, cure or mitigation of disease or illness; or substances which affect the structure or function of the body.

Specific types of biologically active agents include, without limitation: anti-angiogenesis factors, antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; catecholamines; diuretics; vasodilators including general coronary, peripheral and cerebral; central nervous system stimulants; cough and cold preparations, including decongestants; growth factors, hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, lipoproteins, interferons, cytokines, chemotherapeutic agents and other anti-neoplastics, antibiotics, anti-virals, anti-fungals, anti-inflammatories, anticoagulants, lymphokines, or antigenic materials.

To illustrate further, other types of biologically active agents that may be used as prodrugs upon appropriate modification if necessary, including peptide, proteins or other biopolymers, e.g., interferons, interleukins, tumor necrosis factor, nerve growth factor (NGF), brain-derived neurotrophic factor (BDNF), neurotrophin-3 (NT-3), neurotrophin-4/5 (NT-4/5), ciliary neurotrophic factor (CNTF), glial cell line-derived neurotrophic factor (GDNF), cholinergic differentiation factor/Leukemia inhibitory factor (CDF/LIF), epidermal growth factor (EGF), insulin-like growth factor (IGF), basic fibroblast growth factor (bFGF), platelet-derived growth factor (PDGF), erythropoietin, growth hormone, Substance-P, neurotensin, insulin, erythropoietin, albumin, transferrin, and other protein biological response modifiers.

Other examples of biologically active agents that may be used as prodrugs in accordance with the present invention either directly or after appropriate modification include acebutolol, acetaminophen, acetohydoxamic acid, acetophenazine, acyclovir, adrenocorticoids, allopurinol, alprazolam, aluminum hydroxide, amantadine, ambenonium, amiloride, aminobenzoate potassium, amobarbital, amoxicillin, amphetamine, ampicillin, androgens, anesthetics, anticoagulants, anticonvulsants-dione type, antithyroid medicine, appetite suppressants, aspirin, atenolol, atropine, azatadine, bacampicillin, baclofen, beclomethasone, belladonna, bendroflumethiazide, benzoyl peroxide, benzthiazide, benztropine, betamethasone, bethanechol, biperiden, bisacodyl, bromocriptine, bromodiphenhydramine, brompheniramine, buclizine, bumetanide, busulfan, butabarbital, butaperazine, caffeine, calcium carbonate, captopril, carbamazepine, carbenicillin, carbidopa & levodopa, carbinoxamine inhibitors, carbonic anhydsase, carisoprodol, carphenazine, cascara, cefaclor, cefadroxil, cephalexin, cephradine, chlophedianol, chloral hydrate, chlorambucil, chloramphenicol, chlordiazepoxide, chloroquine, chlorothiazide, chlorotrianisene, chlorpheniramine, 6X chlorpromazine, chlorpropamide, chlorprothixene, chlorthalidone, chlorzoxazone, cholestyramine, cimetidine, cinoxacin, clemastine, clidinium, clindamycin, clofibrate, clomiphere, clonidine, clorazepate, cloxacillin, colochicine, coloestipol, conjugated estrogen, contraceptives, cortisone, cromolyn, cyclacillin, cyclandelate, cyclizine, cyclobenzaprine, cyclophosphamide, cyclothiazide, cycrimine, cyproheptadine, danazol, danthron, dantrolene, dapsone, dextroamphetaminte, dexamethasone, dexchlorpheniramine, dextromethorphan, diazepan, dicloxacillin, dicyclomine, diethylstilbestrol, diflunisal, digitalis, diltiazen, dimenhydrinate, dimethindene, diphenhydramine, diphenidol, diphenoxylate & atrophive, diphenylopyraline, dipyradamole, disopyramide, disulfiram, divalporex, docusate calcium, docusate potassium, docusate sodium, doxyloamine, dronabinol ephedrine, epinephrine, ergoloidmesylates, ergonovine, ergotamine, erythromycins, esterified estrogens, estradiol, estrogen, estrone, estropipute, etharynic acid, ethchlorvynol, ethinyl estradiol, ethopropazine, ethosaximide, ethotoin, fenoprofen, ferrous fumarate, ferrous gluconate, ferrous sulfate, flavoxate, flecainide, fluphenazine, fluprednisolone, flurazepam, folic acid, furosemide, gemfibrozil, glipizide, glyburide, glycopyrrolate, gold compounds, griseofuwin, guaifenesin, guanabenz, guanadrel, guanethidine, halazepam, haloperidol, hetacillin, hexobarbital, hydralazine, hydrochlorothiazide, hydrocortisone (cortisol), hydroflunethiazide, hydroxychloroquine, hydroxyzine, hyoscyatmine, ibuprofen, indapamide, indomethacin, insulin, iofoquinol, iron-polysaccharide, isoetharine, isoniazid, isopropamide isoproterenol, isotretinoin, isoxsuprine, kaolin & pectin, ketoconazole, lactulose, levodopa, lincomycin liothyronine, liotrix, lithium, loperamide, lorazepam, magnesium hydroxide, magnesium sulfate, magnesium trisilicate, maprotiline, meclizine, meclofenamate, medroxyproyesterone, melenamic acid, melphalan, mephenytoin, mephobarbital, meprobamate, mercaptopurine, mesoridazine, metaproterenol, metaxalone, methamphetamine, methaqualone, metharbital, methenamine, methicillin, methocarbamol, methotrexate, methsuximide, methyclothinzide, methylcellulos, methyldopa, methylergonovine, methylphenidate, methylprednisolone, methysergide, metoclopramide, metolazone, metoprolol, metronidazole, minoxidil, mitotane, monamine oxidase inhibitors, nadolol, nafcillin, nalidixic acid, naproxen, narcotic analgesics, neomycin, neostigmine, niacin, nicotine, nifedipine, nitrates, nitrofurantoin, nomifensine, norethindrone, norethindrone acetate, norgestrel, nylidrin, nystatin, orphenadrine, oxacillin, oxazepam, oxprenolol, oxymetazoline, oxyphenbutazone, pancrelipase, pantothenic acid, papaverine, para-aminosalicylic acid, paramethasone, paregoric, pemoline, penicillamine, penicillin, penicillin -v, pentobarbital, perphenazine, phenacetin, phenazopyridine, pheniramine, phenobarbital, phenolphthalein, phenprocoumon, phensuximide, phenylbutazone, phenylephrine, phenylpropanolamine, phenyl toloxamine, phenytoin, pilocarpine, pindolol, piper acetazine, piroxicam, poloxamer, polycarbophil calcium, polythiazide, potassium supplements, pruzepam, prazosin, prednisolone, prednisone, primidone, probenecid, probucol, procainamide, procarbazine, prochlorperazine, procyclidine, promazine, promethazine, propantheline, propranolol, pseudoephedrine, psoralens, psyllium, pyridostigmine, pyrodoxine, pyrilamine, pyrvinium, quinestrol, quinethazone, quinidine, quinine, ranitidine, rauwolfia alkaloids, riboflavin, rifampin, ritodrine, salicylates, scopolamine, secobarbital, senna, sannosides a & b, simethicone, sodium bicarbonate, sodium phosphate, sodium fluoride, spironolactone, sucrulfate, sulfacytine, sulfamethoxazole, sulfasalazine, sulfinpyrazone, sulfisoxazole, sulindac, talbutal, tamazepam, terbutaline, terfenadine, terphinhydrate, teracyclines, thiabendazole, thiamine, thioridazine, thiothixene, thyroblobulin, thyroid, thyroxine, ticarcillin, timolol, tocainide, tolazamide, tolbutamide, tolmetin trozodone, tretinoin, triamcinolone, trianterene, triazolam, trichlormethiazide, tricyclic antidepressants, tridhexethyl, trifluoperazine, triflupromazine, trihexyphenidyl, trimeprazine, trimethobenzamine, trimethoprim, tripclennamine, triprolidine, valproic acid, verapamil, vitamin A, vitamin B-12, vitamin C, vitamin D, vitamin E, vitamin K, xanthine, parathyroid hormone, enkephalins, and endorphins.

To illustrate further, antimetabolites may be used as prodrugs upon appropriate modification if necessary, including without limitation methotrexate, 5-fluorouracil, cytosine arabinoside (ara-C), 5-azacytidine, 6-mercaptopurine, 6-thioguanine, and fludarabine phosphate. Antitumor antibiotics may include but are not limited to doxorubicin, daunorubicin, dactinomycin, bleomycin, mitomycin C, plicamycin, idarubicin, and mitoxantrone. Vinca alkaloids and epipodophyllotoxins may include, but are not limited to vincristine, vinblastine, vindesine, etoposide, and teniposide. Nitrosoureas, including carmustine, lomustine, semustine and streptozocin, may also be prodrugs, upon appropriate modification if necessary. Hormonal therapeutics may also be prodrugs, upon appropriate modification if necessary, such as corticosteriods (cortisone acetate, hydrocortisone, prednisone, prednisolone, methyl prednisolone and dexamethasone), estrogens, (diethylstibesterol, estradiol, esterified estrogens, conjugated estrogen, chlorotiasnene), progestins (medroxyprogesterone acetate, hydroxy progesterone caproate, megestrol acetate), antiestrogens (tamoxifen), aromastase inhibitors (aminoglutethimide), androgens (testosterone propionate, methyltestosterone, fluoxymesterone, testolactone), antiandrogens (flutamide), LHRH analogues (leuprolide acetate), and endocrines for prostate cancer (ketoconazole). Antitumor drugs that are radiation enhancers may also be used as prodrugs, upon appropriate modification if necessary. Examples of such biologically active agents include, for example, the chemotherapeutic agents 5'-fluorouracil, mitomycin, cisplatin and its derivatives, taxol, bleomycins, daunomycins, and methamycins. Antibiotics may be used as prodrugs as well, upon appropriate modification if necessary, and they are well known to those of skill in the art, and include, for example, penicillins, cephalosporins, tetracyclines, ampicillin, aureothicin, bacitracin, chloramphenicol, cycloserine, erythromycin, gentamicin, gramacidins, kanamycins, neomycins, streptomycins, tobramycin, and vancomycin.

Other prodrugs, upon appropriate modification if necessary, which may be used in the present invention include those presently classified as investigational drugs, and can include, but are not limited to alkylating agents such as Nimustine AZQ, BZQ, cyclodisone, DADAG, CB10-227, CY233, DABIS maleate, EDMN, Fotemustine, Hepsulfam, Hexamethylmelamine, Mafosamide, MDMS, PCNU, Spiromustine, TA-077, TCNU and Temozolomide; antimetabolites, such as acivicin, Azacytidine, 5-aza-deoxycytidine, A-TDA, Benzylidene glucose, Carbetimer, CB3717, Deazaguanine mesylate, DODOX, Doxifluridine, DUP-785, 10-EDAM, Fazarabine, Fludarabine, MZPES, MMPR, PALA, PLAC, TCAR, TMQ, TNC-P and Piritrexim; antitumor antibodies, such as AMPAS, BWA770U, BWA773U, BWA502U, Amonafide, m-AMSA, CI-921, Datelliptium, Mitonafide, Piroxantrone, Aclarubicin, Cytorhodin, Epirubicin, esorubicin, Idarubicin, Iodo-doxorubicin, Marcellomycin, Menaril, Morpholino anthracyclines, Pirarubicin, and SM-5887; microtubule spindle inhibitors, such as Amphethinile, Navelbine, and Taxol; the alkyl-lysophospholipids, such as BM41-440, ET-18-OCH3, and Hexacyclophosphocholine; metallic compounds, such as Gallium Nitrate, CL286558, CL287110, Cycloplatam, DWA2114R, NK121, Iproplatin, Oxaliplatin, Spiroplatin, Spirogermanium, and Titanium compounds; and novel compounds such as, for example, Aphidoicolin glycinate, Ambazone, BSO, Caracemide, DSG, Didemnin, B, DMFO, Elsamicin, Esperrtatrucin, Flavone acetic acid, HMBA, HHT, ICRF-187, Iododeoxyuridine, Ipomeanol, Liblomycin, Lonidamine, LY186641, MAP, MTQ, Merabarone SK&F104864, Suramin, Tallysomycin, Teniposide, THU and WR2721; and Toremifene, Trilosane, and zindoxifene.

5.5.2. Assay's and Identification of Prodrugs

As a general matter, it will be clear to one of skill in the art which prodrugs may be used with which reaction centers so as to effect the any of the uses of the subject invention, e.g., producing a biologically active agent. Prodrugs that display desired characteristics, e.g., certain kinetic profiles of conversion of a prodrug by a reaction center to the corresponding biologically active agent, may serve as lead compounds for the discovery of more desirable prodrugs.

In general, there are a number of methods by which useful prodrugs of any reaction center encapsulated in a sol gel may be determined. For example, prodrugs may be individually prepared and tested for production of the corresponding biologically active agent upon interaction with the reaction center, whether encapsulated or not.

In another embodiment of the present invention, the use of prodrugs in this invention readily lends itself to the creation of combinatorial libraries of compounds for screening prospective prodrugs with any particular reaction center or group of reaction centers to identify prodrugs of such reaction centers. For the purposes of the present invention, the application of combinatorial chemistry may be especially valuable because it may render identification of a suitable prodrug of a biologically active agent for use with a particular reaction center more facile. A combinatorial library for the purposes of the present invention is a mixture of chemically related compounds which may be screened together for a desired property, e.g., conversion by a particular reaction center or reaction centers to produce a biologically active agent. Such libraries may be in solution or covalently linked to a solid support. The preparation of many related compounds as prospective prodrugs in a single reaction greatly reduces and simplifies the number of screening processes which need to be carried out. Screening for the appropriate reactivity of any prospective prodrug may be done by conventional methods.

For purposes of this invention, diversity in a library may be created at a variety of different levels. In general, for instance, substrate aryl groups used in a combinatorial approach can be diverse in terms of the core aryl moiety, e.g., a variegation in terms of the ring structure, and/or can be varied with respect to the other substituents. With respect to the subject invention, for example, it is generally known that carboxypeptidases hydrolyze amide bonds. Any biologically active agent having an amine or carboxylic acid moiety may, in theory, be derivatized in a combinatorial approach to form an amide with a carboxylic acid or amine moiety, respectively. For example, a peptidyl fragment having a varied number of amino acid residues with a diverse identity could be coupled to a biologically active agent of interest to give a library of prospective prodrugs, whereupon conversion by reaction centers such as carboxypeptidases of the prospective prodrugs in the library could be screened. In this fashion, prospective prodrugs of a biologically active agent could be prepared and screened for use with a particular reaction center, or alternatively, a group of reaction centers that catalyze a similar type of chemical conversion. As already noted above, the reaction centers themselves may be prepared and screened by combination methods as well. As will be clear to one of skill in the art, in preparing any such library, some considerations to take into account include the chemical conversion catalyzed by the reaction center or centers of interest; in what fashion a biologically active agent may be readily derivatized to provide prodrugs so that the reaction center or centers of interest could produce the biologically active agent from a prodrug; and the specificity of the reaction center or centers of interest to a variation in structure with respect to the reaction that it normally catalyzes, e.g., the naturally occurring substrate for an enzyme.

A variety of techniques are available in the art for generating combinatorial libraries of small organic molecules. See generally Blondelle et al. *Trends Anal. Chem.* 14:83 (1995); U.S. Pat. Nos. 5,359,115, 5,362,899, 5,288,514, and 5,721,099; Chen et al. *JACS* 116:2661 (1994; Kerr et al. *JACS* 115:252 (1993); WO92/10092, WO93/09668, WO 94/08051, WO93/20242 and WO91/07087. Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in WO 94/08051, e.g., being linked to a polymer bead by a hydrolyzable or photolyzable group, e.g., located at one of the positions of substrate. According to the technique disclosed therein, the library is synthesized on a set of beads, each bead including a set of tags identifying the particular diversomer on that bead. In one embodiment, the beads can be dispersed on the surface of a permeable membrane, and the diversomers released from the beads by lysis of the bead linker. The diversomer from each bead will diffuse across the membrane to an assay zone, where it will interact with an assay for a reaction center or centers. Detailed descriptions of a number of combinatorial methodologies are provided below.

(a) Direct Characterization. A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

(b) Multipin Synthesis. The libraries of the subject method can take the multipin library format. Briefly, Geysen and co-workers, Geysen et al. *PNAS* 81:3998–4002 (1984), introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation. Compare Bray et al. *Tetrahedron Lett.* 31:5811–14 (1990); Valerio et al. *Anal Biochem* 197:168–77 (1991); Bray et al. *Tetrahedron Lett,* 32:6163–66 (1991).

(c) Divide-Couple-Recombine. In yet another embodiment, a variegated library of compounds can be provided on a set of beads utilizing the strategy of divide-couple-recombine. See, for example, Houghten *PNAS* 82:5131–35 (1985); and U.S. Pat. Nos. 4,631,211; 5,440,016; 5,480,971. Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags. Houghten et al. *PNAS* 82:5131–35 (1986). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

(d) Combinatorial Libraries by Light-Directed, Spatially Addressable Parallel Chemical Synthesis. A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support. Dower et al. *Annu Rep Med Chem* 26:271–280 (1991); Fodor, *Science* 251:767 (1991); U.S. Pat. No. 5,143, 854; Jacobs et al. *Trends Biotechnol* 12:19–26 (1994). The spatial resolution of photolithography affords miniaturization. This technique can be carried out through the use of protection/deprotection reactions with photolabile protecting groups.

The key points of this technology are illustrated in Gallop et al. *J Med Chem* 37:1233–51 (1994). A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed. With respect to the above example, for example, a library of peptidyl fragments could thereby be prepared, whereupon the biologically active agent could be coupled in the final step to produce a diverse library of prospective prodrugs when paired with reaction centers that hydrolyze peptide bonds.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

(e) Encoded Combinatorial Libraries. In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

(1) Tagging with sequenceable bio-oligomers. The principle of using oligonucleotides to encode combinatorial synthetic libraries was described in 1992 Brenner et al. PNAS 89:5381–83 (1992), and an example of such a library appeared the following year. Needles et al. *PNAS* 90:10700–04 (1993). A combinatorial library of nominally $7_7$ (=823,543) peptides composed of all combinations of Arg, Gln, Phe, Lys, Val, D-Val and TLr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach, Kerr et al. *J Am Chem Soc* 115:2529–31 (1993), orthogonality in synthesis is achieved by employing acid-labile protection for the coding strand and base-labile protection for the compound strand.

In an alternative approach, Nikolaiev et al. *Pept Res* 6:161–70 (1993), branched linkers are employed so that the coding unit and the test compound can both be attached to the same functional group on the resin. In one embodiment, a cleavable linker can be placed between the branch point and the bead so that cleavage releases a molecule containing both code and the compound. Ptek et al. *Tetrahedron Lett* 32:3891–94 (1991). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

(2) Non-sequenceable Tagging: Binary Encoding. An alternative form of encoding the test compound library employs a set of non-sequencable electrophoric tagging molecules that are used as a binary code. Ohlmeyer et al. *PNAS* 90:10922–26 (1993). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report, Ohlmeyer et al., supra, the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix. Nestler et al. *J Org Chem* 59:4723–24 (1994). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase, Ohlmeyer et al. *PNAS* 92:6027–31 (1995), and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

When prospective prodrugs are screened as libraries of compounds, high throughput assays are desirable in order to maximize the number of compounds surveyed in a given period of time. The activity of the reaction center, e.g., enzymatic activity, with any prospective prodrug may be determined by monitoring either the disappearance of prodrug or the appearance of the corresponding biologically active agent. Alternatively, the reaction center activity may be determined by monitoring the reduction or production or any reactants consumed or by-products produced. Spectroscopic methods well-known to those of skill may be used for such monitoring, or alternatively, any of the reactants or products, e.g., the prodrug or the corresponding biologically active agent, may be isolated and quantified.

In other embodiments, differential assays can be used to identify prodrugs that react more readily with a encapsulated reaction center than with any other naturally occurring enzyme, so that any such prodrug are converted chiefly by any administered encapsulated reaction center instead of by any naturally occurring enzymes or catalysts. Such a feature may be desirable depending on how the matrix is used.

5.6. Administration 5.6.1. Matrix Administration

Immobilized enzymes may be administered in a variety of ways. See generally Ming et al. *Methods for Therapeutic Applications* 46:676–699. The site of administration of the matrix may affect its therapeutic effect depending on the reaction center encapsulated therein. For example, the site of implantation of encapsulated PC12 cells for treatment of Parkinson's disease appears to affect the device output. Emerich et al. *Cell Transplant.* 5:589–96 (1996).

A number of different implantation sites in a subject are contemplated for the matrices of this invention. In particular, the most preferred site is determined by the identity of the encapsulated reaction center. Any site that results in a therapeutic effect may be used. For example, for reaction centers that produce biologically active agents that are cytotoxic, the implants may be implanted near any neoplasm. ADEPT technology relies on such proximity to deliver any cytotoxic agent essentially directly to the tumor. In another instance, for matrices used to treat Parkinson's disease by affecting dopamine levels in the brain, implantation in the brain may be preferred. Other sites in the brain for such matrices include the basal ganglia, the substantia nigra, and the striatum.

The matrices of the present invention may be administered by way of oral ingestion or implantation. If implantation is desired, they can be implanted subcutaneously, constitute a part of a prosthesis, or be inserted in a cavity of the human body. Subcutaneous implantation using a syringe consists of injecting the matrices directly into subcutaneous tissue. Thus, the matrices of the present invention can be suspended in a physiological buffer and introduced via a syringe to the desired site. Other sites include the central nervous system, including the brain, spinal cord, and aqueous and vitreous humors of the eye. Other sites in the brain include the cerebral cortex, subthalamic nuclei and nucleus Basalis of Maynert. Other sites include the cerebrospinal fluid, the subarachnoid space, and the lateral ventricles. Other sites includes the kidney subcapsular site, and intraperitoneal and subcutaneous sites.

In other embodiments of the present invention, the matrices of the present invention may be associated with a medical article to be used as an implant. For example, matrices of the present invention could be attached as thin films to such devices. Alternatively, matrices of the present invention could be attached as a capsule or incorporated into any medical device. Exemplary structural medical articles include such implants as orthopedic fixation devices, ventricular shunts, laminates for degradable fabric, drug-carriers, burn dressings, coatings to be placed on other implant devices, and the like.

For administration of matrices of the present invention, an important feature may be whether the matrix is intended to stay in place after administration or move in the subject. For example, matrices administered to a subject may be transported and localized in the lymphatic system as part of the subject immune response to the foreign objects.

Once a matrix of the present invention is administered, it may remain in at least partial contact with a biological fluid, such as blood, internal organ secretions, mucus membranes, cerebrospinal fluid, and the like.

The length of the period during which encapsulated reaction center remains active enough so as to produce a therapeutic effect may depend on a variety of features. Enzymes encapsulated in silica-based sol-gel matrices have remained active for periods of several months. The administration of any matrix of the present invention may result in the long-term, stable production of a biologically active agent.

5.6.2. Formulations and Use of Matrices and Prodrugs

In addition to the general introduction, pharmaceutical compositions for use in accordance with the present invention may be formulated in a conventional manner using one or more physiologically acceptable carriers or excipients. Thus, as appropriate, matrices and any prodrug, including any physiologically acceptable salts and solvates, may be formulated for administration by, for example, injection, inhalation or insufflation (either through the mouth or the nose) or oral, buccal, parenteral or rectal administration. Appropriate formulations may depend, in part, on the administration method used and whether a prodrug or a matrix is being administered.

The matrices or prodrugs of the invention may be formulated for a variety of loads of administration, including systemic and topical or localized administration. Techniques and formulations generally may be found in Remmington's Pharmaceutical Sciences, Meade Publishing Co., Easton, Pa. Intramuscular, intravenous, intraperitoneal, and subcutaneous injection is possible. For injection, the matrices or prodrugs of the invention can be formulated in liquid solutions, preferably in physiologically compatible buffers such as Hank's solution or Ringer's solution. In addition, the prodrugs may be formulated in solid form and redissolved or suspended immediately prior to use. Lyophilized forms are also included.

For oral administration, the matrices or prodrugs may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of any prodrug. For buccal administration the prodrugs may take the form of tablets or lozenges formulated in conventional manner. For administration by inhalation, the prodrugs for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The prodrugs and/or matrices may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the prodrug may be in powder form for constitution with a suitable vehicle, e.g., sterile pyrogen-free water, before use.

The prodrugs may also be formulated in rectal compositions such as suppositories or retention enemas, e.g., containing conventional suppository bases such as cocoa butter or other glycerides.

In addition to the formulations described previously, the prodrugs and matrices of the present invention may also be formulated as a depot preparation. Such long acting formulations may be administered by implantation (for example subcutaneously or intramuscularly) or by intramuscular injection. Thus, for example, the prodrugs may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the e.g. heart or other organs without causing inflammation or ischemia. Other methods of controlled release of the prodrugs and matrices of the present invention are known to those of skill in the art.

Systemic administration may also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the prodrugs of the invention are formulated into ointments, salves, gels, or creams as generally known in the art. A wash solution can be used locally to treat an injury or inflammation to accelerate healing.

The prodrugs and/or matrices may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The prodrugs may be employed in the present invention in various forms, such as molecular complexes or pharmaceutically acceptable salts. Representative examples of such salts are succinate, hydrochloride, hydrobromide, sulfate, phosphate, nitrate, borate, acetate, maleate, tartrate, salicylate, metal salts (e.g., alkali or alkaline earth), ammonium or amine salts (e.g., quaternary ammonium) and the like. Furthermore, derivatives of the prodrugs such as esters, amides, and ethers which have desirable retention and release characteristics but which are readily hydrolyzed in vivo by physiological pH or enzymes can also be employed.

5.7. Treatment

The selected dosage level for the matrices and prodrugs, if applicable, of the present invention will depend upon a variety of factors including: the load of the reaction center within the matrix; the activity of the reaction center, the activity of the particular prodrug employed, or the ester, salt or amide thereof; the route of administration; the time of administration, the rate of excretion of the particular prodrug (and possibly matrix) being employed, the duration of the treatment, other drugs, compounds and/or materials used in combination with the particular matrix and prodrug employed, the age, sex, weight, condition, general health and prior medical history of the patient being treated, and like factors well known in the medical arts.

Toxicity and therapeutic efficacy of the matrices of the present invention may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. In certain embodiments, those in which an exogenous prodrug is activated by the reaction center encapsulated in a biocompatible matrix of the subject invention, the efficacy of treatment using the subject invention may be gauged by comparing any of the foregoing parameters resulting from treatment using a prodrug alone (i.e., without the subject matrix), the biologically active substance that results from the prodrug alone, and treatment using the prodrug and a subject matrix as disclosed herein. In certain embodiments, treatments using the subject invention have ratios of about two (or less), five, ten, one hundred, one thousand or even greater orders of magnitude more favorable than treatment with the prodrug alone or the biologically active substance that results from the prodrug alone.

Because the matrix itself does not result in a therapeutic effect without the involvement of some other compound, e.g., a prodrug or naturally occurring metabolite, but also the availability of other compounds that interact with the matrix may affect any treatment regime. In general, matrices and the biologically active agents that they produce which exhibit large therapeutic indices are preferred. By targeting the matrix to a particular region of a subject so as to localize the production of the biologically active agent, the therapeutic efficacy may be dramatically increased, and unwanted side effects may be minimized. For example, by implanting the dopamine producing matrix in the striatum, it may not be necessary to administer L-dopa with carbidopa or benserazide, which is used to combat nausea resulting from conversion of L-dopa to dopamine outside of the brain.

Because the matrix, upon administration, may be in place and active for significant time periods, ant treatment regime may involve multiple administrations of a prodrug so as to produce biologically active agent.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any matrix and/or prodrug used in the present invention, the therapeutically effective dose can be estimated initially from cell culture assays. For example, a dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma of a biologically active agent may be measured, for example, by high performance liquid chromatography.

Exemplifications

The present invention now being generally described, it may be more readily understood by reference to the following examples which are included merely for purposes of illustration of certain aspects and embodiments of the present invention, and are not intended to limit the invention in any way.

A. Reaction Center Encapsulation Studies

1. Matrix Preparation

The general synthetic technique used for preparation of the silica sol was addition of 21 mL of tetramethyl orthosilicate (Aldrich, 99+%) and 5.08 mL of a 4 mM HCl solution to a 25×150 mm test tube equipped with a stirbar. The mixture is stirred until homogeneous (approximately 15 minutes). The test tube containing the sol is then transferred to an ice bath and allowed to cool for 10 minutes. A 2 mL aliquot of sol is then transferred to another chilled test tube in an ice bath and stirred. To this sol, 1 mL of chilled buffer solution (appropriate to the enzyme to be entrapped) is added, and stirred for ca. 10 s, followed by addition of 1 mL of chilled, buffered solution containing the desired enzyme. The sol is swirled briefly, and then pipetted into a 4.5 mL polystyrene cuvette (cell culture dishes were also used for surface area study matrices). The cuvette opening is sealed with Parafilm following gel formation (cell culture dish covers were used for surface area study matrices). The gel is then allowed to age in the sealed container for a period of time ranging from 18 h to 50 d or more at temperatures ranging from 4° C. to room temperature. Selected samples were dried at ambient temperature over a period of days to weeks by puncturing the Parafilm covering the container opening. Other samples were assayed without drying.

2. Enzyme Encapsulation and Assays a) b-Glucosidase

The entrapment of b-Glucosidase (from almonds, crude, lyophilized powder, Sigma) was performed as outlined above, using 50 mM, pH 5.0 acetate buffer. The activity assay was performed using 2.667 mL of a 10 mM solution of para-nitrophenyl-b-D-glucopyranoside (Sigma, 99+%) in buffer and 37.33 mL acetate buffer in a 125 mL Erlenmeyer flask (40 mL total solution volume). 2 mL aliquots of solution were removed for assay and their UV-Vis spectra recorded.

b) Penicillinase

Entrapment of Penicillinase (Type I from *Bacillus cereus*, lyophilized powder containing approx. 10% protein, Sigma) was performed as outlined above, using 50 mM pH 6.5 phosphate buffer. Penicillinase activity was determined using 100 mL of a 3 mM solution of Penicillin G (Benzylpenicillin, sodium salt, Sigma) in buffer. 2 mL aliquots of the reaction solution were removed for assay and their UV-Vis spectra recorded.

c) Tyrosinase

Entrapment of Tyrosinase (from mushroom, Sigma) was performed as outlined above, with 50 mM pH 6.5 phosphate buffer solution. Tyrosinase activity assays were performed using 0.3 mM L-tyrosine (Aldrich; 99+%) solution in buffer.

d) Tyrosine Decarboxylase

Entrapment of Tyrosine Decarboxylase (from *Streptococcus faecalis*, Fluka) was performed using 50 mM pH 5.5 acetate buffer and was accomplished by the method outlined above. The activity assay was accomplished using a 50:50 mixture of 2.5 mM solution of L-tyrosine (Aldrich, 99+%) in buffer and buffer. Total reaction volume for this assay was either 40 mL (19.5 h data reported herein) or 100 mL (all other data reported). 2 mL aliquots of reaction mixture were removed from the reaction vessel for assay. The method used for this assay was addition of 1 mL of a 1M K2CO3 solution to the 2 mL aliquot, followed by mixing. To this was added 2 drops of a solution of picrylsulfonic acid (5% w/v aqueous solution of 2,4,6-trinitrobenzenesulfonic acid, Sigma). The mixture was mixed well. 2 mL of toluene were added to this mixture, the layers shaken well, and centrifuged. The toluene layer was removed and its UV-Vis spectrum collected. Where applicable, a 0.1 mM solution of pyridoxal-5-phosphate monohydrate (98%, Aldrich) in buffer was substituted for the buffer solution in the assay mixture. Assays performed in the presence of cofactor were carried out in foil-covered reaction vessels due to the sensitivity of pyridoxal-5-phosphate to light.

3. Results of Enzyme Encapsulation and Assays a) b-Glucosidase entrapment yielded active matrices which were assayed using the synthetic substrate para-nitrophenyl-b-D-glucopyranoside, shown below. Enzymatic activity of matrix composites on the synthetic substrate results in cleavage of the glucosidic bond producing a bathochromic shift in the spectral band. This shift permits monitoring of the cleavage process, as illustrated in FIG. 1.

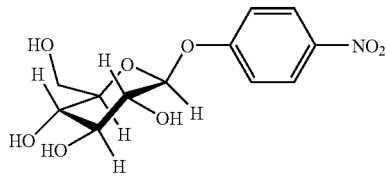

The synthetic substrate para-nitrophenyl-b-D-glucopyranoside.

b) Penicillinase entrapment provided active matrices which were assayed using the sodium salt of the synthetic substrate Benzylpenicillin, shown below. Conversion of penicillin to penicilloic acid via rupture of the β-lactam ring may be monitored spectrophotometrically, as shown in FIG. 2.

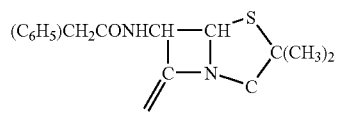

Substrate used for penicillinase activity assay, sodium benzylpenicillin

Reproducibility of the measurements done for penicillinase was checked by performing activity assay multiple times for the same matrix. As shown in FIG. 3(*a*), good agreement is observed for multiple assays performed over six consecutive days. Likewise, running multiple matrices from the same preparation to check reproducibility of the matrix entrapment shows good agreement, as seen in FIG. 3(*b*).

Loading studies utilizing penicillinase matrices were performed in which the enzyme concentration was varied over a wide range to determine the optimal enzyme concentration. The bar graph shown in FIG. 4 shows the effects of varying enzyme concentration on the activity of the matrix. The highest percentage of activity observed as a function of enzyme entrapped within the matrix (selected from the five compositions analyzed) occurs for the lowest concentration of enzyme examined, as shown in FIG. 5.

Surface area effects were also examined utilizing penicillinase matrices. Ten identical monoliths were prepared and aged simultaneously. Five of these were assayed as whole monoliths (cast in 4.5 mL cuvettes) while another five matrices were coarsely crushed and then assayed. This qualitative examination of surface area effects revealed that an increase in surface area does result in an increase in the enzyme activity observed, as shown in FIGS. 6 and 7. It should be noted that there is no leaching of enzyme observed from either the whole or crushed matrices, as determined by soaking the matrices in buffer solution overnight and subsequently checking the activity of the soak solution. The reproducibility of the measurements for the assays shown in FIG. 6 is quite reasonable, with the larger deviation in the crushed matrices attributable to the lack of control over particle size when breaking up the samples. FIG. 7, showing the mean values for each measurement with error bars, emphasizes the greater relative activity of the crushed matrix samples.

The significant effect of changing surface area on the observed enzyme activity prompted further investigation. Control over total surface area was achieved by casting the sol containing penicillinase into varying numbers of cell culture plate wells (22.6 mm diameter). By varying the amount of sol cast into a given well, the total 4 mL of material per matrix could be spread out over a number of wells and the disks cast in these wells could be recombined, after removal from the wells, for assay. Thus, the 4 mL of sol that constitutes one matrix preparation could be cast into one or multiple wells to generate samples with known, varying surface areas. Surface area stated for a given matrix reflects the initial surface area of the gel when freshly cast, and does not attempt to correct for any shrinkage that occurred during aging. FIG. 8(*a*) illustrates the difference in activity observed for matrices of varying surface areas. FIG. 8(*b*) shows the activity as a percentage of the penicillinase activity used in the preparation of the matrices.

c) Following entrapment of tyrosinase, the bifunctional activity of this enzyme was found to complicate spectrophotometric assay of the matrix composite due to the variation in molar extinction coefficient of the different species, and possible retention within the matrix. Tyrosinase possesses both cresolase (conversion of phenols to diphenols) and catecholase activity (conversion of diphenols to the corresponding quinone), as shown below. However, a qualitative analysis shows the conversion of the natural substrate L-tyrosine to L-dopa, which then undergoes dehydrogenation to give dopaquinone. Dopaquinone is unstable in aqueous solutions and undergoes a Michealis rearrangement to form, among other products, a number of melanin precursors which eventually polymerize to produce pigments. This complicated reaction may be followed qualitatively by monitoring a color change within the matrix. Although the L-tyrosine solution is, itself, colorless, the tyrosinase-containing matrices become noticeably darkened within one hour of contact with the substrate solution, suggesting formation of products with subsequent retention by the matrix. A solution of L-dopa in the presence of tyrosinase, likewise forms a gray-black precipitate.

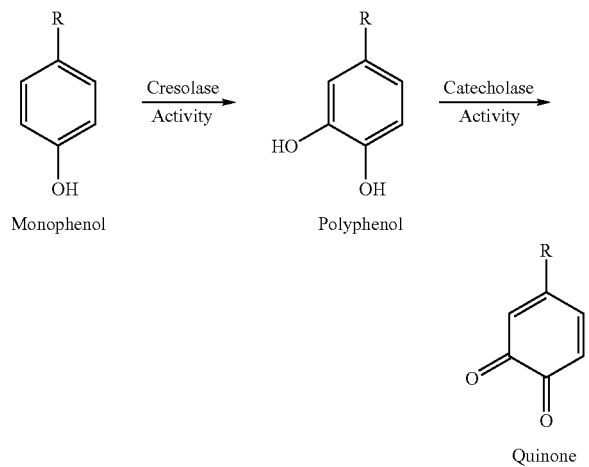

d) Active Tyrosine Decarboxylase matrices were and assayed using L-tyrosine as substrate. A complicating factor in the assay of entrapped Tyrosine Decarboxylase was the unavailability of a direct spectrophotometric method due to the equivalent molar extinction coefficients of substrate and product. The observation necessitated the development of an indirect assay provided by Phan et. al., *App. Biochem. Biotech.* 8:127 (1983). The results of an active Tyrosine Decarboxylase composite assay are shown in FIG. 9.

Longer aging times for Tyrosine Decarboxylase-containing matrices resulted in matrices for which no enzyme activity was observed without addition of cofactor. Addition of cofactor, pyridoxal-5-phosphate monohydrate (0.05 mM), to the assay mixture restored activity of the entrapped enzyme to varying degrees depending on the aging of the monolith. FIG. 10 shows activity assays for two 16 day old Tyrosine Decarboxylase-containing matrices, one without cofactor present and one with cofactor, and compares them to a matrix of the same composition assayed after aging 19 h. The activity observed at 19 h without cofactor and at 16 d with cofactor present are nearly identical, whereas without the presence of cofactor little, if any, activity is noted. For matrices aged 50 d a significant portion of the activity is retained in the presence in cofactor, although some loss of activity is observed.

B. Matrix Optimization Studies

1. Matrix Preparation

The general synthetic technique used for preparation of the silica sol was addition of appropriate aliquots of the organically substituted trimethoxysilane, tetramethyl orthosilicate and 4 mM HCl solution to a 25×150 mm test tube equipped with a stirbar. Total desired volume of sol was determined by the number of matrices to be prepared. The $RSi(OCH_3)_3$ and TMOS reagents were combined in appropriate ratios to yield the desired compositions.

| Reagent | Source |
| --- | --- |
| Tetramethylorthosilicate (TMOS) | Aldrich, 99+% |
| Methyltrimethoxysilane (MTMS) | Aldrich, 98% |
| Ethyltrimethoxysilane (ETMS) | Aldrich, 97+% |
| Trimethoxypropylsilane (TMPS) | Aldrich, 98% |
| iso-Butyltrimethoxysilane (i-BTMS) | Aldrich, 97% |
| n-Butyltrimethoxysilane (n-BTMS) | United Chemical Technologies, 95.3% |
| Phenyltrimethoxysilane (PTMS) | Aldrich, 97% |

As with 100% TMOS matrices, the mixture is stirred until homogeneous (approximately 15 minutes). The test tube containing the sol is then transferred to an ice bath and allowed to cool for 10 minutes. A 2 mL aliquot of sol is then transferred to another chilled test tube in an ice bath and stirred. To this sol, 1 mL of chilled buffer solution (appropriate to the enzyme to be entrapped) is added, and stirred for ca. 10 s, followed by addition of 1 mL of chilled, buffered solution containing the desired enzyme. The sol is swirled briefly, and then pipetted into a 4.5 mL polystyrene cuvette (cell culture dishes were also used for surface area study matrices). The cuvette opening is sealed with Parafilm following gel formation (cell culture dish covers were used for surface area study matrices). The gel is then allowed to age in the sealed container for a period of time ranging from 14 to 50 days or more at temperatures ranging from 4° C. to room temperature.

2. Enzyme Encapsulation and Assays

Entrapment of Penicillinase (Type 1 from *Bacillus cereus*, lyophillized powder containing approx. 10% protein, Sigma) was performed as outlined above, using 50 mM pH 6.5 phosphate buffer. Penicillinase activity was determined using 100 mL of a 3 mM solution of Penicillin G (Benzylpenicillin, sodium salt, Sigma) in buffer. 2 mL aliquots of the reaction solution were removed for assay and their UV-Vis spectra recorded.

3. Results of Enzyme Encapsulation and Assays

Initial examination of which matrix compositions provided matrices suitable for the purposes of this study excluded the n-butyltrimethoxysilane composition, as well as some of the higher ratios of other $RSi(OCH_3)_3$ precursors, due to the failure of these compositions to form a gel that was appropriate for our intended uses. Compositions examined, and their reactivity relative to 100% TMOS matrices are shown in Table 1.

TABLE 1

Activity for given compositions relative to 100% TMOS.

| | Composition | Relative Activity |
|---|---|---|
| MTMS:TMOS | 10% MTMS:90% TMOS | 108% |
| | 20% MTMS:80% TMOS | 82% |
| | 30% MTMS:70% TMOS | 92% |
| | 40% MTMS:60% TMOS | 104% |
| | 50% MTMS:50% TMOS | 112%* |
| ETMS:TMOS | 10% ETMS:90% TMOS | 99% |
| | 20% ETMS:80% TMOS | 93% |
| | 30% ETMS:70% TMOS | 99% |
| TMPS:TMOS | 10% TMPS:90% TMOS | 100% |
| | 20% TMPS:80% TMOS | 80% |
| i-BTMS:TMOS | 10% i-BTMS:90% TMOs | 90% |
| | 20% i-BTMS:80% TMOs | 75% |
| PTMS:TMOS | 10% PTMS:90% TMOS | 94% |

*Indicates a composition in which slight enzyme leaching is observed at the time of the assay. If insufficient aging is allowed, enzyme leaching is observed for methyltrimethoxysilane composition with MTMS content greater than 20%.

In addition, it was observed that as the matrices age the relative activity of the MTMS-containing matrices with respect to 100% TMOS drops. When matrices from the same preparation are assayed after aging 104 days at 4° C., the relative activity observed is shown in Table 2.

TABLE 2

Enzyme activity relative to 100% TMOS for varying MTMS-containing matrices aged 104 days.

| | Composition | Relative Activity |
|---|---|---|
| MTMS:TMOS | 10% MTMS:90% TMOS | 85% |
| | 20% MTMS:80% TMOS | 78% |
| | 30% MTMS:70% TMOS | 85% |
| | 40% MTMS:60% TMOS | 85% |
| | 50% MTMS:50% TMOS | 103%* |

*Indicates a composition in which no enzyme leaching is observed at the time of this assay, although leaching is observed for shorter aging time.

All publications and patents mentioned herein are hereby incorporated by reference in their entirety as if each individual publication or patent was specifically and individually indicated to be incorporated by reference and set forth in its entirety herein. In case of conflict, the present application, including any definitions herein, will control. In addition to the foregoing materials, the practice of the present invention may employ in part, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning a Laboratory Manual*, 2nd Ed., ed. by Sambrook, Fritsch and Maniatis (Cold Spring Harbor Laboratory Press: 1989); *DNA Cloning, Volumes I and II* (D. N. Glover ed., 1985); *Oligonucleotide Synthesis* (M. J. Gait ed., 1984); U.S. Pat. No. 4,683,195; *Nucleic Acid Hybridization* (B. D. Hames & S. J. Higgins eds. 1984); *Transcription and Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise *Methods In Enzymology* (Academic Press, Inc., N.Y.); *Gene Transfer Vectors for Mammalian Cells* (J. H. Miller and M. P. Calos eds., 1987, Cold Spring Harbor Laboratory); *Methods in Enzymology*, Vols. 154 and 155 (Wu et al. eds.), *Immunochemical Methods in Cell and Molecular Biology* (Mayer and Walker, eds., Academic Press, London, 1987); *Handbook of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986), all of which references are hereby incorporated by reference to the same extent as the other references specified herein.

The specification and examples should be considered exemplary only with the true scope and spirt of the invention suggested by the following claims.

What is claimed is:

1. A medical article comprising:
  a. an inorganic-based sol-gel matrix that is biocompatible; and,
  b. a first reaction center encapsulated in said matrix, wherein upon placing said article comprising said biocompatible matrix in contact with tissue and/or fluids of a subject, said first reaction center converts a first prodrug into a first biologically active agent.

2. The medical article of claim 1, wherein said first prodrug is endogenous to said subject and is more deleterious to said subject than said first biologically active agent.

3. The medical article of claim 1, wherein said fluid is blood of said subject.

4. The medical article of claim 1, wherein said article consists entirely of said biocompatible matrix.

5. The medical article of claim 2, wherein said article is implantable.

6. The medical article of claim 4, wherein said biocompatible matrix is attached to said article.

7. The medical article of claim 4, wherein said biocompatible matrix is attached to said article as a thin film.

8. The medical article of claim 4, wherein said biocompatible matrix is attached to said article in a capsule.

9. The medical article of claim 1, wherein said biocompatible matrix is incorporated within said article.

10. The medical article of claim 1, wherein said article is a tissue assist device, wherein said first reaction center provides a biological function characteristic of tissue of said subject.

11. The medical article of claim 10, wherein said contact occurs extracorporeal to said subject.

12. The medical article of claim 10, wherein said tissue of said subject is deficient in converting said first prodrug into said first biologically active agent.

13. A method for producing a medical article of claim 1 comprising:
  a. encapsulating a first cell-free reaction center in a biocompatible matrix; and
  b. shaping said matrix into a desired morphology;
wherein said biocompatible matrix comprises an inorganic-based sol-gel matrix and wherein said first reaction center converts a first prodrug into a first biologically active agent.

14. The method of claim 13, wherein said matrix is cast into a morphology selected from one of the following: cylindrical, rectangular, disk-shaped, patch-shaped, ovoid, stellate, or spherical.

15. The method of claim 13, wherein said matrix is cast or sprayed as a thin film onto said medical article.

16. The method of claim 13, wherein said biocompatible matrix comprises a silica-based sol-gel matrix.

17. The method of claim 13, wherein said biocompatible matrix is prepared from at least one type of oxysilane.

18. The method of claim 17, wherein said biocompatible matrix is prepared from more than one type of oxysilane.

19. The method of claim 13, wherein said biocompatible matrix is prepared from at least one type of inorganic oxide and at least one type of oxysilane.

20. A method for producing a medical article of claim 1 comprising:
   a. encapsulating a first cell-free reaction center in a biocompatible matrix;
   b. crushing said biocompatible matrix; and
   c. encapsulating said crushed biocompatible matrix;
wherein said biocompatible matrix comprises an inorganic-based sol-gel matrix and wherein said first reaction center converts a first prodrug into a first biologically active agent.

* * * * *